United States Patent [19]

Krumkalns

[11] 4,436,739
[45] Mar. 13, 1984

[54] SUBSTITUTED 1-THIA-3-AZA-4-ONES

[75] Inventor: Eriks V. Krumkalns, Indianapolis, Ind.

[73] Assignee: Eli Lilly and Company, Indianapolis, Ind.

[21] Appl. No.: 327,311

[22] Filed: Dec. 4, 1981

Related U.S. Application Data

[60] Division of Ser. No. 188,189, Sep. 18, 1980, abandoned, which is a continuation-in-part of Ser. No. 110,868, Jan. 9, 1980, abandoned, which is a continuation-in-part of Ser. No. 951,708, Oct. 16, 1978, abandoned.

[51] Int. Cl.$^3$ .................... A01N 43/40; A01N 43/86; C07D 401/04
[52] U.S. Cl. .................... 424/246; 424/263; 546/280; 544/54
[58] Field of Search ............... 424/263, 246; 546/280; 544/54

[56] References Cited

U.S. PATENT DOCUMENTS

| | | | |
|---|---|---|---|
| 2,839,404 | 6/1958 | Knott | 546/280 |
| 4,017,628 | 4/1977 | Nitidandhaprabhas | 424/263 |
| 4,053,471 | 10/1977 | Krapcho | 544/133 |
| 4,062,859 | 12/1977 | Weiler et al. | 260/302 |
| 4,067,878 | 1/1978 | Miller et al. | 260/299 |
| 4,080,457 | 3/1978 | Harrison et al. | 424/263 |
| 4,148,899 | 4/1979 | Mixan et al. | 424/263 |
| 4,150,026 | 4/1979 | Miller et al. | 260/299 |

FOREIGN PATENT DOCUMENTS

| | | | |
|---|---|---|---|
| 216672 | 1/1958 | Australia | 544/54 |
| 845519 | 9/1975 | Belgium . | |
| 847760 | 10/1975 | Belgium . | |
| 4129 | 1/1979 | European Pat. Off. . | |
| 2729414 | 5/1978 | Fed. Rep. of Germany . | |
| 48-1727673 | 5/1973 | Japan . | |
| 48-17276 | 5/1973 | Japan . | |
| 2031892A | 4/1980 | United Kingdom . | |

OTHER PUBLICATIONS

Fenech, Chemical Abstracts, vol. 54, 24723c.
Fenech, et al., Chem. Abstracts, vol. 55, 15465–15466 (1961).
Fenech, Chemical Abstracts, vol. 65, 4439–4440 (1966).
Fenech et al. Chem. Abstracts, vol. 71, 9716m (1969).
Vigorita et al., Chem. Abstracts, vol. 76, 152784r (1972).
DeiKalo, et al., Chem. Abstracts, vol. 78, 43343s (1978).
Seigi Miyano et al., Chem. Abstracts, vol. 79, 78784j (1978).
Pennington et al., J. Am. Chem. Soc., 75, 109–114 (1953).
Surrey et al. J. Am. Chem. Soc., 76 578–580 (1954).
Jadhav et al., J. Indian Chem. Soc., 55, 424–426 (1978).
Surrey, J. Am. Chem. Soc., 69, 2911–2912 (1947).
Troutman et al., J. Am. Chem. Soc., 70, 3436–3439 (1948).
Singh, J. Indian Chem. Soc., 595–597 (1976).

*Primary Examiner*—John M. Ford
*Attorney, Agent, or Firm*—Karen B. Dow; Arthur R. Whale

[57] ABSTRACT

Substituted 1-thia-3-aza-4-ones having utility as plant fungicides, herbicides and terrestrial and aquatic plant growth regulators, together with methods for the use thereof and compositions containing the compounds.

5 Claims, No Drawings

SUBSTITUTED 1-THIA-3-AZA-4-ONES

CROSS-REFERENCE

This application is a divisional of co-pending application Ser. No. 188,189, filed Sept. 18, 1980, now abandoned which was a continuation-in-part of Ser. No. 110,868, filed Jan. 9, 1980, now abandoned, which was a continuation-in-part of Ser. No. 951,708, filled Oct. 16, 1978, now abandoned.

BACKGROUND OF THE INVENTION

1. Field of the Invention

The field of the invention relates to heterocyclic organic compounds identified as 1-thia-3-aza-4-ones.

2. Description of the Prior Art

In the prior art, Surrey, *J. Am. Chem. Soc.* 69, 2911–2912 (1947), teaches the preparation of 4-thiazolidones by the reaction of thioglycolic acid with Schiff bases. This reference discloses no utilities for the compounds prepared as described therein.

Also in the prior art, Troutman, et al., *J. Am. Chem. Soc.* 70, 3436–3439 (1948), describe methods of synthesizing 2-aryl-3-alkyl- or 2-hetero-3-alkyl-4-thiazolidones, alleged to possess anticonvulsant activity.

Another prior art reference is Pennington et al., *J. Am. Chem. Soc.* 75, 109–114 (1953), which teaches the preparation of 2-substituted-4-thiazolidones, alleged to possess in vitro antitubercular activity.

Also in the prior art is Surrey et al., *J. Am. Chem. Soc.* 76, 578–580 (1954), which teaches the preparation of some 2-aryl-4-thiazolidones, alleged to possess significant amebicidal activity (*Endamoeba criceti*) when tested in hamsters.

Another prior art reference is that of Singh, *J. Indian Chem. Soc.*, 595–597 (1976), which teaches the synthesis of a number of 5-methyl-3-aryl-2-arylimino-4-thiazolidinones, which, together with the acetoxymercuri derivatives thereof, are alleged to possess fungicidal activity against *Alternaria solani*, as the test organism.

Yet another prior art reference is Japanese Pat. No. 48-17276, which is directed to the manufacture of thiazolidone derivatives bearing a 2-pyridyl moiety in the molecular structure. The compounds are alleged to have central nervous system inhibiting activity.

Still another prior art reference is U.S. Pat. No. 4,017,628 (Apr. 12, 1977), which is directed to the treatment of mange using a 2-pyridyl substituted thiazolidinone compound.

Also in the prior art is Jadhav et al., *J. Indian Chem. Soc.* 55, 424–426 (1978), which teaches the preparation of some 2-methyl-2-(2-hydroxy-4,5-dimethylphenyl)-3-aryl-4-thiazolidinones, alleged to be inhibitory at 100 ppm. against *Helmynthosporium appatarnae*. This compound showed no activity in our tests.

Another reference is identified by Derwent No. 68466B/38 *EP-4-129 (published Sept. 19, 1979), and is directed to 2,3-disubstituted thiazolidinone-4 derivatives, alleged to be useful as herbicides, plant growth regulants, pesticides, fungicides, algicides, and antivirals.

Another reference in the art is U.S. Pat. No. 4,148,899 (Apr. 10, 1979), which is directed to ((5-nitro-2-thiazolyl)thio)-polyhalogenated pyridines, alleged to exhibit activity against fungi and bacteria. The compounds are alleged to be useful for incorporation into materials which are subject to fungal attack, e.g., latex and alkyl paint films, wood and wooden products. The compounds of this reference differ from those of the above-identified application in that the thiazole ring is joined to the pyridine ring via a sulfur atom, and further, the thiazole ring contains no carbonyl moiety.

SUMMARY OF THE INVENTION

The present invention relates to novel 1-thia-3-aza-4-ones having utility as plant fungicides, terrestrial and aquatic growth regulators, herbicides, methods for the use thereof, and compositions containing the compounds.

DESCRIPTION OF THE PREFERRED EMBODIMENT

This invention relates to compounds of the formula

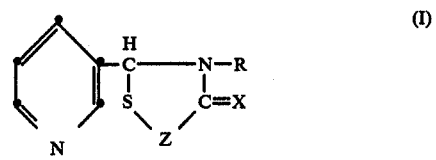

wherein

R is $C_3$–$C_{10}$ alkyl, $C_3$–$C_8$ cycloalkyl, methylallyl, phenyl, halophenyl, trifluoromethylphenyl, methoxybenzyl, methylbenzyl, halobenzyl, methylcyclohexyl, $C_3$–$C_8$ cycloalkyl ($C_1$–$C_3$)alkyl, α-methylbenzyl, 2-thiazolyl, nitrophenyl, phenoxyphenyl, (2-hydroxy-5-chloro)phenyl, (tetrahydro-2-furanyl)methyl, haloanilyl, trifluoromethylthiophenyl, methylthiophenyl, 2-norbornyl, furfuryl, 2-(1-methoxypropyl), methoxyphenyl, fluoro($C_1$–$C_2$)alkoxyphenyl, 3,4-(methylenedioxy)phenyl, 3,4-(methylenedioxy)benzyl, xylyl, tolyl, or halotolyl;

X is oxygen or sulfur;

Z is

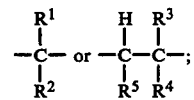

$R^1$ is hydrogen, $C_1$–$C_6$ alkyl, or —S($C_1$–$C_6$ alkyl);
$R^2$ is hydrogen, $C_1$–$C_6$ alkyl, or —S($C_1$–$C_6$ alkyl);
$R^3$ is hydrogen or methyl;
$R^4$ is hydrogen or $C_1$–$C_6$ alkyl; and
$R^5$ is hydrogen or methyl;
and acid addition salts thereof.

In one embodiment, this invention relates to compounds of the formula

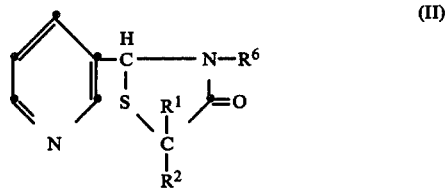

wherein
$R^1$ is hydrogen, $C_1$–$C_6$ alkyl, or —S($C_1$–$C_6$ alkyl);
$R^2$ is hydrogen, $C_1$–$C_6$ alkyl, or —S($C_1$–$C_6$ alkyl); and
$R^6$ is $C_3$–$C_{10}$ alkyl, $C_3$–$C_8$ cycloalkyl, methylallyl, halophenyl, phenyl, fluoro($C_1$–$C_2$)alkoxyphenyl, haloanilyl, α-methylbenzyl, 2-(1-methoxyphenyl), methylbenzyl, methoxybenzyl, xylyl, nitrophenyl, tolyl, methoxyphenyl, (2-hydroxy-5-chloro)phenyl, furfuryl, 3,4-(methylenedioxy)benzyl, 3,4-(methylenedioxy)phenyl, (tetrahydro-2-furanyl)methyl, trifluoromethylphenyl, methylcyclohexyl, $C_3$–$C_8$ cycloalkyl($C_1$–$C_3$)alkyl, phenoxyphenyl, 2-norbornyl, halobenzyl, 2-thiazolyl, trifluoromethylthiophenyl, halotolyl, or methylthiophenyl; and acid addition salts thereof.

In another embodiment, this invention relates to compounds of the formula

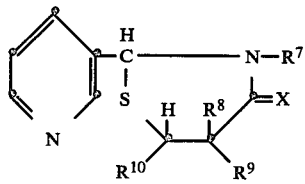
(III)

wherein
X is oxygen or sulfur;
$R^7$ is $C_5$–$C_6$ alkyl, $C_5$–$C_6$ cycloalkyl, halobenzyl, xylyl, halophenyl, methylthiophenyl, tolyl, trifluoromethylphenyl, or 1-(2-cyclopentyl-1-methyl)ethyl;
$R^8$ is hydrogen or methyl;
$R^9$ is hydrogen or $C_1$–$C_6$ alkyl; and
$R^{10}$ is hydrogen or methyl;
and acid addition salts thereof.

In yet another embodiment, this invention relates to a method of protecting plants from phytopathogenic fungi which comprises contacting the fungi with a fungicidally-effective and non-herbicidal amount of a compound of the formula

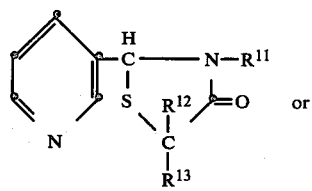
(IV)

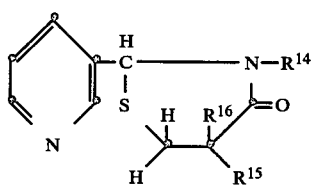
(V)

wherein
$R^{11}$ is $C_3$–$C_{10}$ alkyl, phenyl, halophenyl, methallyl, $C_3$–$C_8$ cycloalkyl, nitrophenyl, methylthiophenyl, methylcyclohexyl, fluoro($C_1$–$C_2$)alkoxyphenyl, tolyl, methoxyphenyl, trifluoromethylphenyl, halotolyl, halobenzyl, cyclohexylmethyl, 3,4-(methylenedioxy)benzyl, or xylyl;
$R^{12}$ is hydrogen, S($C_1$–$C_6$) alkyl, or $C_1$–$C_6$ alkyl;
$R^{13}$ is hydrogen, S($C_1$–$C_6$) alkyl, or $C_1$–$C_6$ alkyl;
$R^{14}$ is $C_3$–$C_6$ alkyl, $C_5$–$C_6$ cycloalkyl, halobenzyl, halophenyl, trifluoromethylphenyl, tolyl, or methoxyphenyl;
$R^{15}$ is hydrogen or methyl; and
$R^{16}$ is hydrogen or methyl;
or an acid addition salt thereof.

In still another embodiment, this invention relates to a method for regulating the growth of submerged and floating aquatic weeds which comprises adding to the water containing said weeds an amount sufficient to provide a growth-regulating and non-herbicidal concentration of a compound of the formula

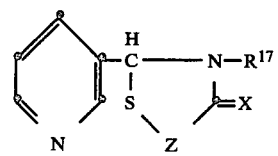
(VI)

wherein
$R^{17}$ is $C_3$–$C_{10}$ alkyl, $C_3$–$C_8$ cycloalkyl, (2-hydroxy-5-chloro)phenyl, methallyl, phenyl, halophenyl, trifluoromethylphenyl, 2-(1-methoxypropyl), methoxybenzyl, methylbenzyl, halobenzyl, $C_3$–$C_8$ cycloalkyl($C_1$–$C_3$)alkyl, methylcyclohexyl, α-methylbenzyl, phenoxyphenyl, (tetrahydro-2-furanyl)methyl, 2-thiazolyl, trifluoromethylthiophenyl, methylthiophenyl, methoxyphenyl, fluoro($C_1$–$C_2$)alkoxyphenyl, furfuryl, 3,4-(methylenedioxy)phenyl, 3,4-(methylenedioxy)benzyl, xylyl, 2-norbornyl, halotolyl, haloanilyl, or tolyl;
X is oxygen or sulfur;
Z is

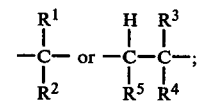

$R^1$ is hydrogen, $C_1$–$C_6$ alkyl, or —S($C_1$–$C_6$ alkyl);
$R^2$ is hydrogen, $C_1$–$C_6$ alkyl, or —S($C_1$–$C_6$ alkyl);
$R^3$ is hydrogen or methyl;
$R^4$ is hydrogen or $C_1$–$C_6$ alkyl; and
$R^5$ is hydrogen or methyl;
or an acid addition salt thereof.

In yet another embodiment, this invention relates to a method for regulating the growth of terrestrial plants which comprises applying to said plants or to the soil in which they are grown, a growth regulating and non-herbicidal amount of a compound of the formula

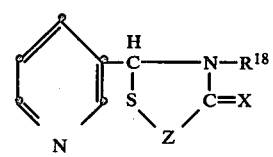
(VII)

wherein
$R^{18}$ is $C_3$–$C_{10}$ alkyl, $C_3$–$C_8$ cycloalkyl, phenyl, halophenyl, trifluoromethylphenyl, methoxybenzyl, methylbenzyl, halobenzyl, methylcyclohexyl, $C_3$–$C_8$ cycloalkyl ($C_1$–$C_3$) alkyl, α-methylbenzyl, (tetrahydro-2-furanyl)methyl, haloanilyl, trifluoromethylthiophenyl, furfuryl, 2-(1-methoxypropyl), methoxyphenyl, or xylyl;
X is oxygen or sulfur;
Z is

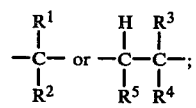

$R^1$ is hydrogen, $C_1$–$C_6$ alkyl, or —S($C_1$–$C_6$ alkyl);

$R^2$ is hydrogen, $C_1$–$C_6$ alkyl, or —S($C_1$–$C_6$ alkyl);
$R^3$ is hydrogen or methyl;
$R^4$ is hydrogen or $C_1$–$C_6$ alkyl; and
$R^5$ is hydrogen or methyl;
or an acid addition salt thereof.

Another embodiment of this invention relates to a method of controlling undesired plant growth which comprises applying to the plants or the soil where such plant growth is undesired, a herbicidal amount of a compound of the formula

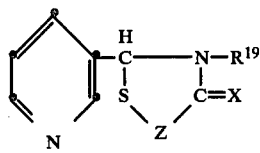 (VIII)

wherein
$R^{19}$ is $C_3$–$C_{10}$ alkyl, $C_3$–$C_8$ cycloalkyl, methylallyl, phenyl, halophenyl, trifluoromethylphenyl, methoxybenzyl, methylbenzyl, halobenzyl, methylcyclohexyl, $C_3$–$C_8$ cycloalkyl ($C_1$–$C_3$) alkyl, α-methylbenzyl, phenoxyphenyl, trifluoromethylthiophenyl, xylyl, tolyl, or halotolyl;

X is oxygen or sulfur;
Z is

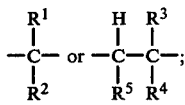

$R^1$ is hydrogen, $C_1$–$C_6$ alkyl, or —S($C_1$–$C_6$ alkyl);
$R^2$ is hydrogen, $C_1$–$C_6$ alkyl, or —S($C_1$–$C_6$ alkyl);
$R^3$ is hydrogen or methyl;
$R^4$ is hydrogen or $C_1$–$C_6$ alkyl; and
$R^5$ is hydrogen or methyl;
or an acid addition salt thereof.

This invention also relates to a method of controlling the growth of fungi which comprises contacting the fungi with a fungicidally-effective amount of a compound of the formula

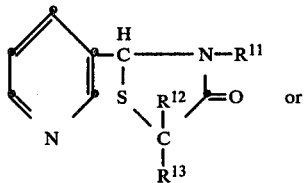 (IV)

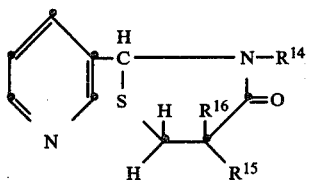 (V)

wherein
$R^{11}$ is $C_3$–$C_{10}$ alkyl, phenyl, halophenyl, methallyl, $C_3$–$C_8$ cycloalkyl, nitrophenyl, methylthiophenyl, methylcyclohexyl, fluoro($C_1$–$C_2$)alkoxyphenyl, tolyl, methoxyphenyl, trifluoromethylphenyl, halotolyl, halobenzyl, cyclohexylmethyl, 3,4-(methylenedioxy)benzyl, or xylyl;

$R^{12}$ is hydrogen, S($C_1$–$C_6$) alkyl, or $C_1$–$C_6$ alkyl;
$R^{13}$ is hydrogen, S($C_1$–$C_6$) alkyl, or $C_1$–$C_6$ alkyl;
$R^{14}$ is $C_3$–$C_6$ alkyl, $C_5$–$C_6$ cycloalkyl, halobenzyl, halophenyl, trifluoromethylphenyl, tolyl, or methoxyphenyl;
$R^{15}$ is hydrogen or methyl; and
$R^{16}$ is hydrogen or methyl;
or an acid addition salt thereof.

In the above formulae, $C_3$–$C_{10}$ alkyl represents n-propyl, isopropyl, n-butyl, sec.-butyl, isobutyl, t-butyl, n-pentyl, isopentyl, sec.-pentyl, t-pentyl, n-hexyl, sec.-hexyl, isohexyl, t-hexyl, n-heptyl, isoheptyl, sec.-heptyl, n-octyl, sec.-octyl, isooctyl, n-nonyl, sec.-nonyl, isononyl, n-decyl, sec.-decyl, and the like.

$C_1$–$C_6$ alkyl represents methyl, ethyl, n-propyl, isopropyl, n-butyl, sec.-butyl, isobutyl, t-butyl, n-pentyl, isopentyl, sec.-pentyl, t-pentyl, n-hexyl, sec.-hexyl, isohexyl, t-hexyl, and the like.

The term —S($C_1$–$C_6$ alkyl) represents alkylthio such as methylthio, ethylthio, n-propylthio, isopropylthio, n-butylthio, isobutylthio, sec.-butylthio, t-butylthio, n-amylthio, isoamylthio, sec.-amylthio, n-hexylthio, sec.-hexylthio, isohexylthio, and the like.

$C_3$–$C_8$ Cycloalkyl represents saturated monocyclic cycloalkyl such as cyclopropyl, cyclobutyl, cyclopentyl, cyclohexyl, cycloheptyl, and cyclooctyl.

Halophenyl represents o-chlorophenyl, p-chlorophenyl, p-fluorophenyl, p-bromophenyl, p-iodophenyl, m-chlorophenyl, o-bromophenyl, o-fluorophenyl, 2,4-difluorophenyl, 2,5-dichlorophenyl, 2,5-dibromophenyl, 2,4-dichlorophenyl, 2-bromo-4-chlorophenyl, 2,4-dibromophenyl, 3,4-difluorophenyl, 4-bromo-2-chlorophenyl, 4-bromo-3-fluorophenyl, 3,4-dichlorophenyl, 3,4-dibromophenyl, 4-chloro-3-fluorophenyl, 3,5-difluorophenyl, 3,5-dichlorophenyl, 3,5-dibromophenyl, 2,3,4-trichlorophenyl, 2,4,5-trichlorophenyl, 2,3,4,5-tetrachlorophenyl, and the like.

Halobenzyl represents o-chlorobenzyl, p-chlorobenzyl, p-fluorobenzyl, p-bromobenzyl, p-iodobenzyl, m-chlorobenzyl, m-bromobenzyl, m-fluorobenzyl, 2,4-dichlorobenzyl, 2-bromo-4-chlorobenzyl, 3,4-dibromobenzyl, 2,5-dichlorobenzyl, 3,5-dibromobenzyl, 4-chloro-3-fluorobenzyl, 2,5-difluorobenzyl, and the like.

Haloanilyl represents p-chloroanilyl, o-chloroanilyl, m-chloroanilyl, 2,6-dichloroanilyl, p-bromoanilyl, o-bromoanilyl, o-fluoroanilyl, m-fluoroanilyl, 3,5-difluoroanilyl, 2,6-difluoroanilyl, and the like.

Fluoro($C_1$–$C_2$)alkoxyphenyl represents trifluoromethoxyphenyl, 1,1,2,2-tetrafluoroethoxyphenyl and pentafluoroethoxyphenyl.

$C_3$–$C_8$ Cycloalkyl($C_1$–$C_3$)alkyl represents cyclopropylmethyl, cyclobutylmethyl, cyclopentylmethyl, cyclohexylmethyl, cyclopropylethyl, cyclobutylethyl, cyclopentylethyl, cyclohexylethyl, cycloheptylethyl, cyclooctylethyl, cycloheptylmethyl, cyclooctylmethyl, cyclopropylpropyl, cyclobutylpropyl, cyclopentylpropyl, cycloheptylpropyl, cyclooctylpropyl, 1-(2-cyclopentyl-1-methyl)ethyl, 1-cyclohexylpropyl, and the like.

Methoxyphenyl represents 4-methoxyphenyl, 3,4-dimethoxyphenyl, 3-methoxyphenyl, and 3,5-dimethoxyphenyl.

Halo or halogen is chlorine, bromine, iodine, or fluorine.

Xylyl represents 3,4-dimethylphenyl, 2,3-dimethylphenyl, 3,5-dimethylphenyl, 2,4-dimethylphenyl, and 2,5-dimethylphenyl.

Tolyl represents o-, m-, and p-tolyl.

Halotolyl represents (3-chloro-4-methyl)phenyl, (4-bromo-3-methyl)phenyl, (3-bromo-4-methyl)phenyl, (4-chloro-3-methyl)phenyl, and the like.

Acid addition salts of the 1-thia-3-aza-4-ones can be readily formed by reacting the compound with an acid such as hydrochloric acid, hydrobromic acid, sulfuric acid, maleic acid, phosphoric acid, p-toluenesulfonic acid and the like. Preferred acid addition salts are the hydrochlorides.

In one embodiment of this invention, compounds coming within the scope of generic formula (I) set forth above and acid addition salts thereof have been found effective for regulating the growth of aquatic weeds when applied to the locus of the weeds at a concentration in the range of from about 0.25 to about 10 ppm., suitably at a concentration in the range of from about 0.25 to about 2 ppm.

The compounds preferred for use in the novel aquatic growth regulating embodiment of this invention are of the formula (I) above wherein R is cyclopentyl, cyclohexyl, 1-methylhexyl, 4-chlorobenzyl, o-tolyl, 2-chlorophenyl, 2-fluorophenyl, 2,4-difluorophenyl, 4-chlorophenyl, and 2,4-dichlorophenyl;

Z is

$R^1$ is hydrogen or methyl; and
$R^2$ is hydrogen, methyl, n-propyl, or n-butyl.

Another embodiment of this invention relates to a method of protecting plants from phytopathogenic fungi which comprises contacting the loci of the fungi, be that some portion of the plant, namely leaves, stems, flowers or roots, or the soil wherein the fungi may be located, with a fungicidally-effective but non-herbicidal amount of a compound of formula (I), supra or acid addition salt thereof. Application rates will vary according to whether the method of protecting plants from phytopathogenic fungi is practised in a greenhouse or out of doors in the field, as well as with the severity of the fungal infection. Thus, for use in a greenhouse, the fungicidal compound is applied as a soil drench using a composition having a concentration in the range of from about 1 to about 200 ppm. of active ingredient, preferably from about 5 to about 100 ppm. As is well understood by those of ordinary skill in the art, application rates for use in the field are usually greater than for use in a greenhouse, and range from about 25 to about 1000 ppm.

Novel compounds of the present invention have been shown by suitable tests to control a number of fungi, including *Erysiphe graminis tritici*, the causative organism of powdery mildew of wheat; *Erysiphe cichoracearum*, the causative organism of cucumber powdery mildew; *Erysiphe polygoni*, the causative organism of bean powdery mildew; *Helminthosporium sativum*, the causative organism of Helminthosporium leaf spot; *Venturia inaequalis*, the causative organism of apple scab; *Plasmopara viticola*, the causative organism of grape downy mildew; *Cercospora beticola*, the causative organism of Cercospora leaf spot; *Septoria tritici*, the causative organism of Septoria leaf blotch; *Rhizoctonia solani*, the causative organism of Rhizoctonia damping-off; and *Cercosporella herpotrichoides* the causative organism of foot rot or eye spot on wheat.

The compounds preferred for use in the embodiment of this invention relating to a method of protecting plants from plant pathogenic fungi are of the formula (I) above wherein R is halophenyl, cyclohexyl or tolyl;
Z is

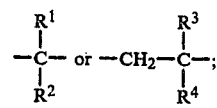

$R^1$ is hydrogen or methyl;
$R^2$ is hydrogen, methyl, or propyl;
$R^3$ is hydrogen or methyl; and
$R^4$ is hydrogen or methyl.

The fungicidal activity of the compounds of this invention is not limited to phytopathogenic fungi which infect plants. The compounds are active against and can be used to control various other fungi. Thus, this invention encompasses a method of controlling the growth of fungi by contacting the fungi with a fungicidally effective amount of a compound of formula IV or V, supra or an acid addition salt thereof. The amount of compound required to control a given species of fungus can readily be determined by one skilled in the art without undue experimentation. Compounds of this invention have been shown to be particularly active in in vitro tests against *Candida Albicans*.

Another embodiment of this invention relates to regulating the growth of terrestrial plants or the soil in which they are grown a plant growth regulating and non-herbicidal amount of a compound of formula (VII), supra or an acid addition salt thereof. The expression "plant growth regulating" is used herein to refer to modification of the growth processes of the plant without substantial herbicidal injury to the plant.

The compounds preferred for use in the embodiment of this invention relating to a method of regulating the growth of terrestrial plants are of formula VII above wherein $R^{18}$ is halophenyl, cyclohexyl or xylyl;
Z is

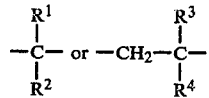

$R^1$ is hydrogen or methyl;
$R^2$ is hydrogen or methyl;
$R^3$ is hydrogen or methyl; and
$R^4$ is hydrogen or methyl.

The amount of active compound applied to produce the desired plant growth regulatory effect varies greatly depending on the particular compound and the species of plant. Typically the active compound should be applied at a rate of about 0.2 to about 20 kilograms of active compound per hectare and preferably from about 0.5 to about 10 kilograms per hectare. One skilled in the art will readily be able without undue experimentation to determine the amount of compound to apply to a given plant species to achieve the desired growth regulation without unacceptable herbicidal injury.

Another embodiment of this invention relates to a method of controlling undesired plant growth which comprises applying to such plants or the soil where such plant growth is undesired, a herbicidal amount of a compound of formula (VIII) supra or an acid addition salt thereof. The amount of active compound applied in this embodiment is that which will produce a herbicidal effect. The herbicidal effect can be complete kill of the plants or severe interruption of the normal growth processes of the plants.

The amount of active compound applied to achieve this herbicidal effect depends on the particular active compound and on the plants to be controlled. Typically active compound should be applied at a rate of about 0.5 to about 50 kilograms active compound per hectare, preferably about 0.5 to about 20 kilograms per hectare. Some of the compounds of this invention exhibit both plant growth regulatory and herbicidal activity. Generally the amount of such compound applied to control or severely inhibit undesired plant growth will be greater than that applied to regulate the growth of plants. However, the amount to be applied for the desired effect varies greatly depending on the target plant species. An amount of a particular active compound which will have a herbicidal effect and kill one plant species may have no effect or a plant growth regulatory effect on a different plant species.

The compounds preferred for use in the embodiment of this invention relating to a method of controlling undesirable plant growth are compounds of formula (VIII) above wherein $R^{19}$ is halophenyl, $C_3$–$C_8$ cycloalkyl or xylyl;

X is

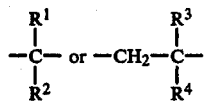

$R^1$ is hydrogen or methyl,
$R^2$ is hydrogen or methyl,
$R^3$ is hydrogen or methyl, and
$R^4$ is hydrogen or methyl.

The novel compounds of this invention are prepared by the following described methods, varying somewhat depending upon whether the particular compound is a thiazolidinone or a thiazinone. Those substituted 1-thia-3-aza-4-one compounds identified as substituted 4-thiazolidinone compounds are prepared according to the following general reaction sequence:

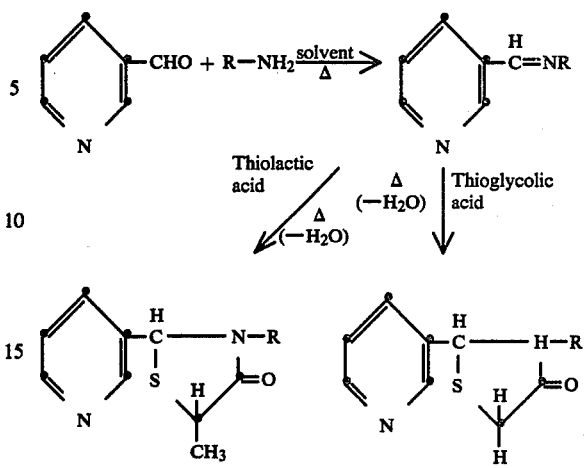

wherein R has the same values as set forth hereinabove.

Thus, in carrying out the reaction, a suitably substituted aniline, alkylamine, or cycloalkylamine, is dissolved in a water-immiscible solvent inert to the conditions of the reaction to be carried out, and to this solution there is added the 3-pyridylcarboxaldehyde. A catalyst, such as p-toluene sulfonic acid can be used, if desired. Suitable solvents include benzene, toluene, xylene, and the like. The mixture is refluxed for a period of time during which water, which is a by-product of the reaction, is collected in a suitable water trap, for instance, the Dean-Stark trap. After the calculated amount of water given off by the reaction mixture has been collected, the reaction mixture is cooled to approximately room temperature, an excess of thioglycolic ($\alpha$-mercaptoacetic acid) or thiolactic acid (2-mercaptopropionic acid) is added, and the reaction mixture again refluxed until no more water is collected in the Dean-Stark trap. This requires approximately 4 hours. The reaction product mixture is cooled, concentrated to dryness in vacuo, and purified by recrystallization of the residue from a suitable solvent, or by column chromatography. By this general procedure the 4-thiazolidinones are prepared, which compounds have a 5-membered heterocyclic nucleus. The preparation of the compounds can be carried out in a continuous manner without isolation of the intermediate reaction products, if desired.

The method used to prepare the tetrahydro thiazin-4-one compounds, the compounds with a 6-membered heterocyclic nucleus, is carried out stepwise according to the following general reaction sequence:

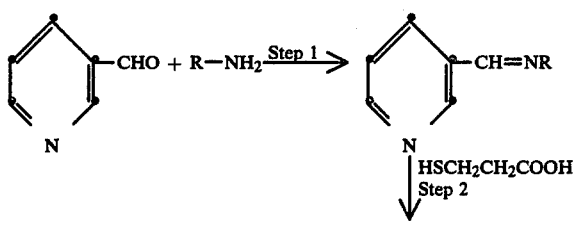

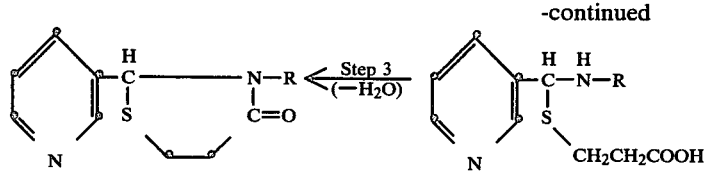

R has the same values as set forth hereinabove. Again, the reaction can be carried out continuously without isolation of the intermediate products of each step, if desired.

In Step 1, a mixture of the 3-pyridylcarboxaldehyde, a suitably substituted alkylamine, cycloalkylamine, or aniline, and an inert water-immiscible solvent, such as toluene, benzene, xylene, or the like, is refluxed under a Dean-Stark trap to collect the water given off by the reaction. The reaction mixture is cooled, filtered, and concentrated in vacuo. The residue is purified by crystallization or column chromatography. The product of this step is identified as a 3-[(substituted phenylimino)-methyl]pyridine, and is used in Step 2, as described hereinafter.

The 3-[(substituted phenylimino)methyl]pyridine is mixed with β-mercaptopropionic acid and an inert water-immiscible solvent, such as toluene, benzene, or xylene, and allowed to stand at room temperature overnight, or allowed to reflux for a few hours. The product of this reaction is isolated in crude form by concentrating the reaction mixture in vacuo. The crude product, identified as a 3-[α-(substituted anilino)-α-(3-pyridyl)-methylthio]propionic acid, is used in Step 3 of the preparation, as follows.

In Step 3, the 3-[α-(substituted anilino)α-(3-pyridyl)-methylthio]propionic acid is allowed to react with N,N'-dicyclohexylcarbodiimide in an inert solvent, at ambient room temperature for from about 3 to about 15 hours, or at elevated temperature until substantially complete reaction occurs. Suitable inert solvents include methylene chloride, chloroform, carbon tetrachloride, and ethylene dichloride. The solid which separates is filtered off and discarded. The filtrate is concentrated to dryness in vacuo to leave a residue which is purified by usual procedures, such as recrystallization or column chromatography. The product is identified as the desired 3-(substituted phenyl)tetrahydro-2-(3-pyridyl)-4H-1,3-thiazin-4-one.

Those compounds of this invention wherein Z is

and $R^1$ and/or $R^2$ equal hydrogen; wherein Z is

and $R^3=R^4=R^5=$hydrogen; are conveniently alkylated by methods known to those of ordinary skill in the art. The alkylation appears to occur at the position alpha to the carbonyl function of the 4-thiazolidinone or thiazin-4-one ring. Thus, for example, 3-(4-chlorophenyl)-5-methyl-2-(3-pyridyl)-4-thiazolidinone, dissolved in tetrahydrofuran, is added with stirring to a mixture of a hexane solution of n-butyllithium and tetrahydrofuran, maintained under an atmosphere of dry nitrogen, and cooled to a temperature of about −50° C. to about −70° C. After stirring the reaction mixture for about one-half hour at about −70° C., methyl iodide is added dropwise, with stirring, and then the reaction mixture is stirred for about 12 hours, and allowed to warm gradually to ambient room temperature. The reaction product mixture is worked up by adding water thereto and extracting with ether. The ether extracts are dried, concentrated in vacuo, and the residue recrystallized from a suitable solvent, in the present case a mixture of petroleum ether (BP 60°–70° C.) and ethyl ether, to yield product having a melting point of about 140°–141° C., and identified as 3-(4-chlorophenyl)-5,5-dimethyl-2-(3-pyridyl)-4-thiazolidinone.

The preparation of those compounds wherein the carbonyl oxygen is replaced by sulfur is carried out by allowing the carbonyl oxygen compound to react with phosphorus pentasulfide in a suitable solvent, preferably dry pyridine, at a temperature of about 90° C. for a period of about 18 hours, and then isolating the product.

Thus, for example, 3-(4-chlorophenyl)tetrahydro-2-(3-pyridyl)-4H-1,3-thiazin-4-one is mixed with dry pyridine and heated to a temperature of about 90° C., whereby a solution is obtained. To this solution phosphorus pentasulfide is added portionwise, with stirring and heating, and when the addition is complete, the reaction mixture is heated at about 90° C., and stirred overnight, that is, for about 18 hours. The reaction mixture is then cooled and the pyridine solvent evaporated in vacuo, leaving a viscous, oily, residue, which is washed by triturating it with water. The oil is then taken up in a solvent, in this case a mixture of ethanol and dimethylformamide, decolorized with carbon, filtered, and the ethanol removed in vacuo. The dimethylformamide solution is poured slowly into cold water, whereby a solid precipitates. The solid is extracted into ethyl acetate, and the extract washed with cold aqueous sodium chloride solution. The ethyl acetate solution is concentrated in vacuo to yield an oil which is chromatographed over a silica gel column using ethyl acetate as solvent and eluant. The viscous oil product obtained in this manner is crystallized from a suitable solvent, in this case a mixture of ethyl acetate and ether, and there is obtained product having a melting point of about 115°–117° C., identified by elemental analyses as 3-(4-chlorophenyl)tetrahydro-2-(3-pyridyl)-4H-1,3-thiazin-4-thione.

Suitable acid addition salts of these compounds are readily prepared by the usual procedures well-known to those skilled in the art, using acids selected from the group consisting of hydrochloric, hydrobromic, sulfuric, p-toluene-sulfonic, and the like.

It must be noted that compounds of generic formula (I), supra, occur as stereoisomers when Z is

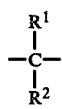

wherein $R^1 \neq R^2$; when Z is

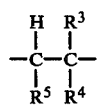

wherein $R^3 \neq R^4$ when $R^5 = H$; and when Z is

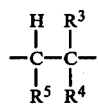

wherein $R^5 \neq H$ when $R^3$ and $R^4$ are both hydrogen or both methyl. Such stereoisomers are capable of being separated through the application of suitable resolving agents, or chromatography, as is well-recognized by those of ordinary skill in the art.

The synthesis of the compounds is more specifically illustrated following the above general procedures, which are not to be regarded as limiting the scope of the invention.

EXAMPLE 1

3-(4-Chlorophenyl)-5-methyl-2-(3-pyridyl)-4-thiazolidinone

In a round bottomed 3-neck flask equipped with a condenser, Dean-Stark trap, and a mechanical stirrer, there was placed 25.4 g. (0.27 mole) of 4-chloroaniline (commercially available), and 250 ml. of toluene. With stirring, there was added to this solution 21.4 g. (0.27 mole) of 3-pyridylcarboxaldehyde (commercially available), and the reaction mixture refluxed until the calculated amount of water (approximately 3.6 ml.) had been collected in the Dean-Stark trap. The hot reaction mixture was cooled to room temperature and an excess of thiolactic acid (commercially available), totaling 30 g., was added and the reaction mixture again heated to reflux until no more water was collected in the Dean-Stark trap. This required about 4 hours of heating. The reaction mixture was then cooled and concentrated to dryness in vacuo. The solid residue was recrystallized from a mixture of hot ethyl ether and acetone to yield product having a melting point of about 120° C., and identified by infrared and NMR spectra, and elemental analyses as 3-(4-chlorophenyl)-5-methyl-2-(3-pyridyl)-4-thiazolidinone. Wt. 7 g.

Analyses calculated for $C_{15}H_{13}ClN_2OS$:

|   | Theoretical | Found |
|---|---|---|
| C | 59.11 | 59.23 |
| H | 4.30 | 4.26 |
| N | 9.19 | 9.19 |

Following the general procedure of Example 1, additional compounds were prepared and identified. The compounds, together with the principal starting materials and weights thereof used in the preparations, are listed in the examples set forth hereinafter.

EXAMPLE 2

3-(2,4-Difluorophenyl)-2-(3-pyridyl)-4-thiazolidinone, having a melting point of about 125°–127° C., from 13 g. of 2,4-difluoroaniline, 10 g. of 3-pyridylcarboxaldehyde, and 13 g. of thioglycolic acid. Wt. 15 g.

Analyses calculated for $C_{14}H_{10}F_2N_2OS$:

|   | Theoretical | Found |
|---|---|---|
| C | 57.53 | 57.80 |
| H | 3.45 | 3.68 |
| N | 9.58 | 9.61 |

EXAMPLE 3

3-(2-Fluorophenyl)-2-(3-pyridyl)-4-thiazolidinone, having a melting point of about 142°–143° C., from 15 g. of 2-fluoroaniline, 15 g. of 3-pyridylcarboxaldehyde, and 13 g. of thioglycolic acid. Wt. 8 g.

Analyses calculated for $C_{14}H_{11}FN_2OS$:

|   | Theoretical | Found |
|---|---|---|
| C | 61.30 | 61.50 |
| H | 4.04 | 4.34 |
| N | 10.21 | 10.07 |

EXAMPLE 4

3-Nonyl-2-(3-pyridyl)-4-thiazolidinone, having a melting point of about 82°–83° C., from 11.2 g. of n-nonylamine, 15 g. of 3-pyridylcarboxaldehyde, and 13 g. of thioglycolic acid. Wt. 2.3 g.

Analyses calculated for $C_{17}H_{26}N_2OS$:

|   | Theoretical | Found |
|---|---|---|
| C | 66.62 | 66.38 |
| H | 8.55 | 8.22 |
| N | 9.14 | 8.85 |

EXAMPLE 5

3-(4-Chlorobenzyl)-2-(3-pyridyl)-4-thiazolidinone, having a melting point of about 134° C., from 15 g. of 4-chlorobenzylamine, 15 g. of 3-pyridylcarboxaldehyde, and 13 g. of thioglycolic acid. Wt. 20 g.

Analyses calculated for $C_{15}H_{13}ClN_2OS$:

|   | Theoretical | Found |
|---|---|---|
| C | 59.11 | 58.78 |
| H | 4.30 | 4.42 |
| N | 9.19 | 8.89 |

EXAMPLE 6

3-Cyclopentyl-2-(3-pyridyl)-4-thiazolidinone, having a melting point of about 118°–119° C., from 12 g. of cyclopentylamine, 15 g. of 3-pyridylcarboxaldehyde, and 13 g. of thioglycolic acid. Wt. 6.5 g.

Analyses calculated for $C_{13}H_{16}N_2OS$:

|   | Theoretical | Found |
|---|---|---|
| C | 62.87 | 63.01 |
| H | 6.49 | 6.21 |

|   | Theoretical | Found |
|---|---|---|
| N | 11.28 | 11.19 |

EXAMPLE 7

3-Phenyl-2-(3-pyridyl)-4-thiazolidinone, having a melting point of about 177°–178° C., from 13 g. of aniline, 15 g. of 3-pyridylcarboxaldehyde, and 13 g. of thioglycolic acid. Wt. 9 g.

Analyses calculated for $C_{14}H_{12}N_2OS$:

|   | Theoretical | Found |
|---|---|---|
| C | 65.60 | 65.44 |
| H | 4.72 | 4.89 |
| N | 10.93 | 10.76 |

EXAMPLE 8

3-(2-Methylallyl)-2-(3-pyridyl)-4-thiazolidinone, having a melting point of about 84° C., from 15 g. of 2-methylallylamine, 20 g. of 3-pyridylcarboxaldehyde, and 20 g. of thioglycolic acid. Wt. 23 g.

Analyses calculated for $C_{12}H_{14}N_2OS$:

|   | Theoretical | Found |
|---|---|---|
| C | 61.54 | 61.56 |
| H | 6.02 | 5.90 |
| N | 11.96 | 11.70 |

EXAMPLE 9

3-(1-Methylhexyl)-2-(3-pyridyl)-4-thiazolidinone, having a melting point of about 67° C., from 16 g. of 2-aminoheptane, 15 g. of 3-pyridylcarboxaldehyde, and 13 g. of thioglycolic acid. Wt. 3 g.

Analyses calculated for $C_{15}H_{22}N_2OS$:

|   | Theoretical | Found |
|---|---|---|
| C | 64.71 | 64.70 |
| H | 7.97 | 7.76 |
| N | 10.06 | 9.97 |

EXAMPLE 10

3-(3-Chlorophenyl)-2-(3-pyridyl)-4-thiazolidinone, having a melting point of about 154°–155° C., from 13 g. of 3-chloroaniline, 10 g. of 3-pyridylcarboxaldehyde, and 10 g. of thioglycolic acid. Wt. 13 g.

Analyses calculated for $C_{14}H_{11}ClN_2OS$:

|   | Theoretical | Found |
|---|---|---|
| C | 57.83 | 57.63 |
| H | 3.81 | 4.07 |
| N | 9.63 | 9.66 |

EXAMPLE 11

2-(3-Pyridyl)-3-($\alpha,\alpha,\alpha$-trifluoro-m-tolyl)-4-thiazolidinone, as an oil, from 16 g. of 3-trifluoromethylaniline, 15 g. of 3-pyridylcarboxaldehyde, and 13 g. of thioglycolic acid. Wt. 8 g.

Analyses calculated for $C_{15}H_{11}F_3N_2OS$:

|   | Theoretical | Found |
|---|---|---|
| C | 55.55 | 55.79 |
| H | 3.42 | 3.56 |
| N | 8.64 | 8.75 |

EXAMPLE 12

3-(4-Fluorophenyl)-2-(3-pyridyl)-4-thiazolidinone, having a melting point of about 161° C., from 55.5 g. of 4-fluoroaniline, 53.5 g. of 3-pyridylcarboxaldehyde, and 46 g. of thioglycolic acid. Wt. 70 g.

Analyses calculated for $C_{14}H_{11}FN_2OS$:

|   | Theoretical | Found |
|---|---|---|
| C | 61.30 | 61.08 |
| H | 4.04 | 4.15 |
| N | 10.21 | 10.17 |

EXAMPLE 13

3-(Cyclohexylmethyl)-2-(3-pyridyl)-4-thiazolidinone, having a melting point of about 70° C., from 11.3 g. of cyclohexanemethanamine, 10 g. of 3-pyridylcarboxaldehyde, and 10 g. of thioglycolic acid. Wt. 15 g. Identified by NMR spectrum.

EXAMPLE 14

3-(3,5-Dichlorophenyl)-2-(3-pyridyl)-4-thiazolidinone, having a melting point of about 160°–161° C., from 16.2 g. of 3,5-dichloroaniline, 11 g. of 3-pyridylcarboxaldehyde, and 10 g. of thioglycolic acid. Wt. 11 g. Identified by NMR spectrum.

EXAMPLE 15

3-(2-Fluorobenzyl)-2-(3-pyridyl)-4-thiazolidinone, having a melting point of about 103° C., from 12.5 g. of 2-fluorobenzylamine, 10.7 g. of 3-pyridylcarboxaldehyde, and 10 g. of thioglycolic acid. Wt. 6 g. Identified by NMR and IR spectra.

EXAMPLE 16

3-[3,4-(Methylenedioxy)benzyl]-2-(3-pyridyl)-4-thiazolidinone, having a melting point of about 121°–122° C., from 15.1 g. of piperonylamine, 11 g. of 3-pyridylcarboxaldehyde, and 14 g. of thioglycolic acid. Wt. 4 g.

Analyses calculated for $C_{16}H_{14}N_2O_3S$:

|   | Theoretical | Found |
|---|---|---|
| C | 61.13 | 60.95 |
| H | 4.49 | 4.45 |
| N | 8.90 | 8.83 |

EXAMPLE 17

3-(3,4-Dichlorophenyl)-2-(3-pyridyl)-4-thiazolidinone, having a melting point of about 160°–162° C., from 16.2 g. of 3,4-dichloroaniline, 11g. of 3-pyridylcarboxaldehyde, and 14 g. of thioglycolic acid. Wt. 14 g.

Analyses calculated for $C_{14}H_{10}Cl_2N_2OS$:

|   | Theoretical | Found |
|---|---|---|
| C | 51.70 | 51.54 |

-continued

| | Theoretical | Found |
|---|---|---|
| H | 3.10 | 2.96 |
| N | 8.62 | 8.54 |

EXAMPLE 18

3-(2,4-Dichlorophenyl)-2-(3-pyridyl)-4-thiazolidinone, having a melting point of about 170°–171° C., from 16.2 g. of 2,4-dichloroaniline, 12 g. of 3-pyridylcarboxaldehyde, and 12 g. of thioglycolic acid. Wt. 4 g.

Analyses calculated for $C_{14}H_{10}Cl_2N_2OS$:

| | Theoretical | Found |
|---|---|---|
| C | 51.70 | 51.52 |
| H | 3.10 | 2.90 |
| N | 8.62 | 8.62 |

EXAMPLE 19

3-(4-Chlorophenyl)-2-(3-pyridyl)-4-thiazolidinone, having a melting point of about 149°–151° C., from 9 g. of 4-chloroaniline, 7.5 g. of 3-pyridylcarboxaldehyde, and 15 g. of thioglycolic acid. Wt. 9 g.

Analyses calculated for $C_{14}H_{11}ClN_2OS$:

| | Theoretical | Found |
|---|---|---|
| C | 57.83 | 58.73 |
| H | 3.81 | 4.47 |
| N | 9.63 | 9.48 |

EXAMPLE 20

2-(3-Pyridyl)-3-[3-(1,1,2,2-tetrafluoroethoxy)phenyl]-4-thiazolidinone, as an oil, from 21 g. of 3-tetrafluoroethoxyaniline, 11 g. of 3-pyridylcarboxaldehyde, and 14 g. of thioglycolic acid. Wt. 4 g.

Analyses calculated for $C_{16}H_{12}F_4N_2O_2S$:

| | Theoretical | Found |
|---|---|---|
| C | 51.61 | 51.84 |
| H | 3.25 | 3.19 |
| N | 7.52 | 7.32 |

EXAMPLE 21

3-Cyclohexyl-2-(3-pyridyl)-4-thiazolidinone, having a melting point of about 110°–111° C., from 10 g. of cyclohexylamine, 15 g. of 3-pyridylcarboxaldehyde, and 13 g. of thioglycolic acid. Wt. 4.6 g.

Analyses calculated for $C_{14}H_{18}N_2OS$:

| | Theoretical | Found |
|---|---|---|
| C | 64.09 | 63.90 |
| H | 6.92 | 6.72 |
| N | 10.68 | 10.44 |

EXAMPLE 22

3-Cyclopropyl-2-(3-pyridyl)-4-thiazolidinone, having a melting point of about 112°–113° C., from 8 g. of cyclopropylamine, 15 g. of 3-pyridylcarboxaldehyde, and 13 g. of thioglycolic acid. Wt. 16 g.

Analyses calculated for $C_{11}H_{12}N_2OS$:

| | Theoretical | Found |
|---|---|---|
| C | 60.00 | 60.11 |
| H | 5.45 | 5.32 |
| N | 12.73 | 12.55 |

EXAMPLE 23

3-(3-Chlorophenyl)-5-methyl-2-(3-pyridyl)-4-thiazolidinone, having a melting point of about 133° C., from 18 g. of 3-chloroaniline, 15 g. of 3-pyridylcarboxaldehyde, and 13 g. of thiolactic acid. Wt. 9.5 g.

Analyses calculated for $C_{15}H_{13}ClN_2OS$:

| | Theoretical | Found |
|---|---|---|
| C | 59.11 | 58.98 |
| H | 4.30 | 4.26 |
| N | 9.19 | 9.10 |

EXAMPLE 24

3-(2-Chlorophenyl)-2-(3-pyridyl)-4-thiazolidinone, having a melting point of about 134° C., from 18 g. of 2-chloroaniline, 15 g. of 3-pyridylcarboxaldehyde, and 13 g. of thioglycolic acid. Wt. 4.6 g.

Analyses calculated for $C_{14}H_{11}ClN_2OS$:

| | Theoretical | Found |
|---|---|---|
| C | 57.83 | 57.49 |
| H | 3.81 | 3.74 |
| N | 9.63 | 9.32 |

EXAMPLE 25

2-(3-Pyridyl)-3-(4-tolyl)-4-thiazolidinone, having a melting point of about 187° C., from 15 g. of p-toluidine, 15 g. of 3-pyridylcarboxaldehyde, and 13 g. of thioglycolic acid. Wt. 16 g.

Analyses calculated for $C_{15}H_{14}N_2OS$:

| | Theoretical | Found |
|---|---|---|
| C | 66.64 | 66.79 |
| H | 5.22 | 5.13 |
| N | 10.36 | 10.58 |

EXAMPLE 26

3-(4-Methoxyphenyl)-2-(3-pyridyl)-4-thiazolidinone, having a melting point of about 144°–145° C., from 17 g. of 4-methoxyaniline, 15 g. of 3-pyridylcarboxaldehyde, and 13 g. of thioglycolic acid. Wt. 5 g.

Analyses calculated for $C_{15}H_{14}N_2O_2S$:

| | Theoretical | Found |
|---|---|---|
| C | 62.92 | 63.20 |
| H | 4.93 | 5.05 |
| N | 9.78 | 9.99 |

EXAMPLE 27

2-(3-Pyridyl)-3-(α,α,α-trifluoro-p-tolyl)-4-thiazolidinone, having a melting point of about 148° C., from 16 g. of 4-aminobenzotrifluoride, 15 g. of 3-pyridylcarboxaldehyde, and 13 g. of thioglycolic acid. Wt. 8 g.

Analyses calculated for $C_{15}H_{11}F_3N_2OS$:

|   | Theoretical | Found |
|---|---|---|
| C | 55.55 | 55.15 |
| H | 3.42 | 3.41 |
| N | 8.64 | 8.85 |

EXAMPLE 28

3-Hexyl-2-(3-pyridyl)-4-thiazolidinone, having a melting point of about 78° C., from 12 g. of n-hexylamine, 11 g. of 3-pyridylcarboxaldehyde, and 10 g. of thioglycolic acid. Wt. 21 g.

Analyses calculated for $C_{14}H_{20}N_2OS$:

|   | Theoretical | Found |
|---|---|---|
| C | 63.60 | 63.52 |
| H | 7.63 | 7.47 |
| N | 10.60 | 10.59 |

EXAMPLE 29

3-Cyclohexyl-5-methyl-2-(3-pyridyl)-4-thiazolidinone, having a melting point of about 106° C., from 10 g. of cyclohexylamine, 10.7 g. of 3-pyridylcarboxaldehyde, and 10.6 g. of thiolactic acid. Wt. 13 g.

Analyses calculated for $C_{15}H_{20}N_2OS$:

|   | Theoretical | Found |
|---|---|---|
| C | 65.18 | 65.40 |
| H | 7.29 | 7.00 |
| N | 10.14 | 10.00 |

EXAMPLE 30

5-Methyl-3-(4-tolyl)-2-(3-pyridyl)-4-thiazolidinone, having a melting point of about 170° C., from 10.7 g. of p-toluidine, 10.7 g. of 3-pyridylcarboxaldehyde, and 10.6 g. of thiolactic acid. Wt. 18 g.

Analyses calculated for $C_{16}H_{16}N_2OS$:

|   | Theoretical | Found |
|---|---|---|
| C | 67.57 | 68.32 |
| H | 5.67 | 5.29 |
| N | 9.85 | 9.86 |

EXAMPLE 31

3-(4-Chlorobenzyl)-5-methyl-2-(3-pyridyl)-4-thiazolidinone, as an oil, from 14 g. of 4-chlorobenzylamine, 10.7 g. of 3-pyridylcarboxaldehyde, and 10.6 g. of thiolactic acid. Wt. 7.9 g.

Analyses calculated for $C_{16}H_{15}ClN_2OS$:

|   | Theoretical | Found |
|---|---|---|
| C | 60.28 | 60.42 |
| H | 4.71 | 4.61 |
| N | 8.79 | 8.59 |

EXAMPLE 32

3-(2-Chlorophenyl)-5-methyl-2-(3-pyridyl)-4-thiazolidinone, having a melting point of about 104°–105° C., from 12.7 g. of 2-chloroaniline, 10.7 g. of 3-pyridylcarboxaldehyde, and 10.6 g. of thiolactic acid. Wt. 600 mg.

Analyses calculated for $C_{15}H_{13}ClN_2OS$:

|   | Theoretical | Found |
|---|---|---|
| C | 59.11 | 59.32 |
| H | 4.30 | 4.54 |
| N | 9.19 | 8.95 |

EXAMPLE 33

5-Methyl-3-(1-methylhexyl)-2-(3-pyridyl)-4-thiazolidinone, as an oil, from 11.5 g. of 2-aminoheptane, 10.7 g. of 3-pyridylcarboxaldehyde, and 10.6 g. of thiolactic acid. Wt. 14 g.

Analyses calculated for $C_{16}H_{24}N_2OS$:

|   | Theoretical | Found |
|---|---|---|
| C | 65.71 | 65.49 |
| H | 8.27 | 8.18 |
| N | 9.58 | 9.32 |

EXAMPLE 34

3-Hexyl-5-methyl-2-(3-pyridyl)-4-thiazolidinone, having a melting point of about 67°–68° C., from 10.1 g. of n-hexylamine, 10.7 g. of 3-pyridylcarboxaldehyde, and 10.6 g. of thiolactic acid. Wt. 5.7 g.

Analyses calculated for $C_{15}H_{22}N_2OS$:

|   | Theoretical | Found |
|---|---|---|
| C | 64.71 | 64.61 |
| H | 7.97 | 7.77 |
| N | 10.05 | 10.05 |

EXAMPLE 35

3-(2-Fluorophenyl)-5-methyl-2-(3-pyridyl)-4-thiazolidinone, having a melting point of about 105° C., from 11 g. of 2-fluoroaniline, 10.7 g. of 3-pyridylcarboxaldehyde, and 10.6 g. of thiolactic acid. Wt. 16 g.

Analyses calculated for $C_{15}H_{13}FN_2OS$:

|   | Theoretical | Found |
|---|---|---|
| C | 62.48 | 62.26 |
| H | 4.54 | 4.52 |
| N | 9.72 | 9.64 |

EXAMPLE 36

3-(4-Fluorophenyl)-5-methyl-2-(3-pyridyl)-4-thiazolidinone, having a melting point of about 148° C., from 22.2 g. of 4-fluoroaniline, 21.4 g. of 3-pyridylcarboxaldehyde, and 24 g. of thiolactic acid. Wt. 36 g.

Analyses calculated for $C_{15}H_{13}FN_2OS$:

|   | Theoretical | Found |
|---|---|---|
| C | 62.48 | 62.56 |
| H | 4.54 | 4.31 |

| | Theoretical | Found |
| --- | --- | --- |
| N | 9.72 | 9.41 |

EXAMPLE 37

3-(3-Nitrophenyl)-2-(3-pyridyl)-4-thiazolidinone, having a melting point of about 114°–115° C., from 13.8 g. of 3-nitroaniline, 11 g. of 3-pyridylcarboxaldehyde, and 9 g. of thioglycolic acid. Wt. 1.5 g.

Analyses calculated for $C_{14}H_{11}N_3O_3S$:

| | Theoretical | Found |
| --- | --- | --- |
| C | 55.81 | 55.74 |
| H | 3.65 | 3.69 |
| N | 13.95 | 13.77 |

EXAMPLE 38

3-(4-Phenoxyphenyl)-2-(3-pyridyl)-4-thiazolidinone, having a melting point of about 168°–170° C., from 26 g. of 4-phenoxyaniline, 15 g. of 3-pyridylcarboxaldehyde, and 13 g. of thioglycolic acid. Wt. 26 g.

Analyses calculated for $C_{20}H_{16}N_2O_2S$:

| | Theoretical | Found |
| --- | --- | --- |
| C | 68.94 | 68.80 |
| H | 4.63 | 4.60 |
| N | 8.04 | 7.91 |

EXAMPLE 39

3-(2-Cyclopentyl-1-methylethyl)-5-methyl-2-(3-pyridyl)-4-thiazolidinone, having a melting point of about 102° C., from 26 g. of α-methylcyclopentaneethylamine, 22 g. 3-pyridylcarboxaldehyde, and 25 g. of thiolactic acid. Identified by NMR spectrum. Wt. 2 g.

EXAMPLE 40

5-Methyl-3-(α-methylbenzyl)-2-(3-pyridyl)-4-thiazolidinone, having a melting point of about 89° C., from 12 g. of α-methylbenzylamine, 10.7 g. of 3-pyridylcarboxaldehyde, and 10.7 g. of thiolactic acid. Wt. 1.8 g.

Analyses calculated for $C_{17}H_{18}N_2OS$:

| | Theoretical | Found |
| --- | --- | --- |
| C | 68.43 | 68.17 |
| H | 6.08 | 5.87 |
| N | 9.39 | 9.31 |

EXAMPLE 41

3-Isopropyl-5-methyl-2-(3-pyridyl)-4-thiazolidinone, having a melting point of about 110°—111° C., from 11.8 g. of isopropylamine, 20.0 g. of 3-pyridylcarboxaldehyde, and 22.0 g. of thiolactic acid. Wt. 21 g.

Analyses calculated for $C_{12}H_{16}N_2OS$:

| | Theoretical | Found |
| --- | --- | --- |
| C | 60.99 | 60.76 |
| H | 6.82 | 6.54 |
| N | 11.85 | 12.07 |

EXAMPLE 42

3-(3,5-Xylyl)-5-methyl-2-(3-pyridyl)-4-thiazolidinone, having a melting point of about 140°–142° C., from 12.5 g. of 3,5-dimethylaniline, 11 g. of 3-pyridylcarboxaldehyde, and 12 g. of thiolactic acid. Wt. 12 g.

Analyses calculated for $C_{17}H_{18}N_2OS$:

| | Theoretical | Found |
| --- | --- | --- |
| C | 68.42 | 68.17 |
| H | 6.08 | 5.83 |
| N | 9.39 | 9.31 |

EXAMPLE 43

2-(3-Pyridyl)-3-(2-thiazolyl)-4-thiazolidinone, having a melting point of about 164°–165° C., from 14.0 g. of 2-aminothiazole, 15.0 g. of 3-pyridylcarboxaldehyde, and 13.0 g. of thioglycolic acid. Wt. 2.0 g.

Analyses calculated for $C_{11}H_9N_3OS_2$:

| | Theoretical | Found |
| --- | --- | --- |
| C | 50.17 | 50.37 |
| H | 3.44 | 3.51 |
| N | 15.96 | 15.88 |

EXAMPLE 44

3-(3,4-Xylyl)-5-methyl-2-(3-pyridyl)-4-thiazolidinone, having a melting point of about 189° C., from 12.1 g. of 3,4-dimethylaniline, 10.7 g. of 3-pyridylcarboxaldehyde, and 12 g. of thiolactic acid. Wt. 16 g.

Analyses calculated for $C_{17}H_{18}N_2OS$:

| | Theoretical | Found |
| --- | --- | --- |
| C | 68.43 | 68.64 |
| H | 6.08 | 6.22 |
| N | 9.39 | 9.29 |

EXAMPLE 45

3-(5-Chloro-2-hydroxyphenyl)-5-methyl-2-(3-pyridyl)-4-thiazolidinone, having a melting point of about 205°–207° C., from 8.61 g. of 5-chloro-2-hydroxyaniline, 6.43 g. of 3-pyridylcarboxaldehyde, and 6.7 g. of thiolactic acid. Wt. 9.1 g.

Analyses calculated for $C_{15}H_{13}ClN_2O_2S$:

| | Theoretical | Found |
| --- | --- | --- |
| C | 56.16 | 55.90 |
| H | 4.08 | 3.86 |
| N | 8.73 | 8.68 |

EXAMPLE 46

3-(2-Norbonyl)-2-(3-pyridyl)-4-thiazolidinone, having a melting point of about 143° C., from 14 g. of norbonylamine hydrochloride, 15 g. of 3-pyridylcarboxaldehyde, and 13 g. of thioglycolic acid. Wt. 7.5 g.

Analyses calculted for $C_{15}H_{18}N_2OS$:

| | Theoretical | Found |
| --- | --- | --- |
| C | 65.66 | 65.39 |
| H | 6.61 | 6.40 |

|   | Theoretical | Found |
|---|---|---|
| N | 10.21 | 10.05 |

EXAMPLE 47

3-Isopropyl-2-(3-pyridyl)-4-thiazolidinone, having a melting point of about 119°–120° C., from 7 g. of isopropylamine, 15 g. of 3-pyridylcarboxaldehyde, and 13 g. of thioglycolic acid. Wt. 12 g.
Analyses calculated for $C_{11}H_{14}N_2OS$:

|   | Theoretical | Found |
|---|---|---|
| C | 59.43 | 59.19 |
| H | 6.35 | 6.25 |
| N | 12.60 | 12.32 |

EXAMPLE 48

3-(Cyclohexylmethyl)-5-methyl-2-(3-pyridyl)-4-thiazolidinone, having a melting point of about 73°–74° C., from 10.7 g. of 3-pyridylcarboxaldehyde, 11.3 g. of cyclohexanemethanamine, and 10.8 g. of thiolactic acid. Wt. 11 g.
Analyses calculated for $C_{16}H_{22}N_2OS$:

|   | Theoretical | Found |
|---|---|---|
| C | 66.17 | 65.91 |
| H | 7.64 | 7.47 |
| N | 9.65 | 9.69 |

EXAMPLE 49

3-Cyclooctyl-5-methyl-2-(3-pyridyl)-4-thiazolidinone, having a melting point of about 58°–61° C., from 12.7 g. of cyclooctylamine, 10.7 g. of 3-pyridylcarboxaldehyde, and 10.6 g. of thiolactic acid. Wt. 11.2 g.
Analyses calculated for $C_{17}H_{24}N_2OS$:

|   | Theoretical | Found |
|---|---|---|
| C | 67.07 | 66.89 |
| H | 7.95 | 7.72 |
| N | 9.20 | 9.33 |

EXAMPLE 50

5-Methyl-3-phenyl-2-(3-pyridyl)-4-thiazolidinone, having a melting point of about 159°–161° C., from 18.6 g. of aniline, 21.4 g. of 3-pyridylcarboxaldehyde, and 21.2 g. of thiolactic acid. Wt. 15 g.
Analyses calculated for $C_{15}H_{14}N_2OS$:

|   | Theoretical | Found |
|---|---|---|
| C | 66.64 | 66.59 |
| H | 5.22 | 5.07 |
| N | 10.36 | 10.59 |

EXAMPLE 51

5-Methyl-3-(2-tolyl)-2-(3-pyridyl)-4-thiazolidinone, as an oil, from 21.4 g. of 2-toluidine, 21.4 g. of 3-pyridylcarboxaldehyde, and 25 g. of thiolactic acid. Wt. 6 g.
Analyses calculated for $C_{16}H_{16}N_2OS$:

|   | Theoretical | Found |
|---|---|---|
| C | 67.57 | 67.54 |
| H | 5.67 | 5.57 |
| N | 9.85 | 10.02 |

EXAMPLE 52

5-Methyl-3-(4-methylthiophenyl)-2-(3-pyridyl)-4-thiazolidinone, having a melting point of about 147°–148° C., from 17.5 g. of 4-methylthioaniline hydrochloride, 10.7 g. of 3-pyridylcarboxaldehyde, and 12 g. of thiolactic acid. Wt. 23 g.
Analyses calculated for $C_{16}H_{16}N_2OS_2$:

|   | Theoretical | Found |
|---|---|---|
| C | 60.73 | 60.63 |
| H | 5.10 | 4.90 |
| N | 8.85 | 9.00 |

EXAMPLE 53

5-Methyl-3-[2-(1-methoxypropyl)]-2-(3-pyridyl)-4-thiazolidinone, having a melting point of about 111°–112° C., from 8.9 g. of 2-amino-1-methoxypropane, 10.7 g. of 3-pyridylcarboxaldehyde, and 15 g. of thiolactic acid. Wt. 2.1 g. Identified by NMR spectrum.

EXAMPLE 54

3-(4-Nitrophenyl)-2-(3-pyridyl)-4-thiazolidinone, having a melting point of about 142°–143° C., from 13.8 g. of 4-nitroaniline, 11 g. of 3-pyridylcarboxaldehyde, and 9 g. of thioglycolic acid. Wt. 4.0 g.
Analyses calculated for $C_{14}H_{11}N_3O_3S$:

|   | Theoretical | Found |
|---|---|---|
| C | 55.81 | 55.66 |
| H | 3.68 | 3.61 |
| N | 13.95 | 13.62 |

EXAMPLE 55

3-(4-Bromo-3-methylphenyl)-5-methyl-2-(3-pyridyl)-4-thiazolidinone, having a melting point of about 127°–129° C., from 11.2 g. of 4-bromo-3-methylaniline, 6.4 g. of 3-pyridylcarboxaldehyde, and 6.7 g. of thiolactic acid. Wt. 12.2 g.
Analyses calculated for $C_{16}H_{15}BrN_2OS$:

|   | Theoretical | Found |
|---|---|---|
| C | 52.90 | 51.64 |
| H | 4.20 | 4.22 |
| N | 7.71 | 7.82 |

EXAMPLE 56

3-(2,4-Difluorophenyl)-5-methyl-2-(3-pyridyl)-4-thiazolidinone, having a melting point of about 102° C., from 6 g. of 2,4-difluoroaniline, 6 g. of 3-pyridylcarboxaldehyde, and 8 g. of thiolactic acid. Wt. 3.2 g.
Analyses calculated for $C_{15}H_{12}F_2N_2OS$:

|   | Theoretical | Found |
|---|---|---|
| C | 58.81 | 58.69 |
| H | 3.91 | 3.94 |
| N | 9.14 | 8.84 |

EXAMPLE 57

3-(4-Iodophenyl)-5-methyl-2-(3-pyridyl)-4-thiazolidinone, having a melting point of about 149°–150° C., from 21.9 g. of 4-iodoaniline, 11 g. of 3-pyridylcarboxaldehyde, and 12 g. of thiolactic acid. Wt. 12 g.

Analyses calculated for $C_{15}H_{13}IN_2OS$:

|   | Theoretical | Found |
|---|---|---|
| C | 45.47 | 45.24 |
| H | 3.31 | 3.09 |
| N | 7.07 | 6.97 |

EXAMPLE 58

5-Methyl-3-(4-methylbenzyl)-2-(3-pyridyl)-4-thiazolidinone, having a melting point of about 96° C., from 12 g. of 4-methylbenzylamine, 10.7 g. of 3-pyridylcarboxaldehyde, and 10.7 g. of thiolactic acid. Wt. 4.9 g.

Analyses calculated for $C_{17}H_{18}N_2OS$:

|   | Theoretical | Found |
|---|---|---|
| C | 68.43 | 68.33 |
| H | 6.08 | 5.79 |
| N | 9.39 | 9.21 |

EXAMPLE 59

5-Methyl-3-(4-methylcyclohexyl)-2-(3-pyridyl)-4-thiazolidinone, having a melting point of about 108°–109° C., from 11.5 g. 4-methylcyclohexylamine, 10.5 g. of 3-pyridylcarboxaldehyde, and 11 g. thiolactic acid. Wt. 500 mg.

Analyses calculated for $C_{16}H_{22}N_2OS$:

|   | Theoretical | Found |
|---|---|---|
| C | 6.17 | 66.45 |
| H | 7.64 | 7.82 |
| N | 9.65 | 9.78 |

EXAMPLE 60

3-(2,4-Dichlorobenzyl)-2-(3-pyridyl)-5-methyl-4-thiazolidinone, having a melting point of about 125°–126° C., from 17.6 g. of 2,4-dichlorobenzylamine, 10.7 g. of 3-pyridylcarboxaldehyde, and 12 g. of thiolactic acid. Wt. 15 g.

Analyses calculated for $C_{16}H_{14}Cl_2N_2OS$:

|   | Theoretical | Found |
|---|---|---|
| C | 54.40 | 54.38 |
| H | 3.99 | 3.71 |
| N | 7.93 | 8.08 |

EXAMPLE 61

3-(2-Methoxybenzyl)-5-methyl-2-(3-pyridyl)-4-thiazolidinone, as an oil, from 13.7 g. of 2-methoxybenzylamine, 10.5 g. of 3-pyridylcarboxaldehyde, and 10.7 g. of thiolactic acid. Wt. 2 g.

Analyses calculated for $C_{17}H_{18}N_2O_2S$:

|   | Theoretical | Found |
|---|---|---|
| C | 64.94 | 64.71 |
| H | 5.77 | 5.53 |
| N | 8.91 | 8.97 |

EXAMPLE 62

3-(2-Furfuryl)-5-methyl-2-(3-pyridyl)-4-thiazolidinone, having a melting point of about 74° C., from 19.4 g. of furfurylamine, 22 g. of 3-pyridylcarboxaldehyde, and 25 g. of thiolactic acid. Wt. 6 g.

Analyses calculated for $C_{14}H_{14}N_2O_2S$:

|   | Theoretical | Found |
|---|---|---|
| C | 61.29 | 60.91 |
| H | 5.14 | 5.30 |
| N | 10.21 | 10.43 |

EXAMPLE 63

5-Methyl-2-(3-pyridyl)-3-[(tetrahydro-2-furanyl)methyl]-4-thiazolidinone, having a melting point of about 86°–87° C., from 10.6 g. of 3-pyridylcarboxaldehyde, 10.1 g. of tetrahydro-2-furanmethaneamine, and 10.7 g. of thiolactic acid. Wt. 5.5 g.

Analyses calculated for $C_{14}H_{18}N_2O_2S$:

|   | Theoretical | Found |
|---|---|---|
| C | 60.41 | 60.15 |
| H | 6.52 | 6.36 |
| N | 10.06 | 10.20 |

EXAMPLE 64

3-(2,4-Dichlorophenyl)-5-methyl-2-(3-pyridyl)-4-thiazolidinone, having a melting point of about 87°–89° C., from 25 g. of N-(3-pyridylmethylene)aniline (having a melting point of about 94° C., and obtained from allowing 54 g. of 3-pyridylcarboxaldehyde to react with 80 g. of 2,4-dichloroaniline in 400 ml. toluene with a trace of p-toluenesulfonic acid) and 15 g. of thiolactic acid. Wt. 5 g.

Analyses calculated for $C_{15}H_{12}Cl_2N_2OS$:

|   | Theoretical | Found |
|---|---|---|
| C | 53.11 | 52.00 |
| H | 3.57 | 3.91 |
| N | 8.26 | 8.11 |

EXAMPLE 64A

3-[(2,6-Dichlorophenyl)amino]-5-methyl-2-(3-pyridyl)-4-thiazolidinone, having a melting point of about 198°–200° C., from 11 g. of 3-pyridylcarboxaldehyde, 21.3 g. of 2,6-dichlorophenylhydrazine hydrochloride, and 7 g. of thiolactic acid. Wt. 2 g.

Analyses calculated for $C_{15}H_{13}Cl_2N_3OS$:

|   | Theoretical | Found |
|---|---|---|
| C | 50.86 | 50.86 |
| H | 3.70 | 3.62 |
| N | 11.84 | 12.03 |

EXAMPLE 64B 3-(3-Chloro-4-methylphenyl)-5-methyl-2-(3-pyridyl)-4-thiazolidinone, having a melting point of about 150°–160° C., from 6.43 g. of 3-pyridylcarboxaldehyde, 8.5 g. of 3-chloro-4-methylaniline, and 6.7 g. of thiolactic acid. Wt. 10.5 g.

Analyses calculated for $C_{16}H_{15}ClN_2OS$:

|   | Theoretical | Found |
|---|---|---|
| C | 60.28 | 60.10 |
| H | 4.74 | 4.93 |
| N | 8.79 | 8.76 |

EXAMPLE 64C 3-(2,4-Xylyl)-5-methyl-2-(3-pyridyl)-4-thiazolidinone, having a melting point of about 121°–123° C., from 25 g. of 2,4-dimethylaniline, 22 g. of 3-pyridylcarboxaldehyde, and 24 g. of thiolactic acid. Wt. 14 g. Identified by NMR spectrum.

EXAMPLE 64D 3-(2-Trifluoromethylphenyl)-5-methyl-2-(3-pyridyl)-4-thiazolidinone, having a melting point of about 136° C., from 24.0 g. of 2-trifluoromethylaniline, 16.0 g. of 3-pyridylcarboxaldehyde, and 18.0 g. of thiolactic acid. Wt. 4 g. Identified by NMR spectrum.

EXAMPLE 64E

3-[3,4-(Methylenedioxy)phenyl]-5-methyl-2-(3-pyridyl)-4-thiazolidinone, having a melting point of about 203°–204° C., from 28.0 g of 3,4-(methylenedioxy)aniline, 22.0 g. of 3-pyridylcarboxaldehyde, and 25.0 g. of thiolactic acid. Wt. 9 g. Identified by NMR spectrum.

EXAMPLE 64F 3-(2,6-difluorophenyl)-5-methyl-2-(3-pyridinyl)-4-thiazolidinone, having a melting point of about 154°–156° C., from 25 g. of 2,6-difluoroaniline, 20 g. of 3-pyridinecarboxaldehyde and 11 g. of thiolactic acid. Wt. 5 g. Identified by NMR spectrum.

EXAMPLE 64G

3-[3,5-bis(trifluoromethyl)phenyl]-5-methyl-2-(3-pyridinyl)-4-thiazolidinone, having a melting point of about 97°–98° C. from 33 g. of 3-pyridinecarboxaldehyde, 70 g. of 3,5-(ditrifluoromethyl)aniline and 10 g. of thiolactic acid. Identified by NMR spectrum.

EXAMPLE 64H 3-(2,4,6-trifluorophenyl)-5-methyl-2-(3-pyridinyl)-4-thiazolidinone having a melting point of about 132° C., from 14.7 g. of 2,4,6-trifluoroaniline, 11 g. of 3-pyridinecarboxaldehyde and 4 g. of thiolactic acid. Wt. 2.3 g. Identified by NMR spectrum.

EXAMPLE 65

3-(4-Chlorophenyl)-5,5-dimethyl-2-(3-pyridyl)-4-thiazolidinone

To 150 ml. of anhydrous tetrahydrofuran cooled to −70° C., under an atmosphere of dry nitrogen, there was added 25 ml. of a hexane solution of n-butyllithium all in one portion. The mixture was again cooled to −70° C., and a solution of 15 g. of 3-(4-chlorophenyl)-5-methyl-2-(3-pyridyl)-4-thiazolidinone (prepared as in Example 1, supra) in 100 ml. of anhydrous tetrahydrofuran was added dropwise with stirring. Approximately 0.5 hour after the addition was complete, 14 g. of methyl iodide was added to the mixture dropwise with continued stirring and then the reaction mixture was stirred overnight and allowed to gradually warm to room temperature.

The reaction was worked up by adding water and extracting with ether. The ether layer was dryed over anhydrous magnesium sulfate, the drying agent filtered off and the filtrate concentrated in vacuo to leave a residual oil. The oil was crystallized using a mixture of petroleum ether (boiling point 60°–70° C.) and ethyl ether. A product was obtained having a melting point of about 140°–141° C., which product was identified as 3-(4-chlorophenyl)-5,5-dimethyl-2-(3-pyridyl)-4-thiazolidinone. Wt. 4.8 g. This product was identified by elemental analyses and NMR spectrum.

Analyses calculated for $C_{16}H_{15}ClN_2OS$:

|   | Theoretical | Found |
|---|---|---|
| C | 60.28 | 60.07 |
| H | 4.74 | 4.67 |
| N | 8.79 | 8.52 |

Following the same general procedure of Example 65, the following additional compounds were prepared and identified. The compounds, together with the principal starting materials and weights thereof used in the preparations, are listed in the examples set forth hereinafter.

EXAMPLE 66

5-Butyl-3-(4-chlorophenyl)-5-methyl-2-(3-pyridyl)-4-thiazolidinone, having a melting point of about 76°–77° C., from 15 g. of 3-(4-chlorophenyl)-5-methyl-2-(3-pyridyl)-4-thiazolidinone (from Example 1, supra), 25 ml. of a hexane solution of n-butyllithium, and 9 g. of n-butyl iodide. Wt. 2 g.

Analyses calculated for $C_{19}H_{21}ClN_2OS$:

|   | Theoretical | Found |
|---|---|---|
| C | 63.23 | 63.03 |
| H | 5.87 | 5.66 |
| N | 7.76 | 8.03 |

EXAMPLE 67

3-(4-Chlorophenyl)-5-methyl-5-propyl-2-(3-pyridyl)-4-thiazolidinone, having a melting point of about 81°–83° C., from 15.2 g. of 3-(4-chlorophenyl)-5-methyl-2-(3-pyridyl)-4-thiazolidinone (prepared as in Example 1, supra), 8.5 g. of n-propyl iodide, and 23 ml. of a hexane solution of n-butyllithium. Wt. 1.6 g.

Analyses calculated for $C_{18}H_{19}ClN_2OS$:

|   | Theoretical | Found |
|---|---|---|
| C | 62.33 | 62.55 |
| H | 5.52 | 5.28 |
| N | 8.08 | 8.13 |

EXAMPLE 68

3-(4-Chlorophenyl)-5-hexyl-5-methyl-2-(3-pyridyl)-4-thiazolidinone, having a melting point of about 82°–83° C., from 15.2 g. of 3-(4-chlorophenyl)-5-methyl-2-(3-pyridyl)-4-thiazolidinone (prepared as in Example 1, supra), 10.5 g. of n-hexyl iodide, and 23 ml. of a hexane solution of n-butyllithium. Wt. 1.5 g.

Analyses calculated for $C_{21}H_{25}ClN_2OS$:

|   | Theoretical | Found |
|---|---|---|
| C | 64.85 | 64.59 |
| H | 6.48 | 6.23 |
| N | 7.20 | 7.19 |

EXAMPLE 69

5-Butyl-3-(4-chlorophenyl)-2-(3-pyridyl)-4-thiazolidinone, having a melting point of about 93°–94° C. from 13 g. of 3-(4-chlorophenyl)-2-(3-pyridyl)-4-thiazolidinone (prepared as in Example 19, supra), 9.2 g. of n-butyl iodide, and 25 ml. of a hexane solution of n-butyllithium. Wt. 700 mg.

Analyses calculated for $C_{18}H_{19}ClN_2OS$:

|   | Theoretical | Found |
|---|---|---|
| C | 62.33 | 62.11 |
| H | 5.52 | 5.28 |
| N | 8.08 | 8.08 |

EXAMPLE 70

3-(4-(Chlorophenyl,tetrahydro-2-(3-pyridyl)-4H-1,3-thiazin-4-one

This compound was prepared stepwise as follows.

Step 1.

A mixture of 53.5 g. of 3-pyridylcarboxaldehyde, 63.5 g. of 4-chloroaniline, and 600 ml. of toluene was refluxed for about 4 hours, using a Dean-Stark trap to collect the water given off by the reaction. A total of about 9 ml. of water was collected. The reaction product mixture was cooled, filtered, and the filtrate concentrated to dryness in vacuo. The residue was recrystallized from hot ethyl ether to yield 87 g. of product having a melting point of about 72° C., and identified as 3-[(4-chlorophenylimino)methyl]pyridine.

Step 2.

A mixture was prepared of 15 g. of 3-[(4-chlorophenylimino)methyl]pyridine (prepared above), 15 g. of β-mercaptopropionic acid, and 200 ml. of toluene, and allowed to stand overnight at ambient room temperature. The reaction mixture was concentrated in vacuo to yield a yellow oil, identified as 3-[α-(4-chloroanilino)-α-(3-pyridyl)methylthio]propionic acid. A portion of the yellow oil was used in the next step.

Step 3.

A mixture of 6 g. of the addition product from step 2, supra, 6 g. of N,N'-dicyclohexylcarbodiimide, and 100 ml. of methylene chloride was prepared at room temperature. On standing for a period of time, white solids precipitated. The solids were filtered off, and identified as N,N'-dicyclohexylurea. The filtrate was concentrated to dryness in vacuo, and the residue thus obtained was again taken up in methylene chloride, and filtered to remove additional N,N'-dicyclohexylurea. The filtrate was concentrated to dryness in vacuo. The residue remaining was washed with 20 ml. of cold acetone and the white solids filtered off and air dried. The solids had a melting point of about 149°–150° C. The product was identified by NMR spectrum as 3-(4-chlorophenyl)tetrahydro-2-(3-pyridyl)-4H-1,3-thiazin-4-one.

Following the stepwise general procedure of the above Example 70, additional compounds were prepared and identified by NMR spectra and/or elemental analyses. In some examples, better yields were obtained in Step 2 by refluxing the reactants and this is so indicated at the end of those examples. The compounds, together with the principal starting materials and weights or volumes thereof used in the preparations, are listed in the examples set forth hereinafter.

EXAMPLE 71

3-(4-Tolyl)tetrahydro-2-(3-pyridyl)-4H-1,3-thiazin-4-one, having a melting point of about 178°–180° C., from 3.21 g. of 3-pyridylcarboxaldehyde, 3.21 g. of p-toluidine, 3.18 g. of β-mercaptopropionic acid, and 6.18 g. of N,N'-dicyclohexylcarbodiimide. Refluxed overnight. Wt. 1.6 g.

Analyses calculated for $C_{16}H_{16}N_2OS$:

|   | Theoretical | Found |
|---|---|---|
| C | 67.57 | 67.36 |
| H | 5.67 | 5.72 |
| N | 9.85 | 9.56 |
| S | 11.28 | 11.08 |

EXAMPLE 72

3-Cyclohexyltetrahydro-2-(3-pyridyl)-4H-1,3-thiazin-4-one, having a melting point of about 162°–164° C., from 3.21 g. of 3-pyridylcarboxaldehyde, 2.97 g. of cyclohexylamine, 3.18 g. of β-mercaptopropionic acid, and 6.18 g. of N,N'-dicyclohexylcarbodiimide. Refluxed 4 hours. Wt. 3.58 g.

Analyses calculated for $C_{15}H_{20}N_2OS$:

|   | Theoretical | Found |
|---|---|---|
| C | 65.18 | 64.95 |
| H | 7.29 | 6.99 |
| N | 10.14 | 9.92 |
| S | 11.60 | 11.39 |

EXAMPLE 73

3-Hexyltetrahydro-2-(3-pyridyl)-4H-1,3-thiazin-4-one, having a melting point of about 84°–86° C., from 3.21 g. of 3-pyridylcarboxaldehyde, 3.03 g. of hexylamine, 3.18 g. of β-mercaptopropionic acid, and 6.18 g. of N,N'-dicyclohexylcarbodiimide. Refluxed overnight. Wt. 2.36 g.

Analyses calculated for $C_{15}H_{22}N_2OS$:

|   | Theoretical | Found |
|---|---|---|
| C | 64.71 | 64.92 |
| H | 7.97 | 8.03 |

| | Theoretical | Found |
|---|---|---|
| N | 10.06 | 9.77 |
| S | 11.52 | 11.57 |

EXAMPLE 74

3-Cyclopentyltetrahydro-2-(3-pyridyl)-4H-1,3-thiazin-4-one, having a melting point of about 147°–149° C., from 3.21 g. of 3-pyridylcarboxaldehyde, 2.55 g. of cyclopentylamine, 3.18 g. of β-mercaptopropionic acid, and 6.18 g. of N,N'-dicyclohexylcarbodiimide. Refluxed overnight. Wt. 1.38 g. The compound was identified by NMR spectrum.

EXAMPLE 75

3-(3,4-Dichlorophenyl)tetrahydro-2-(3-pyridyl)-4H-1,3-thiazin-4-one, having a melting point of about 157°–159° C., from 3.21 g. of 3-pyridylcarboxaldehyde, 4.86 g. of 3,4-dichloroaniline, 3.18 g. of β-mercaptopropionic acid, and 6.18 g. of N,N'-dicyclohexylcarbodiimide. Refluxed overnight. Wt. 6.5 g. The compound was identified by NMR spectrum.

EXAMPLE 76

3-(2-Chlorophenyl)tetrahydro-2-(3-pyridyl)-4H-1,3-thiazin-4-one, having a melting point of about 111°–113° C., from 9.63 g. of 3-pyridylcarboxaldehyde, 11.49 g. of 2-chloroaniline, 9.55 g. of β-mercaptopropionic acid, and 18.57 g. of N,N'-dicyclohexylcarbodiimide. Refluxed overnight. Wt. 6.0 g.

Analyses calculated for $C_{15}H_{13}ClN_2OS$:

| | Theoretical | Found |
|---|---|---|
| C | 59.11 | 59.31 |
| H | 4.30 | 4.22 |
| N | 9.19 | 9.34 |
| S | 10.52 | 10.73 |

EXAMPLE 77

3-(4-Chlorobenzyl)tetrahydro-2-(3-pyridyl)-4H-1,3-thiazin-4-one, having a melting point of about 88°–90° C., from 6.42 g. of 3-pyridylcarboxaldehyde, 8.50 g. of 4-chlorobenzylamine, 6.4 g. of β-mercaptopropionic acid, and 12.37 g. of N,N'-dicyclohexylcarbodiimide. Refluxed 6 hours. Wt. 3.1 g.

Analyses calculated for $C_{16}H_{15}ClN_2OS$:

| | Theoretical | Found |
|---|---|---|
| C | 60.28 | 60.50 |
| H | 4.74 | 4.89 |
| N | 8.79 | 8.66 |
| S | 10.06 | 9.79 |

EXAMPLE 78

3-(4-Fluorophenyl)tetrahydro-2-(3-pyridyl)-4H-1,3-thiazin-4-one, having a melting point of about 162°–164° C., from 6.43 g of 3-pyridylcarboxaldehyde, 6.67 g. of 4-fluoroaniline, 6.37 g. of β-mercaptopropionic acid, and 12.4 g. of N,N'-dicyclohexylcarbodiimide. Refluxed overnight. Wt. 6.6 g.

Analyses calculated for $C_{15}H_{13}FN_2OS$:

| | Theoretical | Found |
|---|---|---|
| C | 62.48 | 62.29 |
| H | 4.54 | 4.66 |
| N | 9.72 | 9.91 |
| S | 11.12 | 10.91 |

EXAMPLE 79

Tetrahydro-2-(3-pyridyl)-3-[4-(trifluoromethyl)phenyl]-4H-1,3-thiazin-4-one, having a melting point of about 131°–133° C., from 6.43 g. of 3-pyridylcarboxaldehyde, 9.66 g. of 4-trifluoromethylaniline, 6.37 g. of β-mercaptopropionic acid, and 12.4 g. of N,N'-dicyclohexylcarbodiimide. Refluxed overnight. Wt. 10.6 g.

Analyses calculated for $C_{16}H_{13}F_3N_2OS$:

| | Theoretical | Found |
|---|---|---|
| C | 56.80 | 56.62 |
| H | 3.87 | 3.76 |
| N | 8.28 | 8.31 |
| S | 9.48 | 9.40 |

EXAMPLE 80

3-(2-Cyclopentyl-1-methylethyl)tetrahydro-2-(3-pyridyl)-4H-1,3-thiazin-4-one, having a melting point of about 100°–112° C., from 6.43 g. of 3-pyridylcarboxaldehyde, 7.63 g. of 2-cyclopentyl-1-methylethylamine, 6.37 g. of β-mercaptopropionic acid, and 12.4 g. of N,N'-dicyclohexylcarbodiimide. Refluxed overnight. Wt. 2.55 g.

Analysis calculated for $C_{17}H_{24}N_2OS$:

| | Theoretical | Found |
|---|---|---|
| C | 67.07 | 66.77 |
| H | 7.95 | 8.05 |
| N | 9.20 | 9.26 |
| S | 10.53 | 10.55 |

EXAMPLE 81

3-(3,4-Xylyl)tetrahydro-2-(3-pyridyl)-4H-1,3-thiazin-4-one, having a melting point of about 185°–188° C., from 6.43 g. of 3-pyridylcarboxaldehyde, 7.27 g. of 3,4-dimethylaniline, 6.37 g. of β-mercaptopropionic acid, and 12.4 g. of N,N'-dicyclohexylcarbodiimide. Refluxed overnight. Wt. 8.75 g.

Analyses calculated for $C_{17}H_{18}N_2OS$:

| | Theoretical | Found |
|---|---|---|
| C | 68.43 | 68.66 |
| H | 6.08 | 6.26 |
| N | 9.39 | 9.62 |
| S | 10.75 | 10.56 |

EXAMPLE 82

3-(4-Methylthiophenyl)tetrahydro-2-(3-pyridyl)-4H-1,3-thiazin-4-one, having a melting point of about 164°–166° C., from 6.43 g. of 3-pyridylcarboxaldehyde, 4-methylthioaniline (obtained from 10.54 g. of 4-methylthioaniline hydrochloride), 6.37 g. of β-mercaptopropionic acid, and 8.25 g. of N,N'-dicyclohexylcarbodiimide. Refluxed overnight. Wt. 5.72 g.

Analyses calculated for $C_{16}H_{16}N_2OS_2$:

|   | Theoretical | Found |
|---|---|---|
| C | 60.76 | 60.68 |
| H | 5.06 | 5.18 |
| N | 8.86 | 8.64 |
| S | 20.25 | 20.34 |

EXAMPLE 83

3-(2-Fluorophenyl)tetrahydro-2-(3-pyridyl)-4H-1,3-thiazin-4-one, having a melting point of about 147°–149° C., from 6.43 g. of 3-pyridylcarboxaldehyde, 6.67 g. of 2-fluoroaniline, 6.37 g. of β-mercaptopropionic acid, and 12.4 g. of N,N'-dicyclohexylcarbodiimide. Refluxed overnight. Wt. 6.93 g.

EXAMPLE 83A 3-(2-6-difluorophenyl)tetrahydro-2-(3-pyridinyl)-4H-1,3-thiazin-4-one, having a melting point of about 117° C., from 13 g. of 2,6-difluoroaniline, 11 g. of pyridinecarboxaldehyde, 8 g. of β-mercaptopropionic acid and 11 g. of N,N-dicyclohexylcarbodiimide. Identified by NMR spectrum.

Analyses calculated for $C_{15}H_{12}F_2N_2OS$

|   | Theoretical | Found |
|---|---|---|
| C | 60.76 | 60.68 |
| H | 5.06 | 5.18 |
| N | 8.86 | 8.64 |
| S | 20.25 | 20.34 |

EXAMPLE 84

3-(2-Methoxyphenyl)-2-(3-pyridyl)-4-thiazolidinone

This compound was prepared stepwise.
Step 1.

A mixture of 17 g. of o-anisidine, 15 g. of 3-pyridylcarboxaldehyde, and 13 g. of thioglycolic acid in toluene was refluxed for several hours. The reaction product mixture was cooled and the material which had precipitated was collected on a filter. The product weighed 20 g., had a melting point of about 118°–120° C., and was identified by NMR and IR spectra as [[(o-methoxyanilino)(3-pyridyl)methyl]thio]acetic acid.

Step 2.

A mixture of 5 g. of [[(o-methoxyanilino)(3-pyridyl)methyl]thio]acetic acid, 3.4 g. of N,N'-dicyclohexylcarbodiimide, and 300 ml. of toluene was refluxed for several hours. The toluene was then removed in vacuo. The residue thereby obtained was chromatographed over a silica gel/toluene column and eluted with a mixture of acetone/toluene. The desired fraction was concentrated and the residue recrystallized from a mixture of ether and pentane to yield product having a melting point of about 104°–105° C., and identified as 3-(2-methoxyphenyl)-2-(3-pyridyl)-4-thiazolidinone. Wt. 1.5 g.

Analyses calculated for $C_{15}H_{14}N_2S$:

|   | Theoretical | Found |
|---|---|---|
| C | 61.29 | 61.47 |
| H | 5.14 | 4.86 |
| N | 10.21 | 9.97 |

EXAMPLE 85

3-(4-Chlorophenyl)tetrahydro-5-methyl-2-(3-pyridyl)-4H-1,3-thiazin-4-one 3-(4-Chlorophenyl)tetrahydro-2-(3-pyridyl)-4H-1,3-thiazin-4-one, 3.05 g. (0.01 mole), prepared as described in Example 70, supra, was added with mechanical stirring to 40 ml. of anhydrous tetrahydrofuran maintained under a nitrogen atmosphere and then cooled to about −75° C. To the cold solution there was added, over a period of about 15–20 minutes, 4.28 ml. of a hexane solution of n-butyllithium (2.4 molar in hexane), while maintaining the reaction temperature below −70° C. After the addition was complete, the reaction mixture was stirred for about 30 minutes at a temperature of about −75° C., followed by the dropwise addition of 5 ml. of methyl iodide over a period of about 10–15 minutes. The reaction product mixture was stirred overnight while being cooled in a dry ice-acetone bath, warming gradually to about 0° C., by morning. A peach-colored solid precipitated during the night. The reaction product mixture was warmed to room temperature and methylene chloride added, forming a red solution. The solution was concentrated in vacuo. The residue thus obtained was redissolved in methylene chloride and the solution was washed twice with cold salt water and dried over anhydrous sodium sulfate. The drying agent was filtered off and the filtrate concentrated in vacuo to leave a residue. The residue was taken up in ethyl acetate and passed through a layer of silica gel (400 ml.). The ethyl acetate solution so treated was concentrated in vacuo, and the oil which remained was dissolved in methylene chloride, treated with decolorizing carbon, filtered, and the filtrate concentrated to dryness in vacuo. The residue thus obtained was dissolved in ethyl ether, and, upon cooling, a solid crystallized, and was filtered off. The solid had a melting point of about 128°–130° C., and weighed 1.1 g. The solid was identified by NMR spectrum and elemental analyses as 3-(4-chlorophenyl)tetrahydro-5-methyl-2-(3-pyridyl)-4H-1,3-thiazin-4-one.

Analyses calculated for $C_{16}H_{15}ClN_2OS$:

|   | Theoretical | Found |
|---|---|---|
| C | 60.28 | 60.46 |
| H | 4.74 | 4.65 |
| N | 8.79 | 8.77 |
| S | 10.06 | 9.94 |

Following the general procedure of Example 85, the following additional compound was prepared and identified.

EXAMPLE 86

3-(4-Chlorophenyl)tetrahydro-5,5-dimethyl-2-(3-pyridyl)-4H-1,3-thiazin-4-one, having a melting point of about 126°–128° C., and weighing 2.60 g., from 4 g. of 3-(4-chlorophenyl)tetrahydro-5-methyl-2-(3-pyridyl)-4H-1,3-thiazin-4-one (from Example 85), 8 ml. of methyl iodide, and 5.4 ml. of a 2.4 M hexane solution of n-butyllithium. Identified by NMR spectrum and elemental analyses.

Analyses calculated for $C_{17}H_{17}ClN_2OS$:

|   | Theoretical | Found |
|---|---|---|
| C | 61.34 | 61.15 |

| | Theoretical | Found |
|---|---|---|
| H | 5.15 | 4.95 |
| N | 8.42 | 8.47 |
| S | 9.63 | 9.53 |

EXAMPLE 87

5-Methyl-2-(3-pyridyl)-3-(3-trifluoromethylthiophenyl)-4-thiazolidinone

This compound was prepared step wise.
Step 1.

A mixture of 15 g. of trifluoromethylthio-3-nitrobenzene in 100 ml. of absolute methanol was hydrogenated in the presence of Raney nickel catalyst, using a Parr hydrogenation apparatus. When hydrogen uptake had ceased, the reaction was stopped, the catalyst filtered off, and the filtrate concentrated to yield product weighing 12 g. and identified by NMR spectrum as trifluoromethylthio-3-aminobenzene.
Step 2.

A mixture of 11 g. of trifluoromethylthio-3-aminobenzene, 7.7 g. of 3-pyridylcarboxaldehyde and 200 ml. of toluene was refluxed for about 2 hours using a Dean-Stark trap to collect the water produced by the reaction. A total of 1.2 ml. of water was isolated. The reaction product mixture was cooled and concentrated in vacuo. The residual oil was dissolved in toluene and chromatographed on a silica column. The material was eluted using toluene-5% acetone eluant, the several fractions from the column being checked for their content by thin layer chromatography. The appropriate fractions were then combined and concentrated to leave a residual oil. The isolated material, a yellow oil weighing 15 g., was identified by NMR spectrum as 3-(3-trifluoromethylthio)-N-(3-pyridylmethylene)benzenamine. The material was used without further purification in the next step of the reaction.
Step 3.

A mixture of 14 g. of 3-(3-trifluoromethylthio)-N-(3-pyridylmethylene)benzenamine, 8 g. of thiolactic acid, and 200 ml. of toluene was refluxed for about 6 hours, using a Dean-Stark trap to collect the water produced by the reaction. The reaction product mixture was then concentrated in vacuo and the residue thereby obtained was dissolved in toluene and chromatographed on a silica column. The product was eluted from the column using 5% acetone-toluene, and the fractions concentrated to leave a yellow oil weighing 6 g. It was identified by NMR spectrum as 5-methyl-2-(3-pyridyl)-3-(3-trifluoromethylthiophenyl)-4-thiazolidinone.

EXAMPLE 88

3-(4-Chlorophenyl)-2-(3-pyridyl)-4-thiazolidinone hydrochloride

A solution of 1.5 g. of 3-(4-chlorophenyl)-2-(3-pyridyl)-4-thiazolidinone (Example 19, supra) in ethyl ether was prepared, cooled, and saturated with anhydrous hydrogen chloride. The solid material which precipitated was filtered off and identified by NMR spectrum as 3-(4-chlorophenyl)-2-(3-pyridyl)-4-thiazolidinone hydrochloride.

EXAMPLE 88A 3-(4-Chlorophenyl)-5-methyl-2-(3-pyridyl)-4-thiazolidinone hydrochloride A solution of 4 g. of 3-(4-chlorophenyl)-5-methyl-2-(3-pyridyl)-4-thiazolidinone (Example 1, supra) in ethyl ether was prepared, filtered and saturated with anhydrous hydrogen chloride. The solid material which precipitated was filtered off and identified by NMR spectrum as 3-(4-chlorophenyl)-5-methyl-2-(3-pyridyl)-4-thiazolidinone hydrochloride. The melting point of the product was about 135° C.

EXAMPLE 88B

3-Cyclohexyl-5-methyl-2-(3-pyridyl)-4-thiazolidinone hydrochloride

A solution of 3-cyclohexyl-5-methyl-2-(3-pyridyl)-4-thiazolidinone (Example 29, supra) in ethyl ether was prepared and saturated with anhydrous hydrogen chloride. The solid material which precipitated was filtered off and dried under vacuum. The product had a melting point of about 120°-125° C. and was identified by NMR spectrum as 3-cyclohexyl-5-methyl-2-(3-pyridyl)-4-thiazolidinone hydrochloride.

EXAMPLE 88C 3-(2-Fluorophenyl)-5-methyl-2-(3-pyridyl)-4-thiazolidinone hydrochloride A solution of 3-(2-fluorophenyl)-5-methyl-2-(3-pyridyl)-4-thiazolidinone (Example 35, supra) in ethyl ether was prepared and saturated with anhydrous hydrogen chloride. The solid material which precipitated was removed by filtration and air dried. The product had a melting point of about 112° C. and was identified by NMR spectrum as 3-(2-fluorophenyl)-5-methyl-2-(3-pyridyl-4-thiazolidinone hydrochloride.

EXAMPLE 89A 3-(4-Chlorophenyl)-5-(methylthio)-2-(3-pyridyl)-4-thiazolidinone and

EXAMPLE 89B 3-(4-Chlorophenyl)-5,5-bis(methylthio)-2-(3-pyridyl)-4-thiazolidinone A mixture of 10.1 g. of diisopropylamine and 500 ml. of tetrahydrofuran was cooled to a temperature of about 0° C. under a nitrogen atmosphere. There was added to the mixture 45 ml. of a hexane solution of n-butyllithium dropwise, with stirring, and the stirring was continued for about 30 minutes after addition was complete. The mixture was then cooled to about −70° C., and a solution of 14.5 g. of 3-(4-chlorophenyl)-2-(3-pyridyl)-4-thiazolidinone (Example 19, supra) in 100 ml. of tetrahydrofuran was added dropwise. Thirty minutes after this addition was completed, 9.4 g. of methyldisulfide was added. The reaction mixture was stirred overnight and allowed to gradually warm to ambient room temperature. The reaction mixture was worked up by adding water dropwise, at about room temperature. The organic phase was then extracted with methylene chloride. The methylene chloride layer was washed with dilute aqueous hydrochloric acid. The methylene chloride layer was separated and dried over anhydrous sodium sulfate. The drying agent was filtered off and the filtrate concentrated in vacuo to leave a residual oil.

The oil was dissolved in toluene and chromatographed over silica gel. Elution was accomplished with toluene: 10% acetone, and a separation was effected so that there was obtained, after concentrating the fractions, a product having a melting point of about 104°–106° C., and weighing 1 g., identified by NMR spectrum and elemental analyses as 3-(4-chlorophenyl)-5-(methylthio)-2-(3-pyridyl)-4-thiazolidinone.

Analyses calculated for $C_{15}H_{13}ClN_2OS_2$:

|   | Theoretical | Found |
|---|---|---|
| C | 53.48 | 53.40 |
| H | 3.89 | 3.91 |
| N | 8.32 | 8.20 |

A second product having a melting point of about 133°–135° C., and weighing 400 mg. was isolated in the same manner and identified by NMR spectrum and elemental analyses as 3-(4-chlorophenyl)-5,5-bis-(methylthio)-2-(3-pyridyl)-4-thiazolidinone.

Analyses calculated for $C_{16}H_{15}ClN_2OS_3$:

|   | Theoretical | Found |
|---|---|---|
| C | 50.18 | 50.09 |
| H | 3.95 | 3.91 |
| N | 7.32 | 7.08 |

EXAMPLE 90

3-(4-Chlorophenyl)tetrahydro-2-(3-pyridyl)-4H-1,3-thiazin-4-thione

A suspension was prepared of 10 g. (0.033 moles) of 3-(4-chlorophenyl)tetrahydro-2-(3-pyridyl)-4H-1,3-thiazin-4-one (prepared in Example 70, supra) in 30 ml. of dry pyridine, and with mechanical stirring the mixture was heated to about 90° C., forming a solution. To the solution thus formed, and with continued stirring, there was added 1.78 g. (0.008 moles) of phosphorous pentasulfide portionwise over a period of about 10–15 minutes. The solution turned orange in color. After the addition was completed, the reaction mixture was stirred overnight at a temperature of about 90° C. The then red-colored solution was cooled and the pyridine solvent evaporated in vacuo. The viscous oily residue was washed by triturating it with water. The oil was then taken up in a mixture of dimethylformamide and ethanol, decolorized with carbon, filtered, and the ethanol evaporated in vacuo. The dimethylformamide solution was poured slowly into cold water, whereby a crude orange solid precipitated. The solid was extracted from the aqueous mixture with ethyl acetate. The extract was washed with cold aqueous sodium chloride solution and the ethyl acetate solution concentrated in vacuo to yield a dark red oil. The oil was taken up in a minimum volume of ethyl acetate and chromatographed over a silica gel column. There was obtained a red viscous oil which was crystallized from a mixture of ethyl acetate and ether to yield a yellow solid, having a melting point of about 115°–117° C., and weighing 3.91 g. The product was identified by elemental analyses as 3-(4-chlorophenyl)tetrahydro-2-(3-pyridyl)-4H-1,3-thiazin-4-thione.

Analyses calculated for $C_{15}H_{13}ClN_2S_2$:

|   | Theoretical | Found |
|---|---|---|
| C | 56.15 | 56.10 |
| H | 4.08 | 4.22 |
| N | 8.73 | 8.58 |
| S | 19.99 | 19.94 |

One embodiment of this invention is practiced by adding the active substituted 1-thia-3-aza-4-one compounds to the water containing the submerged or floating aquatic weeds. The compounds may be applied to the water as dusts when admixed with a powdered solid carrier such as bentonite, Fuller's earth, diatomaceous earth, or various mineral silicates, e.g., mica, talc, pyrophyllite, and clays. The compounds may also be mixed with surface-active dispersing agents to form concentrates to facilitate dispersion in water and to improve the wetting properties when used as sprays. If desired, the compounds may be mixed with a powdered solid carrier, together with a surface-active dispersing agent, so that a wettable powder may be obtained which may be applied directly, or which may be shaken with water to make an aqueous dispersion for application in that form. These wettable powder formulations suitably contain from about 25 to about 85 percent by weight of the active ingredient, i.e., an aquatic growth regulating compound coming within the scope of the generic formulae, supra. The compounds may be dissolved in an oil, such as a hydrocarbon or chlorinated hydrocarbon oil, and the oil solution of the compound dispersed in water with the aid of a surface-active dispersing agent to give a sprayable aqueous dispersion. Such surface-active dispersing agents may be anionic, nonionic, or cationic surface-active agents. Such surface-active agents are well-known, and reference is made to Hoffman et al., U.S. Pat. No. 2,614,916, columns 2–4, for detailed examples of the same. The compounds useful in this embodiment of the invention may also be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

Further, the compounds useful as aquatic growth regulators can also be applied in an invert emulsion formulation. An invert emulsion formulation is prepared by first making a solution of an aquatic growth regulating compound in heavy oils, such as diesel fuel, inverting oil, and the like, and combining the thus-obtained solution with water under high shear stirring. The thick emulsion is placed in the water and sinks to the bottom of the lake, river, pond, or the like, and the aquatic growth regulator is gradually released to control the growth of the aquatic plants. The following is an example of an invert emulsion formulation, prepared using Compound 1 of this application.

| Invert Emulsion | |
|---|---|
| Compound 1 | 12.5 gm |
| Diesel fuel | 333 ml |
| Inverting oil* | 333 ml |

*Vioko-Rhap Inverting Oil (Rhodia, Inc.)

This solution, 250 ml., is combined with 3750 ml. of water under high shear stirring to give a thick invert emulsion.

The compounds useful as aquatic growth regulators can also be applied as pellets which are prepared from a mixture of about 5% of the active ingredient, in this case a substituted 1-thia-3-aza-4-one, 85% clay, and 10% water, all percentages being by weight. The mixture is then extruded through a pellet mill using a suitably sized die, e.g., about ⅛ in. diameter. The extruded pellets are about ⅛ in. by 1½ in., and are then dried to about 8% moisture content.

This embodiment of the invention is practiced by adding to the water containing the submerged and floating weeds a growth-regulating and non-herbicidal amount of one of the herein-disclosed compounds, such that a concentration of from about 0.25 to about 10 ppm. of the active compound is attained.

The optimum concentration of active compound for any specific aquatic weed control problem varies with the temperature, the species to be controlled, and the shape of the body of water to be treated. At higher water temperatures, less compound is generally required for a given degree of control than is needed at lower temperatures.

In considering the treatment of moving streams for the purpose of controlling flora fixed therein, special account must be taken of the fact that the compounds will pass over the area to be treated and that the concentration during the contact period is dependent upon the water flow rate, the rate of chemical addition, and the period of addition.

The novel aquatic growth regulating method and compositions for use therein are illustrated by the following experiments.

Trial 1

The following method was used in the laboratory to evaluate the aquatic growth regulating properties of the compounds disclosed herein, when used at a concentration of 10 ppm., against a representative submerged aquatic weed.

The compounds for this test were formulated in the following manner. Twenty mg. of compound was weighed into a 12 ml. disposable vial. To the vial containing the compound were added 1 ml. of acetone and 9 ml. of aqueous 0.1 percent polyoxyethylene sorbitan monooleate (Tween 80). To obtain the test concentration of 10 ppm., 4.00 ml. of this stock solution was added to 785 ml. of water in a plastic container. The plastic containers used were flowerpot-shaped, having a bottom diameter of 9 cm., a top diameter of 11.5 cm., and a height of 13.5 cm.

Terminal pieces of Florida elodea, *Hydrilla verticillata* (L.F.), (hereinafter identified as hydrilla) 10 cm. long, without branching, were prepared for testing. Three such cuttings were placed in each plastic container holding 785 ml. of water, to which water the formulated test compound had been added, along with 3 ml. of Hoagland's nutrient solution. Three 10 cm. cuttings of hydrilla were placed in each of several control containers of water. To the water in each control container there was also added the amount of solvent used to formulate the test compound for each container.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC) and the quotient multiplied by 100 to give a percent inhibition.

$$\frac{\text{Total combined length of Replicates}}{\text{Number of Replicates}} = \text{Average Length}$$

Avg. Length − 10 cm. = Avg. Increased Growth $$\left(1 - \frac{\text{Avg. Increased Growth}}{\text{Avg. Increased Growth } SC}\right) \times 100 = \% \text{ Inhibition}$$

Each compound employed in this experiment, as well as in one or more of the experiments described hereinafter, is identified by the number of the operating example describing its preparation.

The results of the tests, run at a concentration of 10 ppm. of compound, and observed at the end of three weeks, are set forth in Table 1, which follows. In the table, the number in column 1 identifies the test compound; column 2 lists the percent growth inhibition of hydrilla observed.

TABLE 1

Substituted 1-Thia-3-aza-4-one Derivatives

| Compound | Approximate % Growth Inhibition |
|---|---|
| 1 | 91 |
| 2 | 78 |
| 3 | 82 |
| 4 | 93 |
| 5 | 97 |
| 6 | 76 |
| 7 | 61 |
| 8 | 71 |
| 9 | 99 |
| 10 | 73 |
| 11 | 82 |
| 12 | 75 |
| 13 | 64 |
| 14 | 66 |
| 15 | 74 |
| 16 | 57 |
| 17 | 72 |
| 18 | 84 |
| 19 | 89 |
| 20 | 58 |
| 21 | 88 |
| 23 | 93 |
| 24 | 91 |
| 25 | 85 |
| 26 | 69 |
| 27 | 88 |
| 28 | 100 |
| 29 | 90 |
| 30 | 93 |
| 31 | 97 |
| 32 | 81 |
| 33 | 95 |
| 34 | 93 |
| 35 | 55 |
| 36 | 77 |
| 38 | 49 |
| 39 | 96 |
| 40 | 91 |
| 41 | 86 |
| 42 | 77 |
| 43 | 80 |
| 44 | 79 |
| 45 | 85 |
| 46 | 64 |
| 47 | 53 |
| 48 | 95 |

TABLE 1-continued

Substituted 1-Thia-3-aza-4-one Derivatives

| Compound | Approximate % Growth Inhibition |
|---|---|
| 49 | 94 |
| 50 | 81 |
| 51 | 85 |
| 52 | 78 |
| 53 | 60 |
| 55 | 84 |
| 56 | 87 |
| 57 | 93 |
| 58 | 95 |
| 59 | 97 |
| 60 | 96 |
| 61 | 87 |
| 62 | 91 |
| 63 | 71 |
| 64 | 75 |
| 64A | 70 |
| 64B | 77 |
| 64C | 93 |
| 64D | 82 |
| 64E | 84 |
| 64F | 87 |
| 64G | 59 |
| 65 | 96 |
| 66 | 99 |
| 67 | 98 |
| 68 | 95 |
| 69 | 95 |
| 70 | 97 |
| 71 | 95 |
| 72 | 86 |
| 73 | 88 |
| 74 | 74 |
| 75 | 96 |
| 76 | 94 |
| 77 | 91 |
| 78 | 86 |
| 79 | 86 |
| 80 | 97 |
| 81 | 91 |
| 82 | 92 |
| 83 | 94 |
| 83A | 87 |
| 84 | 69 |
| 85 | 93 |
| 86 | 93 |
| 87 | 94 |
| 89A | 89 |
| 89B | 62 |
| 90 | 94 |

Trial 2

The general procedure of Trial 1, again employing *Hydrilla verticillata* (L.F.), was repeated using a number of the same compounds. This time test concentrations of 1, 0.5 and 0.25 ppm. were employed.

The test compounds were formulated in the following manner: Twenty mg. of compound was weighed into a 12 ml. disposable vial. To the vial containing the compound were added 1 ml. of acetone and 9 ml. aqueous 0.1 percent polyoxyethylene sorbitan monooleate. This solution was designated as stock solution A.

The 1 ppm. test concentration was obtained as follows: Four ml. of stock solution A was diluted with 36 ml. of aqueous 0.1 percent polyoxyethylene sorbitan monooleate to give stock solution B. Four ml. of stock solution B, when added to 785 ml. water in the plastic test containers, gave a concentration of test compound of 1 ppm. The plastic test containers were identical to those employed in Trial 1.

The 0.5 ppm. concentration of test compound was obtained as follows: Stock solution B, 20 ml., was diluted with 20 ml. aqueous 0.1 percent polyoxyethylene sorbitan monooleate, and this solution was designated stock solution C. Four ml. of stock solution C was added to 785 ml. of water in the plastic test containers to give a concentration of 0.5 ppm.

The 0.25 ppm. concentration of test compound was obtained as follows: Stock solution C, 20 ml., was diluted with 20 ml. aqueous 0.1 percent polyoxyethylene sorbitan monooleate to give stock solution D. This stock solution D, 4 ml., added to 785 ml. of water in the plastic test containers gave a concentration of test compound of 0.25 ppm.

Three weeks after the date of application of the test compounds, measurements were made on the total growth of each plant, as described in Trial 1, and the percent inhibition observed was calculated using the formulas set forth in Trial 1, above. The results are recorded in Table 2, which follows. The test compounds are each identified by the same number as used in Trial 1.

TABLE 2

Substituted 1-Thia-3-aza-4-one Derivatives

| Compound | Approximate % Growth Inhibition at Indicated Test Concentrations | | |
|---|---|---|---|
| | 1 ppm. | 0.5 ppm. | 0.25 ppm. |
| 1 | 63 | 74 | 73 |
| 2 | 64 | 67 | 65 |
| 3 | 72 | 55 | 56 |
| 5 | 83 | 75 | 54 |
| 6 | 50 | 29 | 37 |
| 9 | 71 | 40 | 34 |
| 18 | 71 | 69 | 73 |
| 19 | 72 | 57 | 32 |
| 21 | 67 | 62 | 61 |
| 23 | 63 | 48 | 45 |
| 24 | 61 | 58 | 62 |
| 29 | 67 | 45 | 50 |
| 31 | 66 | 60 | 52 |
| 33 | 52 | 32 | 11 |
| 35 | 73 | 68 | 64 |
| 36 | 63 | 62 | 63 |
| 40 | 64 | 37 | 21 |
| 48 | 63 | 57 | 53 |
| 49 | 61 | 56 | 45 |
| 51 | 63 | 59 | 60 |
| 52 | 53 | 43 | 18 |
| 56 | 69 | 65 | 70 |
| 57 | 73 | 71 | 70 |
| 58 | 72 | 53 | 31 |
| 59 | 68 | 75 | 72 |
| 64B | 59 | 16 | 17 |
| 65 | 53 | 55 | 59 |
| 67 | 61 | 57 | 51 |
| 68 | 64 | 65 | 39 |
| 70 | 63 | 55 | 40 |
| 76 | 80 | 59 | 54 |
| 77 | 52 | 46 | 27 |
| 81 | 50 | 13 | 22 |
| 89B | 51 | 53 | 55 |

Another embodiment of this invention is practiced by applying to the loci of plant pathogenic fungi, fungicidally-effective amounts of one or more of the compounds of generic formulae IV or V. Thus, the compounds of the present invention are applied in effective amounts, varying somewhat with the severity of the fungus infection and with other factors such as the environment in which the treatment is conducted.

The compositions for use in the present embodiment of this invention desirably contain, in addition to the substituted 1-thia-3-aza-4-one antifungal compound, one or more of a plurality of additaments including water, polyhydroxy compounds, petroleum distillates, and other dispersion media, surface-active dispersing agents, emulsifiers, and finely-divided inert solids. The concentration of the substituted 1-thia-3-aza-4-one antifungal in these compositions may vary depending on whether the composition is intended for a direct application to plants or is intended to be subsequently diluted with additional inert carrier such as water to produce the ultimate treating composition.

Treating compositions are most conveniently formulated by preparing liquid or solid concentrates, which are subsequently diluted to the desired level for use. Emulsifiable liquid concentrates can be prepared by incorporating from about 1 to about 10 percent by weight of the active ingredient and an emulsifiable agent in a suitable water-immiscible organic liquid. Such concentrates may be further diluted with water to form spray mixtures in the form of oil-in-water emulsions. Such spray compositions then comprise active toxicant, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, complex ether alcohols, ionics of the arylalkyl sulfonate type, and the like. Suitable water-immiscible organic liquids to be employed include aromatic hydrocarbons, aliphatic hydrocarbons, cycloaliphatic hydrocarbons, and mixtures thereof such as petroleum distillates.

Solid concentrate mixtures can be prepared by incorporating from about 10 to about 50% by weight of the substituted 1-thia-3-aza-4-one compound in a finely-divided solid carrier such as bentonite, Fuller's earth, diatomaceous earth, hydrated silica, diatomaceous silica, expanded mica, talc, chalk, and the like. Such concentrates can be formulated, if desired, for direct use as dusting compositions, or can be diluted, if desired, with additional inert solid carriers to produce dusting powders containing around 0.05 to 1% by weight of the substituted 1-thia-3-aza-4-one. Alternatively, the surfactants, that is, dispersing and/or wetting agents, can be incorporated along with the substituted 1-thia-3-aza-4-one in the solid carrier to form wettable powder concentrates ranging from about 10 to about 25% by weight concentration, which subsequently can be dispersed in water or other hydroxylated carrier to form spray compositions. Suitable surfactants include condensed aryl sulfonic acids and sodium salts thereof, sodium lignosulfate, sulfonate-oxide condensate blends, alkylaryl polyether alcohols, sulfonate/nonionic blends, anionic wetting agents, and the like.

Further, the substituted 1-thia-3-aza-4-one antifungal can be incorporated in solutions, simple dispersions, aerosol formulations, and other media acceptable to be employed for treating vegetation or applying to the soil.

In operating according to the instant embodiment of the invention, the antifungal composition is applied to infected or susceptible plant surfaces in any convenient fashion such as by spraying, dusting, dipping, or drenching. A spray method is considered preferable, especially when large numbers of plants are involved, because of the rapidity and uniformity of treatment possible. In spraying it is usually sufficient for the infected or susceptible surfaces to be thoroughly wet with the liquid dispersion employed. Good results have been obtained by employing spray compositions whether they be emulsions or aqueous dispersions of solid concentrates.

Where the fungi to be controlled are in the soil, the antifungal compounds can be applied to the soil directly, or they can be diluted with various inert solid or liquid diluents, as described above, and then applied to the fungus-infested area. In one method of application to the soil, the soil surface is sprayed with a liquid dispersion or emulsion of the active ingredient. The application is allowed to remain as a coating on the surface of the soil, or alternatively, incorporated into the soil by disking, hoeing, or other methods well known to those skilled in the art. Another method of application is to apply the active ingredient, in the form of a liquid dispersion or emulsion, to the soil as a drench. Thus, for the control of soil-inhabiting fungi in the greenhouse, the application rate varies from about 5 to about 200 ppm. active ingredient. When an acid addition salt of a 1-thia-3-aza-4-one base is used, the rate of application will, of course, depend on the amount of base actually present, since the acids which form salts with these compounds contribute little or nothing to the fungicidal activity of the base, and the salts themselves are employed chiefly for ease of handling and formulating.

The fungicidally-active compounds of this invention have also been found effective when utilized as a seed soak for seeds prior to planting. Thus, where a fungicidal substituted 1-thia-3-aza-4-one coming within the scope of the generic formula, supra, is applied as a seed soak, a seed soak formulation is prepared containing the fungicidal compound, together with other excipients such as a mixture of ethanolacetone, polyoxyethylene sorbitan monolaurate, and the like.

When such a compound, that is, a 1-thia-3-aza-4-one, is utilized as a seed soak, satisfactory control has been accomplished at an application rate of from about 50 to about 400 ppm. of the fungicidal substituted 1-thia-3-aza-4-one compound. The seeds are allowed to soak in the formulation for a period of up to about 4 hours. The seeds are then removed and planted.

The use of the substituted 1-thia-3-aza-4-one compounds represented by the above formulae, and acid addition salts thereof, as plant fungicidal agents, is illustrated by the following procedures.

Trial 3

The evaluation of the effectiveness as a soil drench of some of the compounds exemplified by the above formulae against *Erysiphe cichoracearum*, the causative organism of cucumber powdery mildew, was accomplished in the greenhouse in the following manner.

Fungicidal compositions were prepared by dissolving the compound to be tested in a 1:1 mixture of ethanol:acetone containing polyoxyethylene sorbitan monolaurate (Tween 20) and diluting with deionized water to a final concentration of 1% solvent and 0.1% surfactant. The most concentrated fungicidal composition was prepared first, that is, the one containing the highest concentration of active ingredient. The other fungicidal compositions containing lower concentrations of the active ingredient were then prepared by serial dilution technique from the highest concentration composition. A solvent-surfactant blank was used as a control.

Five cucumber seeds (*Cucumis sativus* L., variety "Green Prolific") were planted in 4-inch square plastic pots containing soil and covered with sand. After the seeds had sprouted, the plants were thinned to 2 per pot. On day 15 after the seed was planted, 1 pot for each concentration of each test compound was soil drenched with 50 ml. of the formulated test compound. The pots containing the plants were then placed in the greenhouse and the leaves of the plants were inoculated by dusting them with conidia from infested cucumber plants. On day 23 after planting, the plants were observed to determine the incidence of cucumber powdery mildew on the cucumber plants. The results of the tests are recorded in Table 3, which follows. In the table, 0 percent=no powdery mildew incidence (infection).

TABLE 3

| Compound | Appln. Rate ppm | Percent Incidence Powdery Mildew Infection on Cucumber |
|---|---|---|
| 1 | 1 | 40 |
|  | 5 | 5 |
|  | 20 | 0 |
|  | 25 | 0 |
|  | 100 | 0 |
| 2 | 5 | 0 |
|  | 20 | 0 |
|  | 100 | 0 |
| 3 | 1 | 40 |
|  | 5 | 0 |
|  | 10 | 0 |
|  | 20 | 0 |
| 7 | 5 | 70 |
|  | 20 | 20 |
|  | 100 | 0 |
| 8 | 5 | 70 |
|  | 20 | 55 |
|  | 100 | 0 |
| 10 | 5 | 15 |
|  | 20 | 15 |
|  | 100 | 0 |
|  | 200 | 0 |
| 11 | 10 | 60 |
|  | 20 | 50 |
|  | 40 | 0 |
|  | 80 | 0 |
| 12 | 5 | 0 |
|  | 20 | 0 |
|  | 100 | 0 |
|  | 200 | 0 |
| 14 | 5 | 60 |
|  | 20 | 25 |
|  | 100 | 0 |
|  | 200 | 0 |
| 18 | 5 | 15 |
|  | 20 | 0 |
|  | 100 | 0 |
|  | 200 | 0 |
| 19 | 1 | 65 |
|  | 5 | 0–50 |
|  | 10 | 0–5 |
|  | 20 | 0 |
|  | 25 | 0 |
|  | 40 | 0 |
|  | 80 | 0 |
|  | 100 | 0 |
| 22 | 5 | 80 |
|  | 20 | 75 |
|  | 100 | 20 |
|  | 200 | 2 |
| 23 | 20 | 10 |
|  | 100 | 0 |
| 24 | 1 | 5 |
|  | 5 | 0 |
|  | 10 | 0 |
| 25 | 20 | 60 |
|  | 100 | 0 |
| 26 | 20 | 65 |
|  | 100 | 0 |
| 27 | 20 | 50 |
|  | 100 | 0 |
| 37 | 5 | 80 |
|  | 20 | 70 |
|  | 100 | 0 |
|  | 200 | 0 |

TABLE 3-continued

| Compound | Appln. Rate ppm | Percent Incidence Powdery Mildew Infection on Cucumber |
|---|---|---|
| 54 | 5 | 80 |
|  | 20 | 20 |
|  | 100 | 0 |
|  | 200 | 0 |
| 88 | 5 | 45 |
|  | 20 | 0 |
|  | 100 | 0 |
| 89A | 20 | 0 |
|  | 200 | 0 |
| Control | 0 | 70–95 |

Trial 4

A test to establish the efficacy of selected compounds of the above formulae as fungicides in the control of *Erysiphe graminis tritici*, the causative organism of powdery mildew of wheat, was carried out in the greenhouse in the following manner.

Fungicidal compositions were prepared in the same manner as described in Experiment 3, supra.

Thirty to forty wheat seeds (variety Monon) were planted in 4-inch square plastic pots containing soil and covered with sand. After about 6 to 8 days, when the seedlings are 4–6 inches tall, 1 pot for each concentration of each test compound was soil drenched with a volume of the formulated test chemical. The plants were then placed in the greenhouse and the leaves were inoculated by dusting them with conidia from infested wheat plants. About 14 to 16 days after planting the plants were observed to determine the percent incidence of the wheat powdery mildew on the wheat plants. The results are recorded in Table 4, which follows. In the table, 0 percent=no powdery mildew incidence (infection).

TABLE 4

| Compound | Appln. Rate ppm | Percent Incidence Powdery Mildew on Wheat |
|---|---|---|
| 1 | 1 | 60 |
|  | 5 | 20 |
|  | 20 | 0 |
|  | 25 | 0 |
|  | 100 | 0 |
| 10 | 5 | 60 |
|  | 20 | 25 |
|  | 100 | 0 |
|  | 200 | 0 |
| 11 | 5 | 60 |
|  | 20 | 45 |
|  | 100 | 0 |
| 12 | 5 | 40 |
|  | 20 | 0 |
|  | 100 | 0 |
|  | 200 | 0 |
| 17 | 5 | 60 |
|  | 20 | 55 |
|  | 100 | 5 |
|  | 200 | 0 |
| 18 | 5 | 70 |
|  | 20 | 65 |
|  | 100 | 5 |
|  | 200 | 5 |
| 19 | 1 | 60 |
|  | 5 | 25 |
|  | 10 | 0 |
|  | 20 | 0 |
|  | 25 | 0 |
|  | 40 | 0 |
| 37 | 5 | 70 |
|  | 20 | 70 |

TABLE 4-continued

| Compound | Appln. Rate ppm | Percent Incidence Powdery Mildew on Wheat |
|---|---|---|
|  | 100 | 10 |
|  | 200 | 5 |
| Control | 0 | 60-80 |

Trial 5

The evaluation of the effectiveness of some of the compounds exemplified by the above formulae against *Erysiphe graminis hordei*, the causative organism of powdery mildew of barley, was accomplished in the greenhouse in the same manner as that described in Experiment 4. The results are recorded in Table 5, which follows.

TABLE 5

| Compound | Appln. Rate ppm | Percent Incidence Powdery Mildew on Barley |
|---|---|---|
| 2 | 5 | 0 |
|  | 20 | 0 |
|  | 40 | 0 |
|  | 80 | 0 |
|  | 100 | 0 |
| 3 | 20 | 0 |
|  | 40 | 0 |
|  | 80 | 0 |
| 19 | 5 | 60 |
|  | 20 | 20 |
|  | 100 | 0 |
| 24 | 20 | 0 |
|  | 40 | 0 |
|  | 80 | 0 |
| 88 | 0.295 | 60 |
|  | 1.18 | 15 |
|  | 5.90 | 0 |
| Control | 0 | 60-75 |

Trial 6

The further evaluation of the effectiveness of some of the compounds exemplified by the above formulae against the powdery mildew disease of barley was carried out in the greenhouse in the following manner.

Fungicidal compositions were prepared by dissolving the compound to be tested in 2% ethanol:acetone (1:1) plus 0.1% polyoxyethylene sorbitan monolaurate in deionized water. Each test compound was prepared in concentrations of 200, 400 and 800 ppm. Five milliliters of each concentration was sprayed onto 3 cups of soil being tumbled in a tumbler to thoroughly incorporate the compound. This resulted in rates of 1, 2 and 4 mg/3 cups of soil, respectively. In plastic pots measuring 20.32 cm. in diameter and 25.4 cm. in depth, there was placed 5 cups of untreated greenhouse soil. The 3 cups of treated soil was used to fill the top 6 cm. of each pot. Twenty seeds of Larker variety barley were planted in the treated soil at a depth of 1 cm. The pots were top watered as needed. When the plants were 6 days old, all the plants were inoculated with powdery mildew conidia from infected plants.

Beginning 12 days after planting (DAP), the barley plants were observed for the incidence of powdery mildew. The observed results were recorded and are shown in Table 6, which follows. In the table, 0%=no powdery mildew incidence and thus 100% control.

TABLE 6

| Compound | Appln. rate kg./ha. | Powdery Mildew Incidence On Barley at DAP | | | |
|---|---|---|---|---|---|
|  |  | 12 | 15 | 19 | 25 |
| 2 | 0.28 | 0 | 0 | 2 | 10 |
|  | 0.56 | 0 | 0 | 0 | 2 |
|  | 1.12 | 0 | 0 | 0 | 2 |
| 3 | 0.28 | 50 | 60 | 70 | 75 |
|  | 0.56 | 5 | 10 | 20 | 30 |
|  | 1.12 | 0 | 2 | 10 | 20 |
| 12 | 0.28 | 60 | 75 | 80 | 85 |
|  | 0.56 | 2 | 5 | 15 | 20 |
|  | 1.12 | 0 | 0 | 2 | 10 |
| 19 | 0.28 | 2 | 5 | 20 | 30 |
|  | 0.56 | 0 | 0 | 5 | 15 |
|  | 1.12 | 0 | 0 | 2 | 10 |
| 24 | 0.28 | 55 | 60 | 70 | 80 |
|  | 0.56 | 25 | 30 | 35 | 45 |
|  | 1.12 | 5 | 10 | 20 | 30 |
| Control | 0 | 60 | 75 | 80 | 90 |

Trial 7

This test was run to further evaluate the efficacy of one of the compounds as a fungicide in the control of the causative organisms of wheat and barley powdery mildew.

Five hundred milligrams of the test compound was dissolved in 10 ml. of acetone and sprayed on 50 g. of tumbling Florex 30/60 granules and allowed to air dry. The granules as sprayed thereby contained 1.0% active ingredient. Three replicate weighings each of 800, 400 and 200 mg. of the 1% granules, containing 8, 4 and 2 mg. of the test compound, respectively, were made. Three weighings of untreated granules were also made. The granules were added to 3 cups of tumbling soil per treatment and mixed thoroughly.

The 3 cups of soil containing the granules were placed on top of untreated soil in pots as in Experiment 6 above. Twenty seeds of either Larker barley, Proctor barley, or Logan wheat were planted per pot in the treated soil at a depth of 1 cm. The pots were top watered as needed. Six days after planting, the plants were inoculated with the respective powdery mildew conidia from already infected wheat and barley plants.

Beginning 12 days after planting (DAP), observations were made to determine the incidence of powdery mildew. The results are recorded in Table 7, which follows. The test compound is identified by the number of the operating example describing the preparation of the compound.

TABLE 7

| Compound | Appln.* rate | Powdery Mildew Incidence at DAP on: | | | |
|---|---|---|---|---|---|
|  |  | 12 | 15 | 19 | 23 |
|  |  | Logan wheat | | | |
| 19 | 200 | 5 | 10 | 20 | 30 |
|  | 400 | 2 | 5 | 10 | 20 |
|  | 800 | 0 | 0 | 1 | 2 |
| Control | 0 | 50 | 55 | 60 | 65 |
|  |  | Larker barley | | | |
| 19 | 200 | 0 | 2 | 10 | 20 |
|  | 400 | 0 | 0 | 5 | 15 |
|  | 800 | 0 | 0 | 1 | 5 |
| Control | 0 | 55 | 60 | 65 | 65 |
|  |  | Proctor barley | | | |
| 19 | 200 | 2 | 5 | 15 | 30 |
|  | 400 | 0 | 0 | 5 | 20 |
|  | 800 | 0 | 0 | 2 | 15 |

TABLE 7-continued

| Compound | Appln.* rate | Powdery Mildew Incidence at DAP on: | | | |
|---|---|---|---|---|---|
| | | 12 | 15 | 19 | 23 |
| Control | 0 | 55 | 60 | 65 | 65 |

*Mg. of 1% granules per pot.

Trial 8

The efficacy of a number of the compounds against the causative organisms of four fungal diseases of wheat was determined in the greenhouse by foliar and soil drench application of the test compounds according to the following procedure.

Wheat, variety Monon, was planted in round plastic pots measuring 6.25 cm. in diameter, containing soil covered with sand. Four pots per disease, together with 4 checks pots per disease were prepared, for a total of 32 pots. When the seedlings were about 4–5 inches tall, that is, at about 5–7 days after planting the seeds, depending on the time of year the test was run, the plants in each of two test pots were sprayed with a single formulated test compound (application rate of 400 ppm. a.i.), while the soil in each of two other test pots was drenched with 10 ml. per pot of the same formulated test compound (application rate 12.32 kg./ha.). This procedure was carried out for each formulated test compound, employing two pots each for the spray application and two pots each for the soil drench application for each disease. As checks in each disease test, the plants in two check pots were sprayed with the water-diluted solvent-emulsifier solution, and the soil in two more check pots was drenched with the water-diluted solvent-emulsifier solution, for a total of four check pots for each disease.

Within 24 hours after application of the formulated test compounds and the solvent-surfactant solution as described above, all the pots were placed in the greenhouse and inoculated respectively with the conidia of the test organisms. The plants were then observed at 4–8 days after transfer to the greenhouse for symptoms of the diseases and the disease ratings recorded.

The disease ratings are as follows:
1—Severe
213 Moderately Severe
3—Moderate
4—Slight
5—No Disease (100% control)

The test organisms were the following:
Helminthosporium Leaf Spot (H)
(*Helminthosporium sativum*)
Leaf Rust (LR)
(*Puccinia recondita tritici*)
Powdery mildew (PM)
(*Erysiphe graminis tritici*)
Septoria Leaf Blotch (S)
(*Septoria tritici*)

The results are set forth in Table 8, which follows, the compounds being identified by the numbers of their preparative examples. Where more than one test was run, the results were averaged, and are so recorded.

TABLE 8

| | Appln. Rate | Disease Control Ratings | | | | Appln. Rate | | | | |
|---|---|---|---|---|---|---|---|---|---|---|
| | | Foliar Application | | | | | Soil Drench | | | |
| Compound | ppm. | PM | LR | H | S | kg./ha. | PM | LR | H | S |
| 1 | 400 | 4 | — | 3 | 3 | 12.32 | 5 | — | 4 | 3 |
| 4 | 400 | 3 | — | 1 | 1 | 12.32 | 1 | — | 1 | 1 |
| 5 | 400 | 3 | — | 1 | 1 | 12.32 | 4 | — | 1 | 1 |
| 11 | 400 | 4 | — | 1 | 1 | 12.32 | 5 | — | 1 | 1 |
| 14 | 400 | 1 | — | 1 | 1 | 12.32 | 4 | — | 3 | 1 |
| 16 | 400 | 1 | 3 | 1 | 1 | 12.32 | 1 | 1 | 1 | 1 |
| 18 | 400 | 2.5 | 3 | 4 | 3.5 | 12.32 | 4.5 | 4 | 1 | 3.5 |
| 19 | 400 | 5 | 1 | 4 | — | 12.32 | 4 | 1 | 1 | — |
| 20 | 400 | 1 | 1 | 1 | 3 | 12.32 | 1 | 1 | 1 | 1 |
| 21 | 400 | 3 | — | 3 | 1 | 12.32 | 4 | — | 1 | 1 |
| 24 | 400 | 4 | — | 1 | 1 | 12.32 | 5 | — | 4 | 1 |
| 26 | 400 | 3.5 | 1 | 1 | 1 | 12.32 | 5 | 3 | 1 | 1 |
| 27 | 400 | 4 | 1 | 1 | 1 | 12.32 | 5 | 1 | 1 | 1 |
| 29 | 400 | 5 | 1 | 3 | 5 | 12.32 | 5 | 3 | 3 | 4 |
| 30 | 400 | 1 | 1 | 4 | 5 | 12.32 | 4 | 1 | 1 | 5 |
| 31 | 400 | 4 | 1 | 1 | 4 | 12.32 | 4 | 1 | 1 | 4 |
| 32 | 400 | 5 | 1 | 5 | 5 | 12.32 | 5 | 5 | 5 | 5 |
| 35 | 400 | 5 | 1 | 5 | 5 | 12.32 | 4 | 5 | 1 | 5 |
| 36 | 400 | 4 | 1 | 4 | 1 | 12.32 | 5 | 4 | 1 | 5 |
| 48 | 400 | 1 | 1 | 1 | 1 | 12.32 | 4 | 1 | 1 | 1 |
| 49 | 400 | 1 | 1 | 1 | 1 | 12.32 | 1 | 1 | 4 | 1 |
| 50 | 400 | 5 | 1 | 4 | 4 | 12.32 | 5 | 5 | 5 | 4 |
| 51 | 400 | 5 | 1 | 2.5 | 4 | 12.32 | 5 | 5 | 3 | 4.5 |
| 52 | 400 | 4 | 1 | 3 | 2.5 | 12.32 | 4.5 | 1 | 1 | 1 |
| 54 | 400 | 2.5 | 1 | 1 | 1 | 12.32 | 3.5 | 1 | 1 | 1 |
| 55 | 400 | 3 | — | 1 | 1 | 12.32 | 3 | — | 1 | 1 |
| 57 | 400 | 4 | 1 | 4 | 5 | 12.32 | 5 | 4 | 4 | 4 |
| 64B | 400 | 1 | 1 | 1 | 1 | 12.32 | 5 | 1 | 1 | 1 |
| 64C | 400 | 5 | 5 | 4 | 4 | 12.32 | 5 | 1 | 1 | 4 |
| 64F | 400 | 5 | 1 | 1 | 1 | 12.32 | 5 | 1 | 1 | 4 |
| 65 | 400 | 5 | 1 | 5 | 1 | 12.32 | 5 | 4 | 1 | 4 |
| 66 | 400 | 5 | 1 | 1 | 5 | 12.32 | 1 | 1 | 1 | 1 |
| 67 | 400 | 3.5 | 3 | 3.5 | 4.5 | 12.32 | 5 | 3 | 1 | 1 |
| 68 | 400 | 2.5 | 1 | 1 | 4.5 | 12.32 | 3 | 1 | 1 | 1 |
| 69 | 400 | 4 | 3 | 4 | 4 | 12.32 | 4 | 1 | 1 | 1 |
| 70 | 400 | 4 | 1 | 1 | 1 | 12.32 | 4 | 1 | 1 | 4 |
| 71 | 400 | 1 | 1 | 1 | 3 | 12.32 | 4 | 1 | 1 | 5 |
| 76 | 400 | 3 | 1 | 5 | 4 | 12.32 | 5 | 3 | 1 | 5 |
| 78 | 400 | 4 | 1 | 3 | 4 | 12.32 | 5 | 3 | 1 | 5 |

TABLE 8-continued

| | | Disease Control Ratings | | | | | | | | |
|---|---|---|---|---|---|---|---|---|---|---|
| | Appln. Rate | Foliar Application | | | | Appln. Rate | Soil Drench | | | |
| Compound | ppm. | PM | LR | H | S | kg./ha. | PM | LR | H | S |
| 79 | 400 | 5 | 1 | 1 | 1 | 12.32 | 5 | 1 | 1 | 4 |
| 83 | 400 | 4 | 1 | 1 | 1 | 12.32 | 5 | 1 | 1 | 5 |
| 85 | 400 | 5 | 1 | 5 | 5 | 12.32 | 5 | 5 | 1 | 5 |
| 86 | 400 | 4 | 4 | 5 | 4 | 12.32 | 5 | 5 | 1 | 4 |
| 90 | 400 | 5 | 1 | 4 | 4 | 12.32 | 5 | 1 | 1 | 1 |
| Control | 0 | 1 | 1 | 1 | 1 | 0.0 | 1 | 1 | 1 | 1 |

Trial 9

Following the same general testing procedure as described in Trial 8, above, additional testing of the efficacy of some of the compounds of Trial 8 was accomplished at the same application rates, as well as at lower application rates. The results are recorded in Table 9, which follows.

Trial 10

The efficacy of a number of the compounds against *Erysiphe graminis hordei*, the causative agent of powdery mildew of barley, was determined in a field trial according to the following procedure.

Barley, variety Maris Otter, was planted in sandy loam of organic content an estimated 3 percent. The

TABLE 9

| | | Disease Control Ratings | | | | | | | | |
|---|---|---|---|---|---|---|---|---|---|---|
| | Appln. Rate | Foliar Application | | | | Appln. Rate | Soil Drench | | | |
| Compound | ppm. | PM | LR | H | S | kg./ha. | PM | LR | H | S |
| 1 | 400 | 5 | 4 | — | 3 | 12.32 | 5 | 4 | 1 | — |
| | 100 | 4 | 3 | — | 3 | 3.36 | 5 | 3 | 1 | — |
| | 25 | 3 | 1 | — | 1 | 0.78 | 4 | 3 | 1 | — |
| 19 | 400 | 4 | — | 3 | — | 12.32 | 5 | — | — | — |
| | 100 | 3 | — | — | — | 3.36 | 4 | — | — | — |
| | 25 | 3 | — | — | — | 0.78 | 3 | — | — | — |
| 24 | 400 | 4 | 1 | — | — | 12.32 | 5 | 4 | 1 | — |
| | 100 | 3 | 1 | — | — | 3.36 | 4 | 3 | 1 | — |
| | 25 | 3 | 1 | — | — | 0.78 | 1 | 1 | 1 | — |
| 29 | 400 | 5 | — | 4 | 4 | — | Not tested | | | |
| | 100 | 5 | — | 1 | 1 | — | | | | |
| | 25 | 4 | — | 1 | 1 | — | | | | |
| 30 | 400 | — | — | 4 | 5 | — | | | | |
| | 100 | — | — | 1 | 3 | — | | | | |
| | 25 | — | — | 1 | 1 | — | | | | |
| 31 | 400 | 5 | — | — | 4 | 12.32 | 5 | — | — | 5 |
| | 100 | 4 | — | — | 2.5 | 3.36 | 2.5 | — | — | 3 |
| | 25 | 2.5 | — | — | 1 | 0.78 | 1 | — | — | 1 |
| 32 | 400 | 5 | — | 4 | 5 | 12.32 | 5 | 5 | 3 | 5 |
| | 100 | 4 | — | 3.5 | 3 | 3.36 | 5 | 5 | 1 | 4.5 |
| | 25 | 4 | — | 2 | 2.5 | 0.78 | 4 | 1 | 1 | 2.5 |
| 35 | 400 | 5 | 1 | 3 | 5 | 12.32 | 5 | 4 | — | 4 |
| | 100 | 4.5 | 1 | 1 | 4 | 3.36 | 5 | 1 | — | 4 |
| | 25 | 3.5 | 1 | 1 | 2.5 | 0.78 | 4.5 | 1 | — | 1 |
| 36 | 400 | 4 | — | 5 | — | 12.32 | 5 | 4 | — | 5 |
| | 100 | 4.5 | — | 4.5 | — | 3.36 | 5 | 3 | — | 5 |
| | 25 | 3.5 | — | 3 | — | 0.78 | 3 | 1 | — | 1 |
| 50 | 400 | 5 | — | 5 | 4 | 12.32 | 5 | — | 3 | 5 |
| | 100 | 5 | — | 4 | 4 | 3.36 | 5 | — | 1 | 4 |
| | 25 | 4.5 | — | 3 | 1 | 0.78 | 5 | — | 1 | 1 |
| | 6 | 3 | — | 1 | — | 0.22 | 3 | — | — | — |
| 51 | 400 | 5 | — | 5 | 4 | 12.32 | 5 | — | 3 | 5 |
| | 100 | 5 | — | 4 | 4 | 3.36 | 5 | — | 1 | 4 |
| | 25 | 5 | — | 3 | 1 | 0.78 | 5 | — | 1 | 1 |
| | 6 | 3 | — | 1 | — | 0.22 | 3 | — | — | — |
| 57 | 400 | 4 | — | 5 | 5 | 12.32 | 5 | — | 4 | 4 |
| | 100 | 4 | — | 4 | 4 | 3.36 | 5 | — | 1 | 1 |
| | 25 | 3.5 | — | 1 | 4 | 0.78 | 3.5 | — | 1 | 1 |
| | 6 | 3 | — | 1 | 3 | 0.22 | 1 | — | 0 | 0 |
| 69 | 400 | 1 | 3 | 5 | 5 | 12.32 | 4 | 1 | — | — |
| | 100 | 1 | 1 | 4 | 4 | 3.36 | 4 | 1 | — | — |
| | 25 | 1 | 1 | 1 | 1 | 0.78 | 1 | 1 | — | — |
| 83 | 400 | 5 | — | — | — | 12.32 | 5 | — | — | 5 |
| | 100 | 3 | — | — | — | 3.36 | 5 | — | — | 5 |
| 85 | 400 | 5 | — | 5 | 5 | 12.32 | 5 | 4 | — | 5 |
| | 100 | 4 | — | 5 | 5 | 3.36 | 4 | 1 | — | 4 |
| | 25 | 3 | — | 4 | 4 | 0.78 | 1 | 1 | — | 1 |
| 86 | 400 | 4 | 4 | 4 | 5 | 12.32 | 5 | 5 | — | 5 |
| | 100 | 1 | 4 | 4 | 5 | 3.36 | 3 | 5 | — | 4 |
| | 25 | 1 | 4 | 4 | 4 | 0.78 | 1 | 3 | — | 1 |
| Control | 0 | 1 | 1 | 1 | 1 | 0.0 | 1 | 1 | — | — | field was divided into plots measuring 1×2 meters. There were 9 rows per plot, the rows being 12 cm. apart. There were 4 replicates run for each application rate of each test compound. Control plots to which no test compounds were applied were also run.

Each test compound was formulated as a 25 percent wettable powder (25% WP). The formulations were diluted with water to prepare the solutions containing the desired quantities of active ingredient. The thus-prepared solutions were applied using a microsprayer operating at a pressure of 2.75 kg./sq. meter. The band width sprayed was 35 cm.

The test compounds were applied to the barley 52 days after the barley was planted. Visual evaluations of the control effected by the test compounds against the powdery mildew caused by *Erysiphe graminis hordei* were made 12 days after treatment (DAT), when the barley plants were in the 4-5 leaf stage. The disease control ratings were on a 0-10 scale, where 0=no control, 5=50% control, and 10=100% control. The results are recorded in Table 11, which follows, the mean value of the ratings of replicates being recorded. Each test compound is identified by the number of its preparative example in the specification.

TABLE 10

| Compound | Appln. Rate kg/ha | Control Rating |
|---|---|---|
| 1 | 0.125 kg/ha | 3.1 |
|  | 0.5 | 5.8 |
|  | 1.0 | 5.9 |
| 19 | 0.125 | 2.5 |
|  | 0.5 | 3.1 |
|  | 1.0 | 4.0 |
| 29 | 0.125 | 1.1 |
|  | 0.5 | 2.4 |
|  | 1.0 | 3.8 |
| 30 | 0.125 | 0.9 |
|  | 0.5 | 2.1 |
|  | 1.0 | 2.6 |
| 32 | 0.125 | 1.3 |
|  | 0.5 | 4.0 |
|  | 1.0 | 4.6 |
| 35 | 0.125 | 2.0 |
|  | 0.5 | 4.5 |
|  | 1.0 | 4.3 |
| 36 | 0.125 | 2.5 |
|  | 0.5 | 3.6 |
|  | 1.0 | 4.5 |
| 85 | 0.125 | 1.6 |
|  | 0.5 | 3.3 |
|  | 1.0 | 4.0 |
| Control | 0 | 0 |

Other embodiments of this invention are practiced by applying (a) a plant growth regulating and non-herbicidal amount or (b) a herbicidally effective amount of one or more compounds of the generic formulae (VII) or (VIII) depending on the desired effect. The compounds of this invention have been shown to regulate or modify the growth processes of terrestrial plants. They are also herbicidally active in that they cause death or severe herbicidal injury to plants. The amount of active compound required to produce a herbicidal effect is generally greater than that employed to regulate plant growth. These amounts vary greatly depending on the target plant species and the particular active compound to be used.

The compounds can be used as terrestrial plant growth regulators or herbicides either pre- or post-emergence. As shown in the following evaluations, the compounds are more effective where applied pre-emergence, i.e., applied to the soil after planting of the seed but before germination and emergence of the new plants. The compounds are generally used in crop growing areas. However, the herbicidal activity of the compounds can also be used to eliminate weeds or other undesired plant growth in other areas such as gravel driveways, clay tennis courts, walls, road shoulders and the like.

The compositions can be used directly or can be formulated into compositions as described above for use of the substituted 1-thia-3-aza-4-ones as fungicides. As above the compositions generally contain in addition to the substituted 1-thia-3-aza-4-one, one or more or a plurality of additaments including water, polyhydroxy compounds, petroleum distillates, and other dispersion media, surface-active dispersing agents, emulsifiers, and finely-divided inert solids. The concentration of the substituted 1-thia-3-aza-4-ones in these compositions may vary depending on whether the composition is intended as an emulsifiable concentrate or a wettable powder designed to be subsequently diluted with additional inert carrier, such as water, to produce the ultimate treating composition, or is intended for direct application.

The treating compositions are most conveniently formulated by preparing liquid or solid concentrates, which are subsequently diluted to the desired level for use. Emulsifiable liquid concentrates can be prepared by incorporating from about 1 to about 30 percent by weight of the active ingredient, and an emulsifying agent, in a suitable water-immiscible organic liquid. Such concentrates may be further diluted with water to form spray mixtures in the form of oil-in-water emulsions. Such spray compositions then comprise active compound, water-immiscible solvent, emulsifying agent, and water. Suitable emulsifying agents can be of the nonionic or ionic types, or blends thereof, and include condensation products of alkylene oxides with phenols and organic acids, polyoxyethylene derivatives of sorbitan esters, such as polyoxyethylene sorbitan mono-oleate and polyoxyethylene sorbitan mono-laurate; complex ether alcohols, such as polyglycol ether sulfonate; ionics of the aralkyl sulfonate type, such as alkylamine dodecylbenzene sulfonate, and the like. Suitable water-immiscible organic liquids to be employed include aromatic hydrocarbons, aliphatic hydrocarbons, cycloaliphatic hydrocarbons and mixtures thereof, such as petroleum distillates.

Solid concentrate mixtures can be prepared by incorporating from about 1 to about 90% by weight of the substituted 1-thia-3-aza-4-one in a finely-divided inert solid carrier such as bentonite, fuller's earth, diatomaceous earth, silica, expanded mica, talc, chalk, and the like. Dispersing and/or wetting agents can be incorporated along with the substituted 1-thia-3-aza-4-one in the solid carrier to form wettable powder concentrates ranging from about 1 to about 75% by weight concentration, which subsequently can be dispersed in water or other hydroxylated carrier to form spray compositions. Suitable wetting agents include condensed arylsulfonic acids and sodium salts thereof, sodium lignosulfate, sulfonate oxide condensate blends, alkylaryl polyether alcohols, sulfonated nonionic blends, anionic wetting agents, and the like.

Spreadable granules can be prepared using calcined attapulgite clay as the solid diluent. Dry dispersions can be prepared on herbicidally inert carriers, such as vermiculite, peat moss and the like.

Evaluation of the substituted 1-thia-3-aza-4-one compounds as terrestrial plant growth regulators and as herbicides is illustrated by the following procedures.

Trial 11

The terrestrial plant growth regulator activity of a number of the compounds of the above formula was determined in the greenhouse according to the following procedure.

The plants used in this study were soybean, variety Chippewa; barley, variety Larker; ryegrass, variety Manhattan; and cucumber, variety Green Prolific. All plants were grown in soil in 10 cm. plastic pots. The soil in one-half of the number of pots was covered with vermiculite after the seeds were sown, and those pots used for a foliar spray application of the test compounds. The soil in the other half of the number of pots was covered with soil after the seeds were planted, and those pots used for a soil drench application of the test compounds. The seedling plants were fertilized biweekly until termination of the test with a solution containing 6.7 g. of Rapid-Gro (a commercially-available fertilizer) per gallon. After the plants became established, and before the treatment date, the plants in each pot were thinned to the desired number of plants per pot. Thus, there were two soybean plants per pot, five barely plants per pot, an estimated 100 ryegrass plants per pot, and one cucumber plant per pot. The ryegrass was clipped to a height of 2.5 cm. on the day before treatment.

The plants in one-half the number of pots were treated with a soil drench at the rate of 5.6 kg./ha. of test compound. The plants in the other one-half the number of pots were treated with a foliar spray at an application rate of 2000 ppm. The foliar spray applications were made with a DeVilbiss atomizer at 10-12 psi., the foliage of all the plants being sprayed to wetness.

The test compounds were formulated in the following manner. A solution was prepared of 50 mg. of the test compound in 3 ml. of a mixture of ethanol and acetone (1:1 by volume), and diluted to a total volume of 25 ml. with Toximul R and S water (300 ppm Toximul R and 400 ppm Toximul S in deionized water). Toximul R and Toximul S are general purpose matched pair emulsifiers and are a liquid sulfonate/nonionic blend produced by Stepan Chemical Company, Northfield, Ill., U.S.A. Fourteen ml. of the solution was used for the foliar application. For the soil drench, 11 ml. was diluted to 100 ml., with a 20 ml. aliquot then being poured into each pot. The age of the plants at time of treatment varied as follows:

Soybean—16 days
Barley—7 days
Ryegrass—10 days
Cucumber—17 days

After treatment, the soybean and ryegrass were maintained in the greenhouse for 15 days, at the end of which time visual evaluations were made of growth regulator effects and injury. The barley and cucumber plants were maintained in the greenhouse for 20 days, at the end of which time the visual evaluations of growth regulator effects and injury were made. A scale of 0, 1, 2, and 3 was used. Zero is no effect and 3 is distinct or severe effect. A "+" is used for growth promotion, while a "−" indicates inhibition or depression. The results are set forth in Table 10, which follows.

TABLE 11

| | | | \multicolumn{3}{c}{Plant Growth Regulator Effects} | | | | | | | | | | | |
|---|---|---|---|---|---|---|---|---|---|---|---|---|---|---|---|---|
| Com- | Appln. | Treat- | Cotton | | | Soybean | | | Cucumber | | | Barley | | | | Ryegrass | | |
| pound | Rate | ment | H | BR | I[1] | H | BR | I[1] | H | F | I[1] | H | T | F | I[1] | H | T | I[1] |
| 1 | 2000 ppm. | Foliar | | | | 0 | 0 | 0 | 0 | 0 | 0 | 0 | 0 | 0 | 0 | 0 | 0 | 0 |
| | 5.6 kg/ha | Drench | | | | 0 | 0 | 0 | 0 | 0 | 0 | −3 | 0 | −3 | 2CB | −1 | 0 | 0 |
| 29 | 2000 ppm. | Foliar | | | | −1 | 0 | 1M[2] | 0 | 0 | 0 | 0 | 0 | 0 | 0 | 0 | 0 | 0 |
| | 5.6 kg/ha | Drench | | | | 0 | 0 | 0 | 0 | 0 | 0 | −3 | 0 | −3 | 2C | −1 | 0 | 1B |
| 30 | 2000 ppm. | Foliar | | | | 0 | 0 | 0 | 0 | 0 | 0 | 0 | 0 | 1 | 0 | 0 | 0 | 0 |
| | 5.6 kg/ha | Drench | | | | 0 | 0 | 0 | 0 | 0 | 0 | −2 | 1 | 0 | 1B | −1 | 0 | 1B |
| 31 | 2000 ppm. | Foliar | 0 | 0 | 1M | 0 | 0 | 0 | −1 | 0 | 0 | 0 | 0 | | 0 | 0 | 0 | 0 |
| | 5.6 kg/ha | Drench | 0 | 0 | 0 | 0 | 0 | 0 | 0 | 0 | 0 | 0 | 0 | | 0 | −1 | 0 | 0 |
| 33 | 2000 ppm. | Foliar | −1 | 0 | 0 | 0 | 1 | 2M | 0 | 0 | 0 | 0 | 0 | | 0 | 0 | 0 | 0 |
| | 5.6 kg/ha | Drench | 0 | 0 | 0 | 0 | 0 | 0 | 0 | 0 | 0 | 0 | 0 | | 0 | −1 | 0 | 0 |
| 35 | 2000 ppm. | Foliar | | | | −1 | 0 | 2M | −1 | 0 | 0 | 0 | 0 | 0 | 0 | 0 | 0 | 0 |
| | 5.6 kg/ha | Drench | | | | −2 | 0 | 0 | 0 | 0 | 0 | −3 | 0 | −3 | 2BC | −1 | 0 | 1B |
| 36 | 2000 ppm. | Foliar | 0 | 0 | 1M | 0 | 0 | 2M | 0 | 0 | 0 | 0 | 0 | | 0 | 0 | 0 | 0 |
| | 5.6 kg/ha | Drench | 0 | 0 | 0 | 0 | 0 | 0 | −3 | 0 | 1B | −3 | 2 | | 0 | −1 | 0 | 1B |
| 48 | 2000 ppm. | Foliar | 0 | 0 | 0 | 0 | 1 | 3M | −1 | 0 | 0 | 0 | 0 | | 0 | 0 | 0 | 0 |
| | 5.6 kg/ha | Drench | 0 | 0 | 0 | 0 | 0 | 0 | 0 | 0 | 0 | −3 | 0 | | 2C | −1 | 0 | 0 |
| 48 | 2000 ppm. | Foliar | 0 | 0 | 1B | | | | 0 | 0 | 0 | 0 | 0 | | 0 | 0 | 0 | 0 |
| | 5.6 kg/ha | Drench | 0 | 0 | 1B | 0 | 0 | 0 | −2 | 0 | 0 | −3 | 0 | | 2B | −1 | 0 | 0 |
| 49 | 2000 ppm. | Foliar | 0 | 0 | 0 | | | | −1 | 0 | 0 | −1 | 0 | | 2B | −1 | 0 | 0 |
| | 5.6 kg/ha | Drench | | | 1B | 0 | 0 | 0 | −1 | 0 | 0 | −1 | 0 | | 2B | −1 | 0 | 0 |
| 55 | 2000 ppm. | Foliar | −1 | 0 | 1B | 0 | 0 | 0 | 0 | 0 | 0 | 0 | 0 | | 0 | 0 | 0 | 0 |
| | 5.6 kg/ha | Drench | 0 | 0 | 0 | 0 | 0 | 0 | 0 | 0 | 0 | 0 | 0 | | 0 | 0 | 0 | 0 |
| 56 | 2000 ppm | Foliar | 0 | 0 | 1M | 0 | 2 | 2M | 0 | 0 | 1C | 0 | 1 | | 0 | 0 | 0 | 0 |
| | 5.6 kg/ha | Drench | −1 | 0 | 0 | 0 | 0 | 0 | −3 | 0 | 1C | −3 | 0 | | 1C | −2 | 0 | 1B |
| 56 | 2000 ppm. | Foliar | 0 | 0 | 1M | 0 | 1 | 3M | −1 | 0 | 0 | 0 | 0 | | 1C | 0 | 0 | 0 |
| | 5.6 kg/ha | Drench | 0 | 0 | 1B | 0 | 0 | 1B | −2 | −3 | 1C | −3 | −3 | | 2C | −1 | 0 | 1B |
| 58 | 2000 ppm. | Foliar | 0 | 0 | 0 | 0 | 0 | 0 | 0 | 0 | 0 | 0 | 0 | | 0 | 0 | 0 | 0 |
| | 5.6 kg/ha | Drench | 0 | 0 | 0 | 0 | 0 | 0 | 0 | 0 | 0 | 0 | 0 | | 0 | 0 | 0 | 0 |
| 61 | 2000 ppm. | Foliar | 0 | 0 | 0 | −1 | 0 | 0 | −1 | −2 | 0 | 0 | 0 | | 0 | 0 | 0 | 0 |
| | 5.6 kg/ha | Drench | 0 | 0 | 0 | 0 | 0 | 0 | −2 | −1 | 0 | 0 | 0 | | 0 | 0 | 0 | 0 |
| 63 | 2000 ppm. | Foliar | 0 | 0 | 0 | −1 | 0 | 1M | 0 | 0 | 0 | 0 | 0 | 0 | 0 | 0 | 0 | 0 |
| | 5.6 kg/ha | Drench | −1 | 0 | 0 | 0 | 0 | 0 | 0 | 0 | 0 | −1 | 0 | 0 | 0 | 0 | 0 | 0 |
| 64 | 2000 ppm. | Foliar | −3 | 0 | 0 | −2 | 1 | 0 | −1 | 0 | 0 | 0 | 0 | | 0 | 0 | 0 | 0 |
| | 5.6 kg/ha | Drench | 0 | 0 | 0 | −2 | 1 | 0 | −3 | 0 | 1C | −3 | −3 | | 1C | −2 | 0 | 1B |
| 64 | 2000 ppm. | Foliar | 0 | 0 | 3M | −3 | 2 | 0 | −2 | 0 | 0 | 0 | 0 | | 0 | 0 | 0 | 0 |
| | 5.6 kg/ha | Drench | 0 | 0 | 0 | −1 | 0 | 0 | −3 | −2 | 0 | −3 | 0 | | 1C | −3 | 0 | 0 |

TABLE 11-continued

| Compound | Appln. Rate | Treatment | Cotton H | Cotton BR | Cotton I[1] | Soybean H | Soybean BR | Soybean I[1] | Cucumber H | Cucumber F | Cucumber I[1] | Barley H | Barley T | Barley F | Barley I[1] | Ryegrass H | Ryegrass T | Ryegrass I[1] |
|---|---|---|---|---|---|---|---|---|---|---|---|---|---|---|---|---|---|---|
| 64C | 2000 ppm. | Foliar | 0 | 0 | 0 | −2 | 0 | 2M | −1 | 0 | 2C | 0 | 0 | 0 | 0 | 0 | 0 | 0 |
|  | 5.6 kg/ha | Drench | −2 | 0 | 0 | 0 | 0 | 0 | −1 | 0 | 0 | −3 | 0 | −3 | 1B | −3 | 0 | 0 |
| 64D | 2000 ppm. | Foliar | −1 | 0 | 0 | −1 | 1 | 3M | 0 | 0 | 1B | −1 | 0 |  | 0 | 0 | 0 | 0 |
|  | 5.6 kg/ha | Drench | 0 | 0 | 0 | 0 | 0 | 0 | −1 | 0 | 0 | −3 | 3 |  | 0 | −2 | 0 | 0 |
| 66 | 2000 ppm. | Foliar | 0 | 0 | 1M | 0 | 0 | 1M | 0 | 0 | 1B | 0 | 0 |  | 0 | 0 | 0 | 0 |
|  | 5.6 kg/ha | Drench | 0 | 0 | 0 | 0 | 0 | 0 | 0 | 0 | 0 | −3 | 2 |  | 0 | −1 | 0 | 0 |
| 72 | 2000 ppm. | Foliar | 0 | 0 | 0 | 0 | 0 | 2M | 0 | 0 | 0 | 0 | 0 |  | 0 | 0 | 0 | 0 |
|  | 5.6 kg/ha | Drench | 0 | 0 | 0 | 0 | 0 | 0 | 0 | −1 | 0 | 0 | 0 |  | 1B | 0 | 0 | 0 |
| 74 | 2000 ppm. | Foliar | 0 | 0 | 1M | 0 | 0 | 2B | 0 | 0 | 1B | 0 | 0 |  | 0 | 0 | 0 | 0 |
|  | 5.6 kg/ha | Drench | 0 | 0 | 0 | 0 | 0 | 1B | 0 | 0 | 0 | −1 | 0 |  | 1B | −1 | 0 | 1C |
| 76 | 2000 ppm. | Foliar | 0 | 0 | 1M |  |  |  | 0 | 0 | 1C | 0 | 0 |  | 0 | 0 | 0 | 0 |
|  | 5.6 kg/ha | Drench | −1 | 0 | 0 | 0 | 0 | 0 | 0 | 0 | 0 | −3 | 0 |  | 2C | −2 | 0 | 0 |
| 78 | 2000 ppm. | Foliar | 0 | 0 | 1C |  |  |  | 0 | 0 | 0 | 0 | 0 |  | 0 | 0 | 0 | 0 |
|  | 5.6 kg/ha | Drench | −1 | 0 | 1B | 0 | 0 | 0 | 0 | 0 | 1C | 0 | 0 |  | 0 | 0 | 0 | 0 |
| 79 | 2000 ppm. | Foliar | 0 | 0 | 0 |  |  |  | −1 | 0 | 0 | 0 | 0 |  | 0 | 0 | 0 | 0 |
|  | 5.6 kg/ha | Drench | 0 | 0 | 0 | −1 | 0 | 0 | 0 | 0 | 1B | −2 | 0 |  | 0 | 0 | 0 | 0 |
| 80 | 2000 ppm. | Foliar | 0 | 0 | 0 |  |  |  | −1 | 0 | 0 | 0 | 0 |  | 1C | 0 | 0 | 0 |
|  | 5.6 kg/ha | Drench | 0 | 0 | 1B | 0 | 0 | 0 | 0 | 0 | 0 | 0 | 0 |  | 0 | 0 | 0 | 0 |
| 83 | 2000 ppm. | Foliar | −1 | 0 | 0 | 0 | 0 | 0 | 0 | 0 | 1M | 0 | 0 | 0 | 0 | 0 | 0 | 0 |
|  | 5.6 kg/ha | Drench | 0 | 0 | 0 | 0 | 0 | 0 | −2 | 0 | 1B | −3 | 0 | 0 | 0 | −2 | 0 | 1B |
| 84 | 2000 ppm. | Foliar | 0 | 0 | 0 | 0 | 0 | 0 | 0 | 0 | 0 | 0 | 0 |  | 0 | 0 | 0 | 0 |
|  | 5.6 kg/ha | Drench | 0 | 0 | 0 | 0 | 0 | 0 | 0 | 0 | 1C | 0 | 0 |  | 0 | 0 | 0 | 0 |
| 85 | 2000 ppm. | Foliar | 0 | 0 | 1M | 0 | 0 | 1B | −1 | 0 | 0 | 0 | 0 |  | 0 | 0 | 0 | 0 |
|  | 5.6 kg/ha | Drench | 0 | 0 | 0 | 0 | 0 | 0 | 0 | 0 | 0 | −3 | 3 |  | 0 | −1 | 0 | 0 |
| 86 | 2000 ppm. | Foliar | 0 | 0 | 1B | 0 | 0 | 0 | 0 | 0 | 0 | 0 | 0 | 0 | 0 | 0 | 0 | 0 |
|  | 5.6 kg/ha | Drench | 0 | 0 | 0 | 0 | 0 | 0 | 0 | 0 | 0 | −2 | 0 | 0 | 0 | −2 | 0 | 0 |
| 89A | 2000 ppm. | Foliar | 0 | 0 | 1C | 0 | 0 | 1M | 0 | 0 | 0 | −1 | 0 |  | 1C | 0 | 0 | 0 |
|  | 5.6 kg/ha | Drench | 0 | 0 | 0 | 0 | 0 | 0 | 0 | 0 | 0 | 0 | 0 |  | 0 | 0 | 0 | 0 |
| 90 | 2000 ppm. | Foliar | 0 | 0 | 1C | 0 | 0 | 0 | 0 | 0 | 0 | 0 | 0 |  | 0 | 0 | 0 | 1 |
|  | 5.6 kg/ha | Drench | 0 | 0 | 0 | 0 | 0 | 0 | −1 | 0 | 0 | 0 | 0 |  | 0 | −2 | 0 | 0 |
| Control | 0 | Foliar | 0 | 0 | 0 | 0 | 0 | 0 | 0 | 0 | 0 | 0 | 0 | 0 | 0 | 0 | 0 | 0 |
|  |  | Drench | 0 | 0 | 0 | 0 | 0 | 0 | 0 | 0 | 0 | 0 | 0 | 0 | 0 | 0 | 0 | 0 |

[1]H = height
BR = branching
I = injury
F = flowering
T = tillering
[2]M = morphological effects
B = burn
C = chlorosis

Trial 12

A number of compounds of this invention were further tested for activity as terrestrial plant growth regulators for barley, soybeans, squash and snap beans using the following procedure.

Snap beans, Evans soybeans, squash, and/or Larker barley were planted in separate pots and permitted to grow for about one week. Formulations containing 1000 ppm. of test compounds were prepared as in Example 11 using the same solvent system then diluting with the appropriate amount of water. Test formulation was applied to the foliage of the plants by spraying to the point of run-off. The plants were allowed to grow in the greenhouse for 14 days after treatment at which time they were evaluated for growth regulatory effects of the test compounds. A rating was assigned using the same rating system as Example 11. The results are reported in Table 12.

TABLE 12

| Compound | Conc. | Squash G | Squash P | Snap Beans G | Snap Beans A | Snap Beans M | Snap Beans P[1] | Barley | Soybeans |
|---|---|---|---|---|---|---|---|---|---|
| 29 | 1000 | 0 | 0 | −3 | 0 | 3 | 0 |  |  |
| 30 | 1000 | −2 | 0 | 0 | 1 | 1 | 0 |  |  |
| 31 | 1000 | −1 | 0 | −2 | 1 | 2 | 1C[2] |  |  |
|  | 100 |  |  | 0 | 0 | 0 | 0 |  |  |
|  | 1000 |  |  | −2 | 0 | 2 | 1 |  |  |
| 32 | 1000 | 0 | 0 | −3 | −3 | 3 | 1C |  |  |
| 33 | 1000 | −3 | 1B | −3 | −2 | 3 | 1B |  |  |
| 34 | 1000 | −2 | 0 | −3 | −2 | 3 | 2C |  |  |
| 35 | 1000 | 0 | 0 | −2 | 0 | 3 | 1C |  |  |
|  | 1000 | −1 | 0 | −3 | 1 | 1 | 1B |  |  |
| 36 | 1000 | 0 | 0 | −3 | 0 | 1 | 1B |  |  |
| 39 | 1000 | 0 | 0 | 0 | 1 | 0 | 0 |  |  |
| 40 | 1000 | 0 | 0 | −2 | 0 | 2 | 1B |  |  |
| 41 | 1000 |  |  | −3 | 0 | 1 |  | 2X | −2B |
| 42 | 1000 |  |  | −1 | 0 | 0 |  | 0 | 0 |
| 44 |  |  |  | 0 | 0 | 0 |  | 0 | −1 |
| 45 | 1000 |  |  | 0 | 0 | 0 |  | 0B | 0 |
| 46 |  |  |  |  |  |  |  |  |  |
| 47 |  |  |  |  |  |  |  |  |  |
| 48 | 1000 | 0 | 0 | −3 | 0 | 1 | 1B |  |  |
| 49 | 1000 | −3 | 0 | −3 | 0 | 1 | 2B |  |  |

TABLE 12-continued

| Compound | Conc. | Squash G | Squash P | Snap Beans G | Snap Beans A | Snap Beans M | Snap Beans P[1] | Barley | Soybeans |
|---|---|---|---|---|---|---|---|---|---|
| 50 | 1000 | 0 | 0 | −3 | 0 | 0 | 1B | | |
| 51 | 1000 | 0 | 0 | −3 | 0 | 1 | 1B | | |
| 52 | 1000 | | | −3 | 0 | 0 | | | |
|    | 1000 | 0 | 0 | −1 | 0 | 1 | 1C | | |
| 53 | 1000 | 0 | 2M | −3 | 0 | 2 | | | |
| 55 | 1000 | | | −3 | 0 | 2 | | −2 | 0 |
| 56 | 1000 | 0 | 0 | −3 | 0 | 2 | 0 | | |
| 57 | 1000 | 0 | 0 | −3 | 0 | 2 | 0 | | |
| 58 | 1000 | 0 | 0 | −2 | 0 | 0 | 1B | | |
| 59 | 1000 | 0 | 0 | −3 | 0 | 1 | 1B | | |
| 60 | 1000 | 0 | 0 | −1 | 0 | 1 | 1C | | |
| 61 | 1000 | | | −3 | 0 | 3B | | 0 | −1 |
| 62 | | −2 | 0 | −3 | 0 | 0 | 0 | | |
|    | 1000 | | | −3 | 2 | 0 | | −3B | −3M |
| 64 | 1000 | | | −3 | 0 | 3 | | −3 | −3B |
| 64A | 1000 | | | −1 | 0 | 1 | | −1 | 0M |
| 64B | 1000 | | | 0 | 0 | 0 | | −1 | 0 |
| 64C | 1000 | | | −3 | 0 | 0 | | −3C | −2M |
| 64D | 1000 | | | −3 | 0 | 3B | | −3 | −1B |
| 64E | 1000 | 0 | 0 | −1 | 1 | 1 | 0 | | |
| 65 | 1000 | 0 | 0 | −3 | −3 | 0 | 2C | | |
| 66 | 1000 | −2 | 0 | −3 | −1 | 1 | 1C | | |
| 71 | 1000 | 0 | 0 | 0 | 0 | 0 | 0 | | |
| 72 | 1000 | −1 | 0 | −2 | −1 | 3 | 2C | | |
| 73 | 1000 | −2 | 0 | −2 | 2 | 3 | 1B | | |
| 74 | 1000 | −2 | 1C | −3 | 2 | 0 | 0 | | |
| 75 | 1000 | −2 | 0 | 1 | 1 | 0 | 0 | | |
| 76 | 1000 | | | −3 | 0 | 0 | 1 | | |
| 77 | 1000 | 1 | 0 | −2 | 0 | 0 | 0 | | |
| 78 | 1000 | | | −3 | 2 | 2 | 1B | | |
| 79 | 1000 | | | −3 | 0 | 0 | 0 | | |
| 80 | 1000 | | | −1 | 0 | 1 | 0 | | |
| 81 | 1000 | | | 0 | 0 | 0 | | 0 | −1 |
| 82 | 1000 | | | −1 | 0 | 0 | | 0 | 0 |
| 83 | 1000 | | | −3 | 0 | 1B | | | |
| 84 | 1000 | 0 | 0 | −3 | 0 | 1 | 1B | | |
| 85 | 1000 | 0 | 0 | −3 | 0 | 3 | 2C | | |
| 86 | 1000 | | | −3 | 0 | 0 | | −3 | 0B |
| 87 | 1000 | | | −1 | 0 | 1 | 0 | | |
| 89A | 1000 | | | −3 | 0 | 0 | | | |
| 89B | 1000 | | | −1 | 0 | 2C | | | |
| 90 | 1000 | | | −3 | 0 | 1C | | 0 | 0M |

[1] G = growth
P = phytotoxicity
A = abscission
M = morphological effects
[2] B = burning
C = chlorosis
X = dead plant

Trial 13

In another test the plant growth regulatory activity of some of the compounds of formula (VII) above, was evaluated using the following test procedure.

Seeds of tomato (*Lycopersicon esculentum*), large crabgrass (*Digitaria sanguinalis*) and pigweed (*Amaranthus retroflexus*) were planted in plastic containers. Pots used for preemergence evaluation were treated with test chemical the following day. Those used for postemergence evaluation were placed in a greenhouse and the plants were permitted to grow 13 days before treatment.

The pots were treated by spraying test formulation at a rate equivalent to 16.9 kg/ha using a modified DeVilbiss atomizer. The test formulations were prepared by dissolving 20 milligrams of test compound in 2 milliliters of a solvent system containing equal volumes of acetone and ethanol and small amounts of Toximul R and S (described more fully above). This solution was diluted to 8 milliliters with deionized water. Three milliliters of this formulation is applied to the plants or seeded containers.

After treatment the containers are placed in the greenhouse for 10 to 13 days. The plants are then evaluated and rated as follows:

1=no injury
2=slight injury
3=moderate injury
4=severe
5=death of the plant

In addition the type of plant growth regulatory effect was noted using the following ratings (which differ slightly from those used in the preceeding evaluations)

A=abscission of leaves
B=burning
C=chlorosis
D=death
E=epinasty of stem or leaves
F=formative effects
G=darker green in color
I=increased growth
L=local necrosis
N=no germination
P=purple pigmentation
R=reduced germination
S=stunting U=unclassified injury

TABLE 13

| Compound | Preemergence | | | Postemergence | | |
|---|---|---|---|---|---|---|
| | Tomato | Crab-grass | Pig-weed | Tomato | Crab-grass | Pigweed |
| 29 | 3S | 4RS | 2S | 3SB | 3SB | 2SB |
| 30 | 5N | 2S | 2S | 3BS | 2BS | 2BS |
| 31 | 5N | 4RS | 4S | 3BS | 3BS | 3BS |
| 32 | 3S | 4RS | 2S | 2BS | 2BS | 2BS |
| 33 | 3SF | 5N | 3S | 2SF | 2BS | 3BS |
| 35 | 3S | 3S | 3S | 3BS | 3BS | 3BS |
| 35 | 2S | 4SB | 2S | 3SB | 3SB | 3SB |
| 36 | 2S | 4S | 3S | 1 | 1 | 2S |
| 40 | 3S | 4RS | 2S | 1 | 2BS | 2B |
| 41 | 2S | 4RS | 2S | 2B | 2B | 2B |
| 42 | 1 | | | | | |
| 44 | 1 | 2RS | 1 | 1 | 2PBS | 1 |
| 45 | 1 | | | | | |
| 48 | 4RS | 5N | 2S | 3SB | 3SB | 3S |
| 49 | 1 | 5N | 1 | 3S | 3SB | 2S |
| 50 | 1 | 4RS | 2S | 2S | 3S | 2S |
| 51 | 1 | 3RS | 1 | 3BS | 3BS | 2BS |
| 52 | 1 | | | | | |
| 53 | 1 | 1 | 1 | 2B | 1 | 2B |
| 55 | 1 | 5N | 1 | 1 | 1 | 1 |
| 56 | 3S | 4RS | 3RS | 3SF | 3SF | 3BS |
| 57 | 1 | 4RS | 1 | 1 | 1 | 3BS |
| 58 | 1 | 4RS | 2S | 2S | 2S | 2S |
| 59 | 2S | 5N | 1 | 2S | 2S | 1 |
| 60 | 1 | 4RS | 2S | 1 | 1 | 1 |
| 61 | 1 | 4RS | 1 | 3BS | 3BS | 4BS |
| 62 | 1 | 3RS | 2S | 1 | 1 | 1 |
| 63 | 1 | 3RS | 1 | 2B | 2B | 2BS |
| 64 | 1 | 5N | 4RS | 3CBS | 3PS | 2BS |
| 64A | 1 | 2S | 2S | 1 | 1 | 1 |
| 64B | 5N | 5N | 4RS | 2FS | 1 | 1 |
| 64C | 2S | 5N | 2S | 3CBS | 4BSF | 2SB |
| 64C | 3RS | 5N | 3RS | 3CS | 3PBS | 3CBS |
| 64D | 3S | 4S | 2S | 2BS | 3BS | 2BS |
| 64E | 1 | 3S | 2S | 1 | 1 | 2B |
| 65 | 1 | 4RS | 3S | 2S | 2BS | 2SF |
| 66 | 2S | 5N | 3S | 2C | 1 | 3BS |
| 71 | 5N | 5N | 4RS | 2FS | 2S | 3FS |
| 72 | 3S | 4RS | 2S | 1 | 1 | 1 |
| 73 | 2SF | 3SF | 2SF | 2S | 2B | 2BS |
| 74 | 2S | 4RS | 3S | 3BS | 3BS | 3BS |
| 75 | 2S | 4RS | 2S | 1 | 2BS | 2BS |
| 77 | 1 | 4RS | 2S | 1 | 1 | 2S |
| 79 | 1 | 4RS | 1 | 2BS | 2BS | 3BS |
| 80 | 1 | 4RS | 2S | 1 | 1 | 2BS |
| 81 | 1 | 4RS | 1 | 1 | 1 | 1 |
| 82 | 1 | 3RS | 1 | 1 | 1 | 1 |
| 83 | 3S | 3RS | 2S | 1 | 2S | |
| 84 | 1 | 2S | 1 | 2SB | 2B | 2S |
| 85 | 1 | 4RS | 2S | 1 | 2S | 2S |
| 86 | 1 | 4RS | 1 | 1 | 2B | 2BS |
| 87 | 1 | 4RS | 2S | 1 | 1 | 1 |
| 89A | 1 | 5N | 2S | 3CS | 3BSP | 3BSF |
| 89B | 1 | 4RS | 2S | 2CS | 2CSP | 3CBS |
| 90 | 2S | 4RS | 1 | 2F | 1 | 2S |
| New | 1 | 2RS | 1 | 2S | 3BS | 2FS |
| New | 1 | 5N | 2S | 2BS | 4BS | 1 |

Trial 14

The herbicidal activity, both pre- and postemergence, of many of the compounds of formula (VIII) was determined according to the following procedure.

Each chemical to be tested was dissolved in a solvent mixture containing equal amounts of acetone and ethanol with small amounts of Toximul R and Toximul S (further identified above). The solution was diluted with deionized water to provide a test solution to give the desired rate of application of test compound to the growing flat.

Seeds of the plant species listed below for pre- and postemergence testing were planted in galvanized growing flats in sterile soil. The plant species used for preemergence testing were:
  Barnyardgrass (*Echinochloa crus-galli*)
  Crabgrass, Large (*Digitaria sanguinalis*)
  Foxtail Millet (*Setaria italica*)
  Jimsonweed (*Datura stramonium*)
  Lambsquarter (*Chenopodium album*)
  Morningglory (*Ipomoea purpurea*)
  Mustard, Indian (*Brassica juncea*)
  Oat, Wild (*Avena fatua*)
  Pigweed (*Amaranthus retroflexus*)
  Velvetleaf (*Abutilon theophrasti*)
  Zinnia (*Zinnia elegans*)
  Alfalfa (*Medicago sativa*)
  Corn (*Zea mays*)
  Cotton (*Gossypium hirsutum*)
  Cucumber (*Cucumis sativus*)
  Rice (*Oryza sativa*)
  Soybean (*Glycine max*)
  Sugar Beet (*Beta vulgaris*)
  Tomato (*Lycopersicon esculentum*)
  Wheat (*Triticum sesitivum*)

The plant species used for postemergence testing were:
  Corn (*Zea mays*)
  Crabgrass, Large (*Digitaria sanguinalis*)
  Foxtail Millet (*Setaria italica*)
  Morningglory (*Ipomoea purpurea*)
  Pigweed (*Amaranthus retroflexus*)
  Velvetleaf (*Abutilon theophrasti*)
  Zinnia (*Zinnia elegans*)

For preemergence evaluation the test solution or formulation was applied to the soil within one day of planting. For postemergence testing the formulation was applied to plants when they were about 9 days old. The test formulation was applied by spraying the formulation uniformly over the growing flat using a modified DeVilbiss atomizer using air pressure of 3–5 pounds per square inch. The rate of application, in kilograms per hectare (kg/ha), for each test is reported with the results in the following tables, 14 and 14A. Herbicidal injury to the plants was evaluated 18–21 days after treatment in the preemergence test and after about 12–14 days in the postemergence test. The degree of injury was rated using the following scale:
  1=no injury
  2=slight injury
  3=moderate injury
  4=severe injury
  5=death

TABLE 14
PREEMERGENCE

| Compound | Rate of Appln. kg/ha | Corn | Cotton | Soybean | Wheat | Alfalfa | Sugar beet | Rice | Cucumber | Tomato | Barnyard Grass | Lambs-quarter | Large Crabgrass | Mustard | Pigweed | Foxtail | Wild Oat | Velvet-leaf | Jimson-weed | Morning-glory | Zinnia |
|---|---|---|---|---|---|---|---|---|---|---|---|---|---|---|---|---|---|---|---|---|---|
| 1 | 1.1 | 1 | 1 | 1 | 1 | 1 | 1 | 1 | 1 | 1 | 1 | 1 | 1 | 1 | 1 | 1 | 1 | 1 | 1 | 1 | 1 |
|  | 2.2 | 1 | 1 | 1 | 1 | 1 | 1 | 1 | 1 | 1 | 1 | 1 | 1 | 1 | 2 | 1 | 1 | 1 | 1 | 1 | 1 |
|  | 4.5 | 1 | 1 | 1 | 1 | 1 | 1 | 1 | 1 | 1 | 1 | 1 | 4 | 1 | 2 | 2 | 1 | 1 |  | 1 | 2 |
|  | 9.0 | 1 | 1 | 1 | 3 | 1 | 1 | 1 | 2 | 1 | 2 | 2 | 4 | 1 | 2 | 4 | 1 | 2 |  | 2 | 2 |
| 2 | 1.1 | 1 | 1 | 1 | 1 | 1 | 1 | 1 | 1 | 1 | 1 | 1 | 3 | 1 | 2 | 3 | 1 | 2 |  | 2 | 3 |
|  | 2.2 | 1 | 1 | 1 | 1 | 1 | 2 | 1 | 1 | 1 | 3 | 2 | 4 | 1 | 2 | 4 | 1 | 2 | 1 | 2 | 3 |
|  | 4.5 | 1 | 1 | 1 | 3 | 1 | 3 | 3 | 3 | 2 | 4 | 3 | 4 | 2 | 3 | 4 | 3 | 3 | 1 | 3 | 3 |
|  | 9.0 | 2 | 1 | 1 | 1 | 1 | 1 | 1 | 1 | 1 | 1 | 1 | 4 | 1 | 2 | 4 | 1 | 1 |  | 1 | 1 |
| 3 | 1.1 | 1 | 1 | 1 | 1 | 1 | 1 | 1 | 1 | 1 | 2 | 2 | 3 | 1 | 2 | 2 | 1 | 2 |  | 2 | 2 |
|  | 2.2 | 1 | 1 | 1 | 1 | 1 | 2 | 1 | 2 | 1 | 2 | 2 | 4 | 1 | 3 | 3 | 1 | 2 |  | 3 | 3 |
|  | 4.5 | 2 | 1 | 1 | 1 | 1 | 2 | 3 | 2 | 2 | 2 | 3 | 4 | 2 | 3 | 4 | 1 | 3 | 1 | 3 | 3 |
|  | 9.0 | 2 |  |  |  |  |  |  |  |  |  |  | 4 |  |  |  |  |  |  |  |  |
| 5 | 1.1 | 1 |  |  |  |  |  |  |  |  |  |  | 4 |  |  | 4 |  |  |  |  | 3 |
| 6 | 9.0 | 2 |  |  |  |  |  |  |  |  |  |  | 4 |  | 3 | 3 |  |  |  | 3 | 3 |
| 7 | 9.0 | 1 |  |  |  |  |  |  |  |  |  |  | 4 |  | 3 | 2 |  | 2 |  | 2 | 2 |
| 8 | 9.0 | 1 |  |  |  |  |  |  |  |  |  |  | 4 |  | 3 | 2 |  | 2 |  | 2 | 2 |
| 9 | 9.0 | 1 |  |  |  |  |  |  |  |  |  |  | 3 |  | 3 | 3 |  | 3 |  | 2 | 3 |
| 11 | 9.0 | 1 |  |  |  |  |  |  |  |  |  |  | 3 |  | 3 | 1 |  | 1 |  | 1 | 1 |
| 12 | 9.0 | 1 |  |  |  |  |  |  |  |  |  |  | 1 |  | 1 | 1 |  | 1 |  | 1 | 1 |
| 13 | 1.1 | 1 | 1 | 1 | 1 | 1 | 1 | 1 | 1 | 1 | 1 | 1 | 3 | 1 | 2 | 2 | 1 | 2 | 1 | 2 | 2 |
|  | 2.2 | 1 | 1 | 1 | 1 | 1 | 2 | 2 | 1 | 1 | 2 | 2 | 4 | 1 | 2 | 2 | 1 | 2 | 1 | 2 | 3 |
|  | 4.5 | 1 | 1 | 1 | 1 | 1 | 2 | 3 | 1 | 2 | 4 | 2 | 2 | 1 | 2 | 4 | 1 | 3 |  | 3 | 3 |
|  | 9.0 | 2 | 1 | 1 | 3 | 2 | 2 | 1 | 1 | 1 | 4 | 2 | 4 | 5 | 4 | 4 | 2 | 1 | 1 | 1 | 1 |
| 15 | 1.1 | 1 | 1 | 1 | 2 | 1 | 2 | 3 | 2 | 2 | 3 | 2 | 4 | 1 | 4 | 4 | 2 | 3 | 1 | 3 | 3 |
|  | 2.2 | 1 | 1 | 2 | 2 | 1 | 2 | 1 | 1 | 1 | 2 | 1 | 2 | 2 | 1 | 2 | 3 | 1 | 1 | 1 | 1 |
|  | 4.5 | 1 | 1 | 1 | 1 | 1 | 1 | 1 | 1 | 1 | 3 | 2 | 3 | 1 | 2 | 3 | 1 | 2 | 1 | 2 | 2 |
|  | 9.0 | 1 | 1 | 1 | 1 | 1 | 1 | 1 | 1 | 1 | 2 | 2 | 4 | 1 | 2 | 4 | 1 | 3 | 1 | 3 | 3 |
| 18 | 1.1 | 2 | 1 | 1 | 2 | 2 | 2 | 3 | 2 | 2 | 4 | 2 | 4 | 5 | 3 | 4 | 1 | 3 |  | 3 | 3 |
|  | 2.2 | 2 | 2 | 2 | 2 | 3 | 3 | 3 | 2 | 1 | 4 | 3 | 4 | 1 | 2 | 3 | 1 | 1 |  | 2 | 2 |
|  | 4.5 | 1 | 1 | 1 | 2 | 1 | 1 | 1 | 1 | 1 | 4 | 4 | 4 | 2 | 3 | 4 | 1 | 1 | 1 | 1 | 3 |
|  | 9.0 | 1 | 1 | 1 | 1 | 1 | 1 | 1 | 1 | 1 | 1 | 2 | 2 | 1 | 2 | 2 | 2 | 1 |  | 1 | 2 |
| 19 | 1.1 | 1 | 1 | 1 | 1 | 1 | 1 | 1 | 1 | 1 | 1 | 2 | 3 | 1 | 2 | 2 | 1 | 1 |  | 1 | 1 |
|  | 0.23 | 1 | 1 | 1 | 1 | 1 | 1 | 1 | 1 | 1 | 3 | 1 | 4 | 1 | 1 | 1 | 1 | 1 | 2 | 1 | 2 |
|  | 0.56 | 1 | 1 | 1 | 1 | 1 | 2 | 2 | 1 | 2 | 1 | 2 | 3 | 1 | 3 | 3 | 1 | 3 |  | 2 | 3 |
|  | 1.1 | 1 | 1 | 2 | 1 | 1 | 2 | 3 | 1 | 2 | 2 | 1 | 3 | 2 | 2 | 2 | 2 | 1 |  | 1 | 1 |
|  | 2.2 | 1 | 1 | 2 | 1 | 1 | 1 | 2 | 1 | 2 | 3 | 2 | 3 | 1 | 1 | 2 | 3 | 1 |  | 1 | 1 |
|  | 4.5 | 1 | 1 | 1 | 2 | 1 | 1 | 1 | 1 | 1 | 1 | 1 | 2 | 1 | 1 | 1 | 1 | 1 |  | 1 | 2 |
|  | 9.0 | 1 | 1 | 1 | 2 | 1 | 2 | 1 | 1 | 1 | 3 | 3 | 3 | 1 | 3 | 3 | 1 | 2 | 2 | 2 | 2 |
| 21 | 1.0 | 1 | 1 | 1 | 1 | 1 | 1 | 1 | 1 | 1 | 1 | 2 | 4 | 1 | 2 | 4 | 1 | 3 | 1 | 3 | 3 |
|  | 2.2 | 1 | 1 | 1 | 1 | 1 | 1 | 1 | 1 | 1 | 1 | 2 | 3 | 1 | 2 | 3 | 1 | 2 | 1 | 2 | 2 |
|  | 4.5 | 1 | 2 | 2 | 2 | 2 | 2 | 3 | 3 | 3 | 3 | 3 | 4 | 2 | 3 | 4 | 1 | 2 | 2 | 2 | 2 |
|  | 9.0 | 2 | 1 | 1 | 1 | 1 | 1 | 1 | 1 | 1 | 1 | 1 | 3 | 1 | 1 | 1 | 1 | 1 | 1 | 1 | 1 |
| 22 | 9.0 | 1 |  |  |  |  |  |  |  |  |  |  | 4 |  | 3 | 4 |  | 2 |  | 2 | 3 |
| 23 | 9.0 | 1 |  |  |  |  |  |  |  |  |  |  | 4 |  | 3 | 4 |  | 2 |  | 2 | 3 |
| 24 | 1.1 | 1 | 1 | 1 | 1 | 1 | 1 | 1 | 1 | 1 | 1 | 2 | 3 | 1 | 1 | 3 | 1 | 1 | 1 | 1 | 1 |

TABLE 14-continued
PREEMERGENCE

| Compound | Rate of Appln. kg/ha | Corn | Cotton | Soy-bean | Wheat | Alfalfa | Sugar beet | Rice | Cu-cumber | Tomato | Barnyard Grass | Lambs-quarter | Large Crabgrass | Mustard | Pigweed | Foxtail | Wild Oat | Velvet-leaf | Jimson-weed | Morning-glory | Zinnia |
|---|---|---|---|---|---|---|---|---|---|---|---|---|---|---|---|---|---|---|---|---|---|
| 25 | 2.2 | 1 | 1 | 1 | 1 | 1 | 2 | 1 | 1 | 1 | 2 | 2 | 3 | 1 | 2 | 3 | 1 | 1 | 1 | 1 | 1 |
|    | 4.5 | 1 | 1 | 1 | 1 | 1 | 3 | 2 | 1 | 1 | 3 | 3 | 4 | 1 | 3 | 4 | 2 | 1 | 1 | 1 | 2 |
|    | 9.0 | 1 | 1 | 1 | 1 | 1 | 3 | 2 | 1 | 1 | 3 | 3 | 4 | 1 | 3 | 4 | 2 | 1 | 1 | 1 | 2 |
| 26 | 9.0 | 1 | 1 | 1 | 1 |   |   |   |   |   |   |   | 3 |   | 2 | 2 |   |   |   |   | 1 |
| 27 | 9.0 | 1 | 1 | 1 | 1 |   |   |   |   |   |   |   | 2 |   | 1 | 1 |   |   |   |   | 1 |
| 28 | 9.0 | 1 | 1 | 1 | 1 |   |   |   |   |   |   |   | 3 |   | 2 | 2 |   |   |   |   | 1 |
| 29 | 1.1 | 1 | 1 | 1 | 1 | 1 | 1 | 1 | 1 | 1 | 1 | 3 | 4 | 2 | 2 | 3 | 1 | 1 | 1 | 1 | 2 |
|    | 2.2 | 1 | 1 | 1 | 1 | 1 | 1 | 4 | 1 | 3 | 4 | 5 | 4 | 2 | 2 | 4 | 1 | 1 | 1 | 1 | 2 |
|    | 4.5 | 1 | 1 | 1 | 4 | 1 | 3 | 5 | 3 | 1 | 5 | 5 | 4 | 4 | 3 | 5 | 1 | 2 | 5 | 5 | 4 |
|    | 9.0 | 1 | 1 | 1 | 1 | 1 | 1 | 1 | 1 | 1 | 1 | 1 | 2 | 1 | 1 | 1 | 1 | 1 | 1 | 1 | 1 |
| 30 | 1.1 | 1 | 1 | 1 | 1 | 1 | 1 | 1 | 1 | 1 | 1 | 3 | 3 | 2 | 2 | 3 | 1 | 1 | 1 | 1 | 1 |
|    | 2.2 | 1 | 1 | 1 | 1 | 1 | 1 | 1 | 1 | 1 | 1 | 2 | 4 | 1 | 1 | 2 | 1 | 2 | 1 | 1 | 2 |
|    | 4.5 | 1 | 1 | 1 | 1 | 1 | 1 | 1 | 1 | 1 | 1 | 2 | 3 | 1 | 1 | 4 | 1 | 1 | 1 | 1 | 2 |
|    | 9.0 | 1 | 1 | 1 | 1 | 1 | 1 | 1 | 1 | 1 | 1 | 2 | 5 | 1 | 3 | 4 | 1 | 4 | 1 | 1 | 2 |
| 31 | 1.1 | 1 | 1 | 1 | 1 | 1 | 1 | 1 | 1 | 1 | 1 | 1 | 1 | 1 | 1 | 1 | 1 | 1 | 1 | 1 | 1 |
|    | 2.2 | 1 | 1 | 1 | 1 | 1 | 1 | 1 | 1 | 1 | 1 | 2 | 3 | 1 | 2 | 4 | 1 | 1 | 1 | 1 | 2 |
|    | 4.5 | 1 | 1 | 1 | 1 | 1 | 1 | 1 | 1 | 1 | 1 | 2 | 4 | 1 | 1 | 3 | 1 | 2 | 1 | 1 | 2 |
|    | 9.0 | 1 | 1 | 1 | 1 | 1 | 1 | 1 | 1 | 1 | 1 | 2 | 4 | 1 | 2 | 4 | 1 | 2 | 1 | 2 | 3 |
| 32 | 1.1 | 1 | 4 | 3 | 1 | 1 | 2 | 4 | 1 | 2 | 3 | 3 | 4 | 1 | 2 | 4 | 1 | 4 | 3 | 2 | 2 |
|    | 2.2 | 3 | 5 | 4 | 3 | 1 | 3 | 5 | 5 | 3 | 5 | 3 | 5 | 4 | 3 | 3 | 2 | 1 | 5 | 2 | 3 |
|    | 4.5 | 2 | 2 | 1 | 3 | 1 | 3 | 5 | 3 | 3 | 5 | 4 | 4 | 1 | 2 | 5 | 3 | 3 | 3 | 1 | 2 |
|    | 9.0 | 1 | 1 | 1 | 1 | 1 | 1 | 1 | 1 | 1 | 1 | 1 | 4 | 1 | 1 | 4 | 1 | 1 | 1 | 1 | 1 |
| 33 | 1.1 | 1 | 1 | 1 | 1 | 1 | 1 | 1 | 1 | 1 | 1 | 1 | 3 | 1 | 1 | 3 | 1 | 2 | 1 | 1 | 2 |
|    | 0.23 | 1 | 1 | 1 | 1 | 1 | 1 | 1 | 1 | 1 | 1 | 1 | 2 | 1 | 1 | 3 | 1 | 2 | 1 | 1 | 2 |
|    | 0.56 | 1 | 1 | 1 | 1 | 1 | 1 | 1 | 1 | 1 | 1 | 1 | 3 | 1 | 2 | 3 | 1 | 2 | 3 | 1 | 1 |
|    | 1.1 | 1 | 1 | 1 | 1 | 1 | 1 | 2 | 2 | 2 | 3 | 3 | 4 | 2 | 2 | 3 | 1 | 2 | 1 | 1 | 2 |
|    | 2.2 | 1 | 1 | 1 | 1 | 1 | 1 | 1 | 1 | 3 | 3 | 5 | 4 | 2 | 3 | 4 | 1 | 2 | 2 | 1 | 1 |
|    | 4.5 | 2 | 3 | 3 | 1 | 1 | 3 | 3 | 1 | 4 | 3 | 5 | 4 | 1 | 2 | 4 | 1 | 2 | 3 | 2 | 1 |
|    | 9.0 | 1 | 1 | 1 | 1 | 1 | 1 | 1 | 1 | 1 | 1 | 1 | 3 | 1 | 1 | 4 | 1 | 1 | 1 | 1 | 1 |
| 34 | 1.1 | 1 | 1 | 1 | 1 | 1 | 2 | 1 | 1 | 1 | 1 | 3 | 4 | 1 | 2 | 4 | 1 | 3 | 2 | 1 | 2 |
| 35 | 2.2 | 4 | 1 | 1 | 1 | 1 | 2 | 3 | 3 | 2 | 3 | 3 | 4 | 2 | 3 | 5 | 2 | 3 | 1 | 2 | 2 |
|    | 4.5 | 1 | 1 | 1 | 1 | 1 | 3 | 3 | 3 | 3 | 3 | 3 | 5 | 2 | 3 | 5 | 3 | 2 | 2 | 2 | 3 |
|    | 9.0 | 2 | 1 | 1 | 1 | 1 | 1 | 1 | 1 | 1 | 1 | 1 | 4 | 1 | 1 | 4 | 1 | 2 | 1 | 1 | 1 |
| 36 | 1.1 | 1 | 1 | 1 | 1 | 1 | 1 | 1 | 2 | 1 | 1 | 1 | 2 | 2 | 2 | 4 | 1 | 2 | 1 | 1 | 2 |
|    | 2.2 | 2 | 1 | 1 | 1 | 1 | 1 | 2 | 1 | 1 | 1 | 1 | 4 | 1 | 2 | 4 | 1 | 2 | 1 | 1 | 2 |
|    | 4.5 | 1 | 1 | 1 | 1 | 1 | 1 | 1 | 1 | 1 | 1 | 1 | 2 | 1 | 3 | 2 | 1 | 1 | 2 | 2 | 3 |
|    | 9.0 | 1 | 1 | 1 | 1 | 1 | 1 | 1 | 1 | 1 | 1 | 1 | 1 | 1 | 1 | 1 | 1 | 1 | 1 | 1 | 1 |
| 39 | 1.1 | 1 | 1 | 1 | 1 | 1 | 1 | 1 | 1 | 1 | 1 | 1 | 4 | 1 | 2 | 4 | 1 | 1 | 1 | 1 | 1 |
|    | 2.2 | 1 | 1 | 1 | 1 | 1 | 1 | 1 | 1 | 1 | 1 | 1 | 4 | 1 | 1 | 3 | 1 | 1 | 1 | 1 | 2 |
|    | 4.5 | 1 | 1 | 1 | 1 | 1 | 1 | 1 | 1 | 1 | 1 | 1 | 4 | 1 | 1 | 1 | 1 | 1 | 1 | 1 | 1 |
|    | 9.0 | 1 | 1 | 1 | 1 | 1 | 1 | 1 | 1 | 1 | 1 | 1 | 1 | 1 | 1 | 1 | 1 | 1 | 1 | 1 | 1 |
| 40 | 1.1 | 1 | 2 | 1 | 1 | 1 | 1 | 1 | 1 | 1 | 1 | 1 | 4 | 1 | 1 | 1 | 1 | 1 | 1 | 1 | 1 |
|    | 2.2 | 1 | 1 | 1 | 1 | 1 | 1 | 1 | 1 | 1 | 1 | 1 | 1 | 1 | 1 | 1 | 1 | 1 | 1 | 1 | 1 |
|    | 4.5 | 1 | 1 | 1 | 1 | 1 | 1 | 1 | 1 | 1 | 1 | 3 | 1 | 1 | 1 | 1 | 1 | 1 | 1 | 1 | 1 |

TABLE 14-continued
PREEMERGENCE

| Compound | Rate of Appln. kg/ha | Corn | Cotton | Soybean | Wheat | Alfalfa | Sugar beet | Rice | Cucumber | Tomato | Barnyard Grass | Lambs-quarter | Large Crabgrass | Mustard | Pigweed | Foxtail | Wild Oat | Velvet-leaf | Jimson-weed | Morning-glory | Zinnia |
|---|---|---|---|---|---|---|---|---|---|---|---|---|---|---|---|---|---|---|---|---|---|
| 41 | 9.0 | 1 | 1 | 1 | 1 | 1 | 1 | 1 | 1 | 1 | 1 | 1 | 4 | — | 2 | 4 | — | 2 | — | — | 1 |
|  | 1.1 | 1 | 1 | 1 | 1 | 1 | 1 | 1 | 1 | 1 | 1 | 1 | 1 | — | 1 | 1 | 1 | 1 | — | — | 1 |
|  | 2.2 | 1 | 1 | 1 | 1 | 1 | 1 | 1 | 1 | 1 | 1 | 1 | 2 | 2 | 2 | 2 | 1 | 1 | 1 | 1 | 2 |
|  | 4.5 | 2 | 2 | 1 | 1 | 1 | 1 | 1 | 1 | 1 | 1 | 2 | 2 | 2 | 3 | 4 | 1 | 3 | 1 | 2 | 3 |
|  | 9.0 | 2 | 1 | 1 | 1 | 1 | 1 | 1 | 1 | 1 | 1 | 1 | 4 | — | 2 | 5 | — | 2 | — | 2 | 2 |
| 48 | 9.0 | 1 | 1 | 1 | 1 | 1 | 1 | 1 | 1 | 1 | 1 | 1 | 4 | — | 2 | 3 | — | 2 | 1 | — | 1 |
| 49 | 1.1 | 2 | 2 | 1 | 1 | 1 | 1 | 2 | 1 | 2 | 3 | 2 | 4 | 2 | 2 | 4 | 2 | 1 | 2 | — | 2 |
|  | 2.2 | 1 | 1 | 1 | 1 | 1 | 1 | 3 | 1 | 2 | 3 | 3 | 4 | 3 | 2 | 4 | 2 | 2 | 2 | 2 | 1 |
|  | 4.5 | 2 | 1 | 2 | 1 | 1 | 2 | 3 | 3 | 2 | 3 | 3 | 4 | 2 | — | 4 | — | — | — | — | 1 |
|  | 9.0 | 1 | 1 | 1 | 1 | 1 | 1 | 1 | 1 | 1 | 1 | 1 | 4 | — | 1 | 4 | — | 1 | — | — | 1 |
| 50 | 1.1 | 1 | 1 | 1 | 1 | 1 | 1 | 1 | 1 | 1 | 1 | 1 | 1 | — | 1 | 2 | — | 1 | — | — | 1 |
|  | 2.2 | 1 | 1 | 1 | 1 | 1 | 1 | 1 | 1 | 1 | 1 | 1 | 3 | 1 | 2 | 3 | 1 | 2 | — | — | 1 |
|  | 4.5 | 1 | 1 | 2 | 1 | 1 | 2 | 1 | 1 | 1 | 1 | 1 | 3 | 1 | 1 | 4 | 1 | 1 | — | — | 1 |
|  | 9.0 | 1 | 1 | 1 | 1 | 1 | 1 | 1 | 1 | 1 | 1 | 1 | 4 | — | 1 | 4 | — | 1 | — | — | 1 |
| 55 | 1.1 | 1 | 1 | 1 | 1 | 1 | 1 | 1 | 1 | 1 | 1 | 1 | 1 | — | 1 | 1 | — | 1 | — | — | 1 |
|  | 2.2 | 1 | 1 | 1 | 1 | 1 | 1 | 1 | 1 | 1 | 1 | 1 | 3 | — | 2 | 3 | — | 2 | — | — | 1 |
|  | 4.5 | 1 | 1 | 1 | 1 | 1 | 2 | 1 | 1 | 1 | 1 | 3 | 3 | — | 1 | 3 | — | 1 | — | — | 1 |
|  | 9.0 | 1 | 1 | 1 | 1 | 1 | 1 | 1 | 1 | 1 | 1 | 1 | 4 | — | 3 | 4 | — | 2 | — | — | 1 |
| 58 | 1.1 | 1 | 1 | 1 | 1 | 1 | 1 | 1 | 1 | 1 | 1 | 1 | 2 | — | 2 | 1 | — | 1 | — | — | 1 |
|  | 2.2 | 1 | 1 | 1 | 1 | 1 | 1 | 1 | 1 | 1 | 1 | 1 | 2 | — | 1 | 2 | — | 1 | — | — | 1 |
|  | 4.5 | 1 | 1 | 1 | 1 | 1 | 2 | 1 | 1 | 1 | 1 | 1 | 2 | — | 1 | 3 | — | 1 | — | — | 1 |
|  | 9.0 | 1 | 1 | 1 | 1 | 1 | 1 | 1 | 1 | 1 | 1 | 1 | 4 | — | 4 | 4 | — | 2 | — | — | 1 |
| 59 | 9.0 | 1 | 1 | 1 | 1 | 1 | 1 | 1 | 1 | 1 | 1 | 1 | 3 | — | 1 | 1 | — | 1 | — | — | 1 |
| 60 | 9.0 | 1 | 1 | 1 | 1 | 1 | 1 | 1 | 1 | 1 | 1 | 1 | 2 | — | 1 | 2 | — | 2 | — | — | 3 |
| 61 | 9.0 | 1 | 1 | 1 | 1 | 1 | 1 | 1 | 1 | 1 | 1 | 1 | 3 | — | 3 | 3 | — | 1 | — | — | 3 |
| 64 | 1.1 | 2 | 1 | 1 | 3 | 1 | 1 | 1 | 3 | 3 | 4 | 5 | 5 | 4 | 5 | 5 | 3 | 2 | 1 | 1 | 3 |
|  | 2.2 | 2 | 2 | 1 | 3 | 1 | 1 | 1 | 3 | 3 | 3 | 2 | 4 | 3 | 2 | 4 | 3 | 3 | 1 | 3 | 4 |
|  | 4.5 | 4 | 2 | 1 | 3 | 2 | 3 | 2 | 1 | 3 | 4 | 5 | 5 | — | 4 | 5 | 4 | 3 | 1 | 4 | 4 |
|  | 9.0 | 3 | 1 | 1 | 3 | 1 | 1 | 2 | 1 | 1 | 4 | 4 | 4 | — | 3 | 4 | — | 3 | — | — | 3 |
|  | 1.1 | 2 | 1 | 1 | 1 | 1 | 1 | 2 | 1 | 1 | 4 | 4 | 3 | 1 | 3 | 4 | 3 | 3 | 2 | 3 | 3 |
|  | 0.23 | 2 | 1 | 1 | 2 | 1 | 1 | 3 | 1 | 1 | 1 | 1 | 3 | 1 | 2 | 4 | 1 | 2 | 1 | 2 | 2 |
|  | 0.56 | 2 | 1 | 1 | 1 | 1 | 1 | 1 | 1 | 1 | 4 | 4 | 4 | 1 | 3 | 4 | 2 | 2 | 3 | 2 | 2 |
| 64B | 9.0 | 1 | 1 | 1 | 1 | 1 | 1 | 1 | 1 | 1 | 1 | 1 | 3 | — | 2 | 2 | — | 1 | — | — | 1 |
| 65 | 1.1 | 1 | 1 | 1 | 1 | 1 | 1 | 1 | 1 | 1 | 2 | 2 | 4 | 1 | 1 | 3 | 1 | 1 | — | — | 2 |
|  | 2.2 | 1 | 1 | 1 | 1 | 1 | 1 | 1 | 1 | 1 | 3 | 3 | 4 | — | 3 | 4 | 1 | 1 | — | — | 2 |
|  | 4.5 | 1 | 1 | 1 | 1 | 1 | 1 | 1 | 1 | 1 | 4 | 4 | 4 | — | 3 | 4 | — | 3 | — | 1 | 1 |
|  | 9.0 | 1 | 1 | 1 | 1 | 1 | 1 | 1 | 1 | 1 | 1 | 1 | 4 | — | 1 | 5 | — | 1 | — | — | 2 |
| 66 | 1.1 | 1 | 1 | 1 | 1 | 1 | 1 | 1 | 1 | 1 | 1 | 3 | 3 | — | 2 | 3 | — | 1 | — | — | 1 |
|  | 2.2 | 1 | 2 | 1 | 2 | 1 | 1 | 1 | 1 | 1 | 1 | 3 | 4 | 2 | 2 | 4 | — | 1 | 1 | 1 | 2 |
|  | 4.5 | 1 | 1 | 1 | 1 | 1 | 1 | 1 | 1 | 1 | 1 | 4 | 4 | 3 | 3 | 4 | — | 2 | 3 | 2 | 2 |
|  | 9.0 | 1 | 1 | 1 | 1 | 1 | 1 | 1 | 1 | 1 | 1 | 1 | 3 | — | 1 | 4 | — | 1 | — | — | 1 |
| 67 | 1.1 | 1 | 1 | 1 | 1 | 1 | 1 | 1 | 1 | 1 | 1 | 2 | 3 | 1 | 3 | 3 | — | 1 | — | — | 1 |
| 70 | 2.2 | 1 | 1 | 1 | 1 | 1 | 2 | 2 | 2 | 1 | 2 | 2 | 3 | 1 | 3 | 3 | — | 1 | — | 1 | 2 |
|  | 4.5 | 1 | 1 | 1 | 1 | 1 | 2 | 2 | 2 | 1 | 4 | 2 | 5 | 1 | 3 | 4 | — | 3 | — | 2 | 3 |
|  | 9.0 | 2 | 1 | 1 | 1 | — | 1 | 2 | 2 | 1 | — | — | 4 | — | 2 | 4 | — | — | — | — | 1 |
| 72 | 9.0 | 1 | 1 | 1 | 1 | 1 | 1 | 1 | 1 | 1 | 1 | 1 | 3 | — | 2 | 2 | — | 1 | — | 1 | 2 |
| 74 | 9.0 | 1 | 1 | 1 | 1 | 1 | 1 | 1 | 1 | 1 | 1 | 1 | 3 | — | 2 | 2 | — | 1 | — | 1 | 1 |
| 75 | 9.0 | 1 | 1 | 1 | 1 | 1 | 1 | 1 | 1 | 1 | 1 | 1 | 2 | — | 2 | 2 | — | 1 | — | 1 | 1 |

TABLE 14-continued
PREEMERGENCE

| Compound | Rate of Appln. kg/ha | Corn | Cotton | Soybean | Wheat | Alfalfa | Sugar beet | Rice | Cucumber | Tomato | Barnyard Grass | Lambsquarter | Large Crabgrass | Mustard | Pigweed | Foxtail | Wild Oat | Velvetleaf | Jimsonweed | Morningglory | Zinnia |
|---|---|---|---|---|---|---|---|---|---|---|---|---|---|---|---|---|---|---|---|---|---|
| 76 | 1.1 | 1 | 1 | 1 | 1 | 1 | 1 | 1 | 1 | 1 | 1 | 1 | 1 | 1 | 1 | 1 | 1 | 1 | 1 | 1 | 1 |
|  | 2.2 | 1 | 1 | 1 | 1 | 1 | 1 | 1 | 1 | 1 | 1 | 2 | 3 | 1 | 2 | 3 | 1 | 1 | 1 | 1 | 1 |
|  | 4.5 | 1 | 1 | 1 | 1 | 1 | 2 | 1 | 1 | 1 | 1 | 2 | 3 | 1 | 3 | 3 | 1 | 2 | 1 | 1 | 1 |
|  | 9.0 | 1 | 1 | 1 | 1 | 1 | 2 | 1 | 1 | 1 | 1 | 5 | 3 | 3 | 4 | 4 | 3 | 2 | 1 | 2 | 1 |
| 78 | 1.1 | 1 | 1 | 1 | 1 | 1 | 1 | 1 | 1 | 1 | 1 | 2 | 3 | 1 | 1 | 1 | 1 | 1 | 1 | 1 | 1 |
|  | 2.2 | 1 | 2 | 1 | 1 | 1 | 1 | 1 | 1 | 1 | 1 | 2 | 3 | 1 | 2 | 2 | 1 | 2 | 1 | 1 | 1 |
|  | 4.5 | 1 | 1 | 1 | 1 | 1 | 2 | 1 | 1 | 1 | 1 | 2 | 4 | 2 | 2 | 2 | 1 | 2 | 1 | 1 | 1 |
|  | 9.0 | 1 | 1 | 1 | 1 | 1 | 2 | 1 | 1 | 1 | 1 | 2 | 3 | 2 | 2 | 1 | 4 | 1 | 1 | 2 | 1 |
| 79 | 1.1 | 1 | 1 | 1 | 1 | 1 | 1 | 1 | 1 | 1 | 1 | 1 | 1 | 2 | 1 | 1 | 1 | 1 | 1 | 1 | 2 |
|  | 2.2 | 2 | 1 | 1 | 1 | 1 | 1 | 1 | 1 | 1 | 2 | 1 | 2 | 2 | 2 | 2 | 2 | 2 | 1 | 2 | 2 |
|  | 4.5 | 1 | 1 | 2 | 1 | 1 | 2 | 1 | 2 | 2 | 2 | 2 | 3 | 2 | 3 | 4 | 1 | 1 | 1 | 2 | 3 |
|  | 9.0 | 2 | 1 | 1 | 1 | 1 | 1 | 1 | 1 | 1 | 1 |   | 3 | 4 | 1 | 4 | 1 | 1 | 1 | 1 | 1 |
| 80 | 9.0 | 1 | 1 | 1 | 1 | 1 | 1 | 1 | 1 | 1 | 1 |   |   | 1 | 1 | 1 | 1 |   |   | 1 | 1 |
| 81 | 9.0 | 1 | 1 | 1 | 1 | 1 | 1 | 2 | 1 | 1 | 1 | 1 |   | 3 | 1 | 1 | 1 | 1 | 1 | 1 | 2 |
| 83 | 1.1 | 1 | 1 | 1 | 1 | 1 | 1 | 3 | 2 | 1 | 1 | 1 | 1 | 3 | 1 | 2 | 2 | 1 | 1 | 1 | 3 |
|  | 2.2 | 1 | 1 | 1 | 1 | 1 | 3 | 1 | 1 | 1 | 1 | 1 | 2 | 2 | 3 | 1 | 1 | 1 | 1 | 1 | 1 |
|  | 4.5 | 3 | 1 | 1 | 1 | 1 | 1 | 1 | 1 | 1 | 1 |   |   | 5 | 1 | 3 | 1 | 3 |   |   | 1 |
|  | 9.0 | 1 | 1 | 1 | 1 | 1 | 1 | 2 | 1 | 1 | 1 | 2 | 2 | 3 | 1 | 3 | 1 | 1 | 1 | 2 | 3 |
| 85 | 1.1 | 1 | 1 | 1 | 1 | 1 | 1 | 1 | 1 | 1 | 1 | 1 | 2 | 4 | 1 | 3 | 1 | 1 | 1 | 1 | 1 |
|  | 2.2 | 2 | 1 | 1 | 1 | 1 | 1 | 1 | 1 | 1 | 1 | 2 | 2 | 4 | 1 | 3 | 1 | 1 | 1 | 2 | 5 |
|  | 4.5 | 1 | 1 | 1 | 1 | 2 | 1 | 1 | 2 | 2 | 1 |   |   | 4 |   | 2 | 1 | 3 | 1 | 1 | 1 |
|  | 9.0 | 2 | 1 | 1 | 1 | 1 | 1 | 1 | 1 | 1 | 1 |   |   | 4 |   | 2 | 1 | 1 | 1 | 1 | 2 |
| 86 | 1.1 | 1 | 1 | 1 | 1 | 1 | 1 | 1 | 1 | 1 | 1 | 2 | 1 | 4 | 1 | 3 | 2 | 1 | 1 | 2 | 1 |
|  | 2.2 | 1 | 1 | 1 | 2 | 1 | 1 | 1 | 2 | 2 | 2 | 3 | 2 | 4 | 1 | 3 | 4 | 1 | 1 | 2 | 5 |
|  | 4.5 | 1 | 1 | 1 | 2 | 1 | 1 | 3 | 1 | 1 | 1 | 3 | 2 | 4 | 1 | 3 | 4 | 1 | 2 | 2 | 2 |
|  | 9.0 | 1 | 1 | 1 | 1 | 1 | 1 | 1 | 1 | 1 | 1 | 1 | 1 | 2 | 1 | 1 | 2 | 1 | 1 | 1 | 1 |
| 88 | 1.1 | 1 | 1 | 1 | 1 | 1 | 1 | 1 | 1 | 1 | 1 | 1 | 1 | 1 | 2 | 1 | 1 | 1 |   | 1 | 1 |
| 90 | 2.2 | 1 | 1 | 1 | 1 | 1 | 2 | 1 | 1 | 1 | 1 | 1 | 1 | 4 | 1 | 2 | 2 | 2 | 1 | 1 | 2 |
|  | 4.5 | 1 | 1 | 1 | 1 | 1 | 1 | 2 | 1 | 1 | 1 |   |   | 4 |   | 2 | 5 | 2 |   | 1 | 1 |
|  | 9.0 | 1 | 1 | 1 | 1 | 1 | 1 |   |   |   |   |   |   | 4 |   | 3 |   | 2 |   | 2 | 2 |

TABLE 14A

| Compound | Appln Rate kg/ha | Postemergence | | | | | |
|---|---|---|---|---|---|---|---|
| | | Large Crabgrass | Pigweed | Foxtail | Velvet Leaf | Morningglory | Zinnia |
| 1 | 9.0 | 1 | 1 | 1 | 1 | 1 | 1 |
| 3 | 9.0 | 1 | 1 | 1 | 1 | 1 | 1 |
| 5 | 1.1 | 1 | 1 | 1 | 1 | 1 | 1 |
| 18 | 9.0 | 1 | 1 | 2 | 1 | 1 | 1 |
| 19 | 9.0 | 2 | 2 | 2 | 2 | 2 | 2 |
| 19 | 9.0 | 1 | 1 | 1 | 1 | 1 | 1 |
| 23 | 9.0 | 1 | 1 | 1 | 1 | 1 | 1 |
| 24 | 9.0 | 1 | 1 | 1 | 1 | 1 | 1 |
| 25 | 9.0 | 1 | 1 | 1 | 1 | 1 | 1 |
| 26 | 9.0 | 1 | 1 | 1 | 1 | 1 | 1 |
| 27 | 9.0 | 1 | 1 | 1 | 1 | 1 | 1 |
| 48 | 9.0 | 2 | 2 | 2 | 2 | 1 | 2 |
| 61 | 9.0 | 1 | 1 | 1 | 1 | 1 | 1 |
| 64C | 9.0 | 3 | 2 | 3 | 2 | 3 | 3 |

The results obtained in the experiments described and reported above show the novel substituted 1-thia-3-aza-4-one derivatives disclosed herein are effective in the disclosed and claimed methods of regulating the growth of submerged and floating aquatic plants, of protecting plants from phytopathogenic fungi, of regulating the growth of terrestrial plants such as wheat and barley, and controlling undesired plant growth.

I claim:

1. A method of protecting plants from phytopathogenic fungi which comprises contacting the fungi with a fungicidally-effective and non-herbicidal amount of a compound of the formula

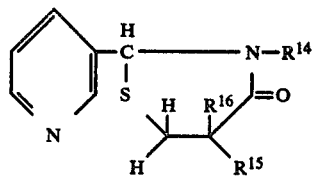

(V)

wherein
$R^{14}$ is $C_3$–$C_6$ alkyl, $C_5$–$C_6$ cycloalkyl, halobenzyl, halophenyl, trifluoromethylphenyl, tolyl, or methoxyphenyl;
$R^{15}$ is hydrogen or methyl; and
$R^{16}$ is hydrogen or methyl;
or an acid addition salt thereof.

2. The method of claim 1 wherein said compound is applied in combination with an inert diluent.

3. The method of claim 1 wherein said compound is applied in combination with an inert diluent and a wetting agent.

4. The method of claim 1 wherein said compound is applied at a rate within the range of from about 5 to about 1000 ppm.

5. The method of claim 1 wherein the fungicidally-effective compound is 3-(4-chlorophenyl)tetrahydro-5-methyl-2-(3-pyridyl)-4H-1,3-thiazin-4-one.

* * * * *